US011623941B2

(12) United States Patent
Forss et al.

(10) Patent No.: US 11,623,941 B2
(45) Date of Patent: *Apr. 11, 2023

(54) SEPARATION METHOD

(71) Applicant: Cytiva BioProcess R&D AB, Uppsala (SE)

(72) Inventors: Annika Kristina Forss, Uppsala (SE); Gustav Jose Rodrigo, Uppsala (SE); Tomas Bjorkman, Uppsala (SE); Jesper Ulf Hansson, Uppsala (SE); Mats Ander, Uppsala (SE)

(73) Assignee: CYTIVA BIOPROCESS R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,475

(22) Filed: May 27, 2020

(65) Prior Publication Data

US 2020/0283475 A1 Sep. 10, 2020

Related U.S. Application Data

(63) Continuation of application No. 15/348,699, filed on Nov. 10, 2016, now Pat. No. 10,703,774, which is a continuation-in-part of application No. 15/282,367, filed on Sep. 30, 2016, now Pat. No. 10,654,887.

(51) Int. Cl.
| | | |
|---|---|---|
| C07K 1/22 | (2006.01) |
| B01D 15/08 | (2006.01) |
| C07K 16/12 | (2006.01) |
| C07K 17/10 | (2006.01) |
| B01J 20/286 | (2006.01) |
| C07K 14/31 | (2006.01) |
| C07K 16/06 | (2006.01) |
| B01D 15/00 | (2006.01) |
| B01J 20/32 | (2006.01) |

(52) U.S. Cl.
CPC ............... *C07K 1/22* (2013.01); *B01D 15/00* (2013.01); *B01J 20/286* (2013.01); *B01J 20/3212* (2013.01); *B01J 20/3274* (2013.01); *C07K 14/31* (2013.01); *C07K 16/065* (2013.01); *C07K 16/1271* (2013.01); *C07K 17/10* (2013.01); *B01J 2220/52* (2013.01)

(58) Field of Classification Search
None
See application file for complete search history.

(56) References Cited

U.S. PATENT DOCUMENTS

| | | | |
|---|---|---|---|
| 4,704,366 A | 11/1987 | Juarez-Salinas et al. |
| 4,708,714 A | 11/1987 | Larsson et al. |
| 4,801,687 A | 1/1989 | Ngo et al. |
| 4,933,435 A | 6/1990 | Ngo |
| 5,011,686 A | 4/1991 | Pang |
| 5,084,398 A | 1/1992 | Huston et al. |
| 5,143,844 A | 9/1992 | Abrahmsen et al. |
| 5,476,786 A | 12/1995 | Huston |
| 5,831,012 A | 11/1998 | Nilsson et al. |
| 6,127,526 A | 10/2000 | Blank |
| 6,207,804 B1 | 3/2001 | Huston et al. |
| 6,399,750 B1 | 6/2002 | Johansson |
| 6,602,990 B1 * | 8/2003 | Berg ...................... B01J 20/262 536/124 |
| 6,870,034 B2 | 3/2005 | Breece et al. |
| 7,220,356 B2 | 5/2007 | Thommes et al. |
| 7,396,467 B2 | 7/2008 | Berg et al. |
| 7,566,565 B2 | 7/2009 | Peters et al. |
| 7,709,209 B2 | 5/2010 | Hober et al. |
| 7,714,111 B2 | 5/2010 | Sun et al. |
| 7,820,799 B2 | 10/2010 | Godavarti et al. |
| 7,834,158 B2 | 11/2010 | Hober |
| 7,834,162 B2 | 11/2010 | Zhou |
| 7,884,264 B2 | 2/2011 | Dickey et al. |
| 7,901,581 B2 | 3/2011 | Bryntesson et al. |
| 8,080,246 B2 | 12/2011 | Lin et al. |
| 8,084,032 B2 | 12/2011 | Yumioka et al. |
| 8,182,696 B2 | 5/2012 | Theoleyre et al. |
| 8,183,207 B2 | 5/2012 | Lin et al. |
| 8,198,404 B2 | 6/2012 | Hober |
| 8,263,750 B2 | 9/2012 | Shukla et al. |
| 8,282,914 B2 | 10/2012 | Chou et al. |
| 8,329,660 B2 | 12/2012 | Kuchroo et al. |
| 8,329,860 B2 | 12/2012 | Hall et al. |
| 8,329,869 B2 | 12/2012 | Kraynov et al. |

(Continued)

FOREIGN PATENT DOCUMENTS

| | | |
|---|---|---|
| EP | 2202310 A2 | 6/2010 |
| EP | 2412809 A1 | 2/2012 |

(Continued)

OTHER PUBLICATIONS

Japanese Office Action for JP Application No. 2018-558395 dated May 24, 2021 (11 pages with English translation).

(Continued)

*Primary Examiner* — Stacy B Chen
(74) *Attorney, Agent, or Firm* — Eversheds Sutherland (US) LLP

(57) ABSTRACT

The invention relates to a method of isolating an immunoglobulin, comprising the steps of:

a) providing a separation matrix comprising multimers of immunoglobulin-binding alkali-stabilized Protein A domains covalently coupled to a porous support, b) contacting a liquid sample comprising an immunoglobulin with the separation matrix, c) washing said separation matrix with a washing liquid, d) eluting the immunoglobulin from the separation matrix with an elution liquid, and e) cleaning the separation matrix with a cleaning liquid, wherein the alkali-stabilized Protein A domains comprise mutants of a parental Fc-binding domain of Staphylococcus Protein A (SpA), as defined by SEQ ID NO: 51 or SEQ ID NO: 52, wherein the amino acid residues at positions 13 and 44 of SEQ ID NO: 51 or 52 are asparagines and wherein at least the asparagine residue at position 3 of SEQ ID NO: 51 or 52 has been mutated to an amino acid selected from the group consisting of glutamic acid, lysine, tyrosine, threonine, phenylalanine, leucine, isoleucine, tryptophan, methionine, valine, alanine, histidine and arginine.

20 Claims, 9 Drawing Sheets

Specification includes a Sequence Listing.

(56) References Cited

U.S. PATENT DOCUMENTS

| | | |
|---|---|---|
| 8,354,510 B2 | 1/2013 | Hober et al. |
| 8,377,448 B2 | 2/2013 | Smith et al. |
| 8,586,713 B2 | 11/2013 | Davis et al. |
| 8,592,555 B2 | 11/2013 | Spector |
| 8,617,881 B2 | 12/2013 | Coljee et al. |
| 8,674,073 B2 | 3/2014 | Majima et al. |
| 8,728,479 B2 | 5/2014 | Greene et al. |
| 8,772,447 B2 | 7/2014 | Hall et al. |
| 8,822,642 B2 | 9/2014 | Levin et al. |
| 8,853,371 B2 | 10/2014 | Alfonso et al. |
| 8,859,726 B2 | 10/2014 | Bjorkman et al. |
| 8,883,134 B2 | 11/2014 | Cho et al. |
| 8,889,706 B2 | 11/2014 | Spector et al. |
| 9,018,305 B2 | 4/2015 | Spector et al. |
| 9,024,000 B2 | 5/2015 | Jeon et al. |
| 9,040,661 B2 | 5/2015 | Nakamura et al. |
| 9,051,375 B2 | 6/2015 | Li et al. |
| 9,073,970 B2 | 7/2015 | Muller-Spath et al. |
| 9,149,738 B2 | 10/2015 | Skudas |
| 9,156,892 B2 | 10/2015 | Hober |
| 9,162,161 B2 | 10/2015 | Tamori et al. |
| 9,187,555 B2 | 11/2015 | Bjorkman et al. |
| 9,266,939 B2 | 2/2016 | Crine et al. |
| 9,284,347 B2 | 3/2016 | Eckermann et al. |
| 9,290,549 B2 | 3/2016 | Hall et al. |
| 9,290,573 B2 | 3/2016 | Cong et al. |
| 9,296,791 B2 | 3/2016 | Hober et al. |
| 9,382,305 B2 | 7/2016 | Wilmen et al. |
| 9,481,730 B2 | 11/2016 | Bruenker et al. |
| 9,493,529 B2 | 11/2016 | Blanche et al. |
| 9,499,608 B2 | 11/2016 | Chen et al. |
| 9,517,264 B2 | 12/2016 | Fachini et al. |
| 9,534,023 B2 | 1/2017 | Hober |
| 9,540,442 B2 | 1/2017 | Tsurushita |
| 9,556,258 B2 | 1/2017 | Nti-Gyabaah et al. |
| 9,573,989 B2 | 2/2017 | Watzig et al. |
| 9,587,235 B2 | 3/2017 | Buechler et al. |
| 9,637,541 B2 | 5/2017 | Kim et al. |
| 9,637,557 B2 | 5/2017 | Scheer et al. |
| 9,650,422 B2 | 5/2017 | Chang et al. |
| 9,662,373 B2 | 5/2017 | Cload et al. |
| 9,676,871 B2 | 6/2017 | Strop et al. |
| 9,688,978 B2 | 6/2017 | Buechler et al. |
| 9,695,233 B2 | 7/2017 | Duerr et al. |
| 9,708,405 B2 | 7/2017 | Liu et al. |
| 9,714,292 B2 | 7/2017 | Auer et al. |
| 9,920,098 B2 | 3/2018 | Yoshida et al. |
| 10,065,995 B2 | 9/2018 | Yoshida et al. |
| 10,501,557 B2 | 12/2019 | Rodrigo et al. |
| 10,513,537 B2 * | 12/2019 | Rodrigo .................. C07K 1/22 |
| 10,654,887 B2 | 5/2020 | Rodrigo et al. |
| 10,703,774 B2 | 7/2020 | Forss et al. |
| 10,711,035 B2 * | 7/2020 | Rodrigo ............. B01J 20/28016 |
| 10,730,908 B2 * | 8/2020 | Forss ..................... C07K 14/31 |
| 10,918,971 B2 | 2/2021 | Hober |
| 10,995,113 B2 * | 5/2021 | Rodrigo .................. B01J 20/286 |
| 11,136,359 B2 | 10/2021 | Rodrigo et al. |
| 2005/0097625 A1 | 5/2005 | Meade et al. |
| 2005/0143566 A1 | 6/2005 | Hober |
| 2006/0194955 A1 | 8/2006 | Hober et al. |
| 2007/0207500 A1 | 9/2007 | Bian et al. |
| 2008/0167450 A1 | 7/2008 | Pan |
| 2008/0230478 A1 | 9/2008 | Johansson et al. |
| 2010/0221844 A1 | 9/2010 | Bian et al. |
| 2010/0256338 A1 | 10/2010 | Brinkmann et al. |
| 2010/0267932 A1 | 10/2010 | Eon-Duval et al. |
| 2011/0117605 A1 | 5/2011 | Tolstrup et al. |
| 2011/0144311 A1 | 6/2011 | Chmiellowski et al. |
| 2012/0071637 A1 | 3/2012 | Ambrosus et al. |
| 2012/0091063 A1 | 4/2012 | Bangtsson et al. |
| 2012/0148390 A1 | 6/2012 | Johansson et al. |
| 2012/0149875 A1 | 6/2012 | Johansson et al. |
| 2012/0208234 A1 | 8/2012 | Yoshida et al. |
| 2012/0238730 A1 | 9/2012 | Dong et al. |
| 2012/0263722 A1 | 10/2012 | Ghayur et al. |
| 2012/0283416 A1 | 11/2012 | Frauenschuh et al. |
| 2013/0096276 A1 | 4/2013 | Yoshida et al. |
| 2013/0096284 A1 | 4/2013 | Ishihara |
| 2013/0197197 A1 | 8/2013 | Eckermann et al. |
| 2013/0274451 A1 | 10/2013 | Bjorkman et al. |
| 2014/0018525 A1 | 1/2014 | Goklen et al. |
| 2014/0031522 A1 | 1/2014 | Li et al. |
| 2014/0094593 A1 | 4/2014 | Frauenschuh |
| 2014/0100356 A1 | 4/2014 | Yoshida et al. |
| 2014/0107315 A1 | 4/2014 | Yoshida et al. |
| 2014/0148390 A1 | 5/2014 | Haupts et al. |
| 2014/0154270 A1 | 6/2014 | Wang et al. |
| 2014/0155565 A1 | 6/2014 | Joehnck et al. |
| 2014/0228548 A1 | 8/2014 | Galperina |
| 2014/0242624 A1 | 8/2014 | Valliere-Douglass et al. |
| 2014/0251911 A1 | 9/2014 | Skudas |
| 2014/0303356 A1 | 10/2014 | Gramer et al. |
| 2014/0329995 A1 | 11/2014 | Johansson et al. |
| 2015/0009380 A1 | 1/2015 | Kobayashi et al. |
| 2015/0044209 A1 | 2/2015 | Brodt et al. |
| 2015/0080554 A1 | 3/2015 | Ander et al. |
| 2015/0093800 A1 | 4/2015 | Mahajan et al. |
| 2015/0133636 A1 | 5/2015 | Xenopoulos et al. |
| 2015/0140683 A1 | 5/2015 | Rueger et al. |
| 2015/0209445 A1 | 7/2015 | Maderna et al. |
| 2015/0210749 A1 | 7/2015 | Combs et al. |
| 2015/0218250 A1 | 8/2015 | Auer et al. |
| 2015/0268352 A1 | 9/2015 | Fischer et al. |
| 2016/0024147 A1 | 1/2016 | Tustian et al. |
| 2016/0053025 A1 | 2/2016 | Oh et al. |
| 2016/0083480 A1 | 3/2016 | Ng et al. |
| 2016/0090426 A1 | 3/2016 | Zhou et al. |
| 2016/0108084 A1 | 4/2016 | Gruber |
| 2016/0145340 A1 | 5/2016 | Borges et al. |
| 2016/0152668 A1 | 6/2016 | Hober |
| 2016/0152725 A1 | 6/2016 | Cheung et al. |
| 2016/0158377 A1 | 6/2016 | Ackler et al. |
| 2016/0159855 A1 | 6/2016 | Rodrigo et al. |
| 2016/0159857 A1 | 6/2016 | Rodrigo et al. |
| 2016/0159929 A1 | 6/2016 | Lee et al. |
| 2016/0166634 A1 | 6/2016 | Caplan et al. |
| 2016/0200797 A1 | 7/2016 | Hall et al. |
| 2016/0237124 A1 | 8/2016 | Qian et al. |
| 2016/0251395 A1 | 9/2016 | Davis et al. |
| 2016/0272710 A1 | 9/2016 | Hilden et al. |
| 2016/0289335 A1 | 10/2016 | Weisser et al. |
| 2016/0296648 A1 | 10/2016 | Chevallier et al. |
| 2016/0304617 A1 | 10/2016 | Damle et al. |
| 2016/0310612 A1 | 10/2016 | Lyon et al. |
| 2016/0311853 A1 | 10/2016 | Geierstanger et al. |
| 2016/0340443 A1 | 11/2016 | Rossi et al. |
| 2016/0362474 A1 | 12/2016 | Wang et al. |
| 2016/0362500 A1 | 12/2016 | Knoetgen |
| 2017/0043033 A1 | 2/2017 | Strop et al. |
| 2017/0081412 A1 | 3/2017 | Newman et al. |
| 2017/0088596 A1 | 3/2017 | Scheer et al. |
| 2017/0096485 A1 | 4/2017 | Bacac et al. |
| 2017/0114141 A1 | 4/2017 | Amann et al. |
| 2017/0121282 A1 | 5/2017 | Geierstanger et al. |
| 2017/0152298 A1 | 6/2017 | Banerjee et al. |
| 2017/0165370 A1 | 6/2017 | Govindan et al. |
| 2017/0182179 A1 | 6/2017 | Ackler et al. |
| 2017/0204199 A1 | 7/2017 | Sanches et al. |
| 2017/0216452 A1 | 8/2017 | Ma et al. |
| 2017/0218051 A1 | 8/2017 | Gnauer et al. |
| 2017/0226172 A1 | 8/2017 | Mohammadi et al. |
| 2017/0233453 A1 | 8/2017 | Zheng et al. |
| 2017/0233490 A1 | 8/2017 | Bossenmaier et al. |
| 2017/0247267 A1 | 8/2017 | Matsuzawa |
| 2017/0247417 A1 | 8/2017 | Chang et al. |
| 2017/0260265 A1 | 9/2017 | Duerr et al. |
| 2017/0260289 A1 | 9/2017 | Petersen et al. |
| 2017/0327534 A1 | 11/2017 | Rodrigo et al. |

(56) References Cited

U.S. PATENT DOCUMENTS

| | | |
|---|---|---|
| 2017/0334954 A1 | 11/2017 | Rodrigo et al. |
| 2019/0119318 A1 | 4/2019 | Rodrigo et al. |

FOREIGN PATENT DOCUMENTS

| | | |
|---|---|---|
| EP | 2557157 A1 | 2/2013 |
| EP | 2728000 A1 | 5/2014 |
| EP | 3050902 A1 | 8/2016 |
| EP | 3335789 A1 | 6/2018 |
| GB | 1608229.9 | 5/2016 |
| GB | 1608232.3 | 5/2016 |
| IN | 201717016314 A | 10/2017 |
| JP | 2500329 B2 | 5/1996 |
| JP | 2000-500649 A | 1/2000 |
| JP | 2006304633 A | 11/2006 |
| JP | 2010081866 A | 4/2010 |
| JP | 2016-079149 A | 5/2016 |
| JP | 2016-079153 A | 5/2016 |
| JP | 2017-037070 A | 2/2017 |
| WO | 88/09344 A1 | 12/1988 |
| WO | 03/080655 A1 | 10/2003 |
| WO | 2005075507 A1 | 8/2005 |
| WO | 2008/049106 A2 | 4/2008 |
| WO | 2010081866 A2 | 7/2010 |
| WO | 2011/107518 A1 | 9/2011 |
| WO | 2011118699 A1 | 9/2011 |
| WO | 2012/074463 A1 | 6/2012 |
| WO | 2012/083425 A1 | 6/2012 |
| WO | 2012/086660 A1 | 6/2012 |
| WO | 2012/087231 A1 | 6/2012 |
| WO | 2012/133349 A1 | 10/2012 |
| WO | 2013033517 A1 | 3/2013 |
| WO | 2013075849 A1 | 5/2013 |
| WO | 2013/081540 A1 | 6/2013 |
| WO | 2013/109302 A2 | 7/2013 |
| WO | 2013/147691 A1 | 10/2013 |
| WO | 2014/046278 A1 | 3/2014 |
| WO | 2014146350 | 9/2014 |
| WO | 2014159064 A1 | 10/2014 |
| WO | 2014186350 A1 | 11/2014 |
| WO | 2014192877 A1 | 12/2014 |
| WO | 2015005862 | 1/2015 |
| WO | 2015046473 A1 | 4/2015 |
| WO | 2015048330 A2 | 4/2015 |
| WO | 2015166072 A1 | 11/2015 |
| WO | 2016030791 A1 | 3/2016 |
| WO | 2015/005859 A1 | 5/2016 |
| WO | 2016079033 A1 | 5/2016 |
| WO | 2016079034 A1 | 5/2016 |
| WO | 2016097300 A1 | 6/2016 |
| WO | 2017011342 A1 | 1/2017 |
| WO | 2017036805 A1 | 3/2017 |
| WO | 2017050889 A1 | 3/2017 |
| WO | 2017194592 A1 | 11/2017 |
| WO | 2017194594 A1 | 11/2017 |

OTHER PUBLICATIONS

Minakuchi et al., "Remarkable Alkaline Stability of an Engineering Protein A as Immunoglobulin Affinity Ligand: C Doman having only one Amino Acid Substitution," Protein Science, 2013, 22:1230-1238.

Japanese Office Action for JP Application No. 2020-121312 dated Aug. 10, 2021 (13 pages, with English translation).

Japanese Office Action for JP Application No. 2018-558405 dated Mar. 29, 2021 (12 pages with English translation).

"Use of Sodium Hydroxide for Cleaning and Sanitization of Chromatography Media and systems," Application Note 18-1124-57 AI, 2014, https://www.cytivalifesciences.co.jp/catalog/pdf/18112457AI_AppNote_NaOHforCIP_SIP_final_1.pdf.

Indian Office Action for IN Application No. 20171701614 dated Sep. 7, 2021 (7 pages).

Non-Final Office Action for U.S. Appl. No. 16/682,855, dated Dec. 5, 2019, 14 pages.

PCT International Search Report and Written Opinion for PCT Application No. PCT/EP2017/061164, dated Sep. 5, 2017 (10 pages).

PCT International Search Report and Written Opinion for PCT Application No. PCT/EP2015/076642, dated Apr. 20, 2016 (19 pages).

Singapore Written Opinion and Search Report for SG Application No. 112017030353P, dated May 3, 2018 (11 pages).

Russian Office Action for RU Application No. 2017115345/10, dated Apr. 2, 2019 (English translation, 19 pages).

Berry et al., "Substitution of Cysteine for Selenocysteine in Type 1 Iodothyronine Deiodinase Reduces the Catalytic Efficiency of the Protein but Enhances its Translation," Endocrinology, 1992,131(4): 1848-1852.

Gasser et al., "Antibody Production with Yeasts and Filamentous Fungi: On the Road to Large Scale?", Biotechnol Lett, 2007, 29:201-212.

Pakula et al., "Genetic Analysis of Protein Stability and Function," Annu. Rev. Genet., 1989, 23:289-310.

European Office Action for EP Application No. 15797942.8 dated Jun. 25, 2019 (4 pages).

JP Office Action for JP Application No. 2017-525398 dated Nov. 11, 2019 (8 pages, English translation).

PCT International Search Report and Written Opinion for PCT Application No. PCT/EP2017/061162 dated Sep. 11, 2017 (24 pages).

Gel Filtration Principles and Methods, Pharmacia LKB Biotechnology 1991, pp. 6-13.

Australian Office Examination Report No. 1 for AU Application No. 2015348641 dated Dec. 17, 2019 (12 pages).

Bostrom et al, "Purification Systems Based on Bacterial Surface Proteins," Protein Purification, Intech, 2012, pp. 89-136, http://dx doi.org/10.5772/31078 (50 pages).

GB Search report for GB Application No. 1608229.9 dated Feb. 28, 2017 (10 pages).

GB Search Report for GB Application No. 1608232.3 dated Mar. 1, 2017 (10 pages).

Arshady, "Styrene Based Polymer Supports Developed by Suspension Polymerization," Chimica e L'Industria, 1988, 70(9):70-75.

Hjerten, "The Preparation of Agarose Spheres for Chromatography of Molecules and Particles," Biochim. Boiphys. Acta, 1964, 70:L393-398.

Bach et al., "Differential binding of heavy chain variable domain 3 antigen binding fragments to protein a chomatography resins," J Chromatography A, 2015, 1409: 60-69.

O'Seaghdha et al., "*Staphylococcus aureua* protein A binding to von Willebrand factor A1 domain is mediated by conserved IgG binding regions," FEBS J, 2006, 273, pp. 4831-4841.

Pakiman et al., "Comparison of Binding Capacity ad Affinity of Monoclonal Antibody towards Different Affinity Resins using Highthroughput Chromatography Method," J Appl Sci, 2012, 12, 11, pp. 1136-1141.

Weidle et al., "The intriguing options of multispecific antibody formats for treatment of cancer," Cancer Genom. Proteom, 2013, 10, pp. 1-18.

International Search Report for PCT Application No. PCT/EP2015/076639, dated Feb. 10, 2016 (12 pages).

International-type Search Report for ITS/SE2014/000256, dated May 13, 2015 (5 pages).

International Search Report and Written Opinion for PCT/EP2017/061159, dated Aug. 1, 2017 (14 pages).

European Search Report from EP Appl. No. 17 728 070.8, dated Jul. 18, 2019.

International Search Report for PCT Application No. PCT/EP2017/061160, dated Aug. 25, 2017, 5 pages.

International Search Report and Written Opinion Received for PCT Application No. PCT/EP2017/061158, dated Jul. 13, 2017, 15 pages.

Uhlen et al., "Complete Sequence of the Staphylococcal Gene Encoding Protein A", Journal of Biological Chemistry, vol. 259, No. 3, Feb. 10, 1984, pp. 1695-1702.

(56) References Cited

OTHER PUBLICATIONS

Hedhammar et al., "Protein Engineering Strategies for Selective Protein Purification", Chemical Engineering Technology, vol. 28, No. 11, 2005, pp. 1315-1325.

Hober et al., "Protein A Chromatography for Antibody Purification", Journal of Chromatograhy B, 848, 2007, pp. 40-47.

Altshul et al., "Basic Local Alignment Search Tool", Journal of Molecular Biology, vol. 215, 1990, pp. 403-410.

Gulich et al., "Stability towards alkaline conditions can be engineered into a protein ligand", Journal of Biotechology, vol. 80, 2000, pp. 169-178.

U.S. Appl. No. 15/367,640, filed Dec. 2, 2016, 52 pages.

Chinese Office Action for CN Application No. 201580062121.1 dated Jun. 23, 2020 (39 pages, with English translation).

Non-Final Office Action for U.S. Appl. No. 16/893,574 dated Oct. 6, 2020 (39 pages).

Mccaw et al. "Evaluation of a novel methacrylate-based protein A resin for the purificaiton of immunoglobulins and Fc-Fusion Proteins" Biotechnology Prog. 2014, 30(5) (Year: 2014), 12 pages.

Bowie, J., et al. "Deciphering the Message in Protein Sequences: Tolerance to Amino Acid Substitutions", Science, 1990, 247:4948, pp. 1306-1310.

Burgess, W.H., et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, 1990, 111, pp. 2129-2138.

Lazar, E., et al. "Transforming Growth Factor ex: Mutation of Aspartic Acid 47 and Leucine 48 Results in Different Biological Activities", Molecular and Cellular Biology, 1988, 8(3): 1247-1252.

Indian Office Action for IN Application No. 201847041236 dated Sep. 1, 2022 (7 pages).

Chinese Office Action for CN Application No. 201780028976.1 dated Sep. 3, 2021 (21 pages).

European Office Action for EP Application No. 17728070.8 dated Feb. 9, 2021 (4 pages).

International Search Report & Written Opinion for PCT Application No. PCT/EP201 7/061164 dated Aug. 30, 2017 (5 pages).

Japanese Office Action for JP Application No. 2017-525398 dated Nov. 19, 2019 (8 pages, with English translation).

Office Action Issued in Japanese Patent Application No. 2020-534551, dated Dec. 5, 2022 with English Summary (13 Pages).

\* cited by examiner

Alignment of Fc-binding domains

```
E           --- --------AQQ  NAFYQVLNMP  NLNADQRNGF  IQSLKDDPSQ
SANVLGEAQK  LNDSQAPK    51   (SEQ ID NO: 1)
D           ADA QQNKFNKDQQ   SAFYEILNMP  NLNEEQRNGF  IQSLKDDPSQ
STNVLGEAKK  LNESQAPK    61   (SEQ ID NO: 2)
A           --A DNN-FNKEQQ   NAFYEILNMP  NLNEEQRNGF  IQSLKDDPSQ
SANLLAEAKK  LNESQAPK    58   (SEQ ID NO: 3)
B           ---- ADNKFNKEQQ  NAFYEILHLP  NLNEEQRNGF  IQSLKDDPSQ
SANLLAEAKK  LNDAQAPK    58   (SEQ ID NO: 4)
C           ---- ADNKFNKEQQ  NAFYEILHLP  NLTEEQRNGF  IQSLKDDPSV
SKEILAEAKK  LNDAQAPK    58   (SEQ ID NO: 5)
Z           --- VDNKFNKEQQ   NAFYEILHLP  NLNEEQRNAF  IQSLKDDPSQ
SANLLAEAKK  LNDAQAPK    58   (SEQ ID NO: 6)
Zvar        ---- VDAKFDKEQQ  NAFYEILHLP  NLTEEQRNAF  IQSLKDDPSQ
SANLLAEAKK  LNDAQAPK    58   (SEQ ID NO: 7)

--- --------QQ   NAFYEILHLP  NLTEEQRNAF  IQSLKDDPSQ
SANLLAEAKK  LNDAQ---    47   (SEQ ID NO: 51)
            ---- ---------QQ NAFYEILHLP  NLTEEQRNGF  IQSLKDDPSV
SKEILAEAKK  LNDAQ---    47   (SEQ ID NO: 52)

Pos         1        10          20          30          40
50          58
```

FIG. 1

SEPARATION METHOD

CROSS-REFERENCE TO RELATED APPLICATIONS

This application is a continuation of U.S. application Ser. No. 15/348,699 filed on Nov. 10, 2016 and which is a continuation-in-part of U.S. application Ser. No. 15/282,367 filed on Sep. 30, 2016, the entire contents of which are hereby incorporated by reference herein.

SEQUENCE LISTING

The instant application contains a Sequence Listing which has been filed electronically in ASCII format and is hereby incorporated by reference in its entirety. Said ASCII copy, created on Jan. 28, 2020, is named 315715-US-1_34428-0439_SL.txt and is 81,017 bytes in size.

TECHNICAL FIELD OF THE INVENTION

The present invention relates to the field of affinity chromatography, and more specifically to mutated immunoglobulin-binding domains of Protein A, which are useful in affinity chromatography of immunoglobulins. The invention also relates to multimers of the mutated domains and to separation matrices containing the mutated domains or multimers.

BACKGROUND OF THE INVENTION

Immunoglobulins represent the most prevalent biopharmaceutical products in either manufacture or development worldwide. The high commercial demand for and hence value of this particular therapeutic market has led to the emphasis being placed on pharmaceutical companies to maximize the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species. These domains are commonly denoted as the E-, D-, A-, B- and C-domains.

Staphylococcal protein A (SpA) based reagents have due to their high affinity and selectivity found a widespread use in the field of biotechnology, e.g. in affinity chromatography for capture and purification of antibodies as well as for detection or quantification. At present, SpA-based affinity medium probably is the most widely used affinity medium for isolation of monoclonal antibodies and their fragments from different samples including industrial cell culture supernatants. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A-SEPHAROSE™, GE Healthcare). More specifically, the genetic manipulation performed in the commercial recombinant protein A product is aimed at facilitating the attachment thereof to a support and at increasing the productivity of the ligand.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitizing agent is NaOH, and the concentration thereof can range from 0.1 up to e.g. 1 M, depending on the degree and nature of contamination. This strategy is associated with exposing the matrix to solutions with pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focused on the development of engineered protein ligands that exhibit an improved capacity to withstand alkaline pH-values. For example, Gülich et al. (Susanne Gülich, Martin Linhult, Per-Ake Nygren, Mathias Uhlén, Sophia Hober, Journal of Biotechnology 80 (2000), 169-178) suggested protein engineering to improve the stability properties of a Streptococcal albumin-binding domain (ABD) in alkaline environments. Gülich et al. created a mutant of ABD, wherein all the four asparagine residues have been replaced by leucine (one residue), aspartate (two residues) and lysine (one residue). Further, Gülich et al. report that their mutant exhibits a target protein binding behavior similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work shows that changes can also be made to protein A (SpA) to effect similar properties. US patent application publication US 2005/0143566, which is hereby incorporated by reference in its entirety, discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844, incorporated by reference in its entirety). The authors show that when these mutated proteins are used as affinity ligands, the separation media as expected can better withstand cleaning procedures using alkaline agents. Further mutations of protein A domains with the purpose of increasing the alkali stability have also been published in U.S. Pat. No. 8,329,860, JP 2006304633A, U.S. Pat. No. 8,674,073, US 2010/0221844, US 2012/0208234, U.S. Pat. No. 9,051,375, US 2014/0031522, US 2013/0274451 and WO 2014/146350, all of which are hereby incorporated by reference in their entireties. However, the currently available mutants are still sensitive to alkaline pH and the NaOH concentration during cleaning is usually limited to 0.1 M, which means that complete cleaning is difficult to achieve. Higher NaOH concentrations, which would improve the cleaning, lead to unacceptable capacity losses.

There is thus still a need in this field to obtain a separation matrix containing protein ligands having a further improved stability towards alkaline cleaning procedures. There is also a need for such separation matrices with an improved binding capacity to allow for economically efficient purification of therapeutic antibodies.

SUMMARY OF THE INVENTION

One aspect of the invention is to provide a polypeptide with improved alkaline stability. This is achieved with an Fc-binding polypeptide comprising a mutant of a parental Fc-binding domain of *Staphylococcus* Protein A (SpA), as defined by, or having at least 80% such as at least 90%, 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO: 51 or SEQ ID NO: 52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine. Alternatively, the polypeptide comprises a sequence as defined by, or having at least 80% or at least 90%, 95% or 98% identity to SEQ ID NO: 53.

(SEQ ID NO: 53)
$X_1Q$ $X_2AFYEILX_3LP$ $NLTEEQRX_4X_5F$ $IX_6X_7LKDX_8PSX_9$ $SX_{10}X_{11}X_{12}LAEAKX_{13}$ $X_{14}NX_{15}AQ$ wherein individually of each other:
$X_1$=A or Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K
$X_6$=Q or E
$X_7$=S or K
$X_8$=E or D
$X_9$=Q or V or is deleted
$X_{10}$=K, R or A or is deleted
$X_{11}$=A, E or N or is deleted
$X_{12}$=I or L
$X_{13}$=K or R
$X_{14}$=L or Y
$X_{15}$=D, F, Y, W, K or R One advantage is that the alkaline stability is improved over the parental polypeptides, with a maintained highly selective binding towards immunoglobulins and other Fc-containing proteins.

A second aspect of the invention is to provide a multimer with improved alkaline stability, comprising a plurality of polypeptides. This is achieved with a multimer of the polypeptide disclosed above.

A third aspect of the invention is to provide a nucleic acid or a vector encoding a polypeptide or multimer with improved alkaline stability. This is achieved with a nucleic acid or vector encoding a polypeptide or multimer as disclosed above.

A fourth aspect of the invention is to provide an expression system capable of expressing a polypeptide or multimer with improved alkaline stability. This is achieved with an expression system comprising a nucleic acid or vector as disclosed above.

A fifth aspect of the invention is to provide a separation matrix capable of selectively binding immunoglobulins and other Fc-containing proteins and exhibiting an improved alkaline stability. This is achieved with a separation matrix comprising at least 11 mg/ml Fc-binding ligands covalently coupled to a porous support, wherein:
a) the ligands comprise multimers of alkali-stabilized Protein A domains,
b) the porous support comprises cross-linked polymer particles having a volume-weighted median diameter (d50,v) of 56-70 micrometers and a dry solids weight of 55-80 mg/ml. Alternatively, it is achieved with a separation matrix comprising at least 15 mg/ml Fc-binding ligands covalently coupled to a porous support, wherein said ligands comprise multimers of alkali-stabilized Protein A domains.

One advantage is that a high dynamic binding capacity is provided. A further advantage is that a high degree of alkali stability is achieved.

A sixth aspect of the invention is to provide an efficient and economical method of isolating an immunoglobulin or other Fc-containing protein. This is achieved with a method comprising the steps of:
a) contacting a liquid sample comprising an immunoglobulin with a separation matrix as disclosed above,
b) washing the separation matrix with a washing liquid,
c) eluting the immunoglobulin from the separation matrix with an elution liquid, and
d) cleaning the separation matrix with a cleaning liquid.

Further suitable embodiments of the invention are described in the dependent claims. Co-pending applications PCT EP2015/076639, PCT EP2015/076642, GB 1608229.9 and GB 1608232.3 are hereby incorporated by reference in their entireties.

Definitions

The terms "antibody" and "immunoglobulin" are used interchangeably herein, and are understood to include also fragments of antibodies, fusion proteins comprising antibodies or antibody fragments and conjugates comprising antibodies or antibody fragments.

The terms an "Fc-binding polypeptide" and "Fc-binding protein" mean a polypeptide or protein respectively, capable of binding to the crystallisable part (Fc) of an antibody and includes e.g. Protein A and Protein G, or any fragment or fusion protein thereof that has maintained said binding property.

The term "linker" herein means an element linking two polypeptide units, monomers or domains to each other in a multimer.

The term "spacer" herein means an element connecting a polypeptide or a polypeptide multimer to a support.

The term "% identity" with respect to comparisons of amino acid sequences is determined by standard alignment algorithms such as, for example, Basic Local Alignment Tool (BLAST™) described in Altshul et al. (1990) J. Mol. Biol., 215: 403-410. A web-based software for this is freely available from the US National Library of Medicine. Here, the algorithm "blastp (protein-protein BLAST)" is used for alignment of a query sequence with a subject sequence and determining i.a. the % identity.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

BRIEF DESCRIPTION OF FIGURES

FIG. 1 shows an alignment of the Fc-binding domains as defined by SEQ ID NO:1-7 and 51-52.

DETAILED DESCRIPTION OF EMBODIMENTS

Figure 2:
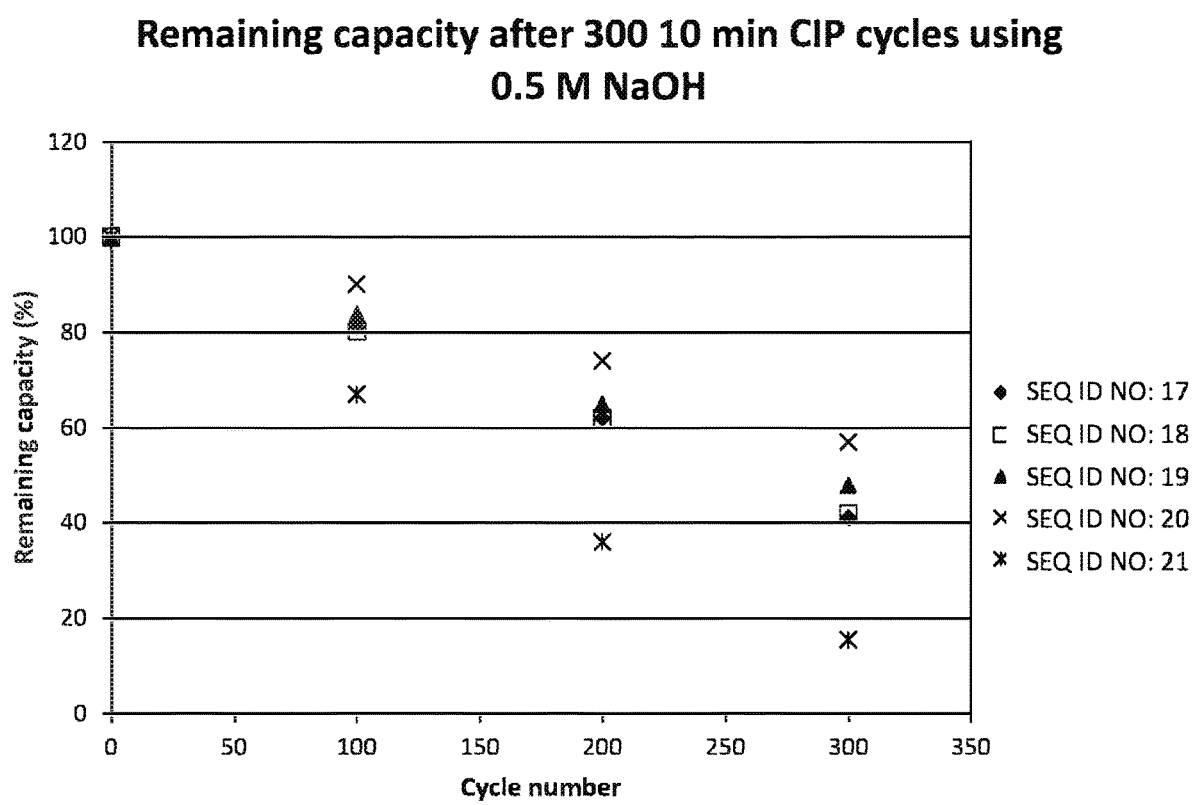
FIG. 2 shows results from Example 2 for the alkali stability of parental and mutated tetrameric Zvar (SEQ ID NO 7) polypeptide variants coupled to an SPR biosensor chip.

In one aspect the present invention discloses an Fc-binding polypeptide, which comprises, or consists essentially of, a mutant of an Fc-binding domain of *Staphylococcus* Protein A (SpA), as defined by, or having at least 90%, at least 95% or at least 98% identity to, SEQ ID NO: 1 (E-domain), SEQ ID NO: 2 (D-domain), SEQ ID NO:3 (A-domain), SEQ ID NO:22 (variant A-domain), SEQ ID NO: 4 (B-domain), SEQ ID NO: 5 (C-domain), SEQ ID NO:6 (Protein Z), SEQ ID NO:7 (Zvar), SEQ ID NO: 51 (Zvar without the linker region amino acids 1-8 and 56-58) or SEQ ID NO: 52 (C-domain without the linker region amino acids 1-8 and 56-58) as illustrated in FIG. 1, wherein at least the asparagine (or serine, in the case of SEQ ID NO 2) residue at the position* corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine. Protein Z (SEQ ID NO:6) is a mutated B-domain as disclosed in U.S. Pat. No. 5,143,844, hereby incorporated by reference in its entirety, while SEQ ID NO 7 denotes a further mutated variant of Protein Z, here called Zvar, with the mutations N3A,N6D,N23T. SEQ ID NO:22 is a natural variant of the A-domain in Protein A from *Staphylococcus aureus* strain N315, having an A46S mutation, using the position terminology of FIG. 1. The mutation of N11 in these domains confers an improved alkali stability in comparison with the parental domain/polypeptide, without impairing the immunoglobulin-binding properties. Hence, the polypeptide can also be described as an Fc- or immunoglobulin-binding polypeptide, or alternatively as an Fc- or immunoglobulin-binding polypeptide unit.

*Throughout this description, the amino acid residue position numbering convention of FIG. 1 is used, and the position numbers are designated as corresponding to those in SEQ ID NO 4-7. This applies also to multimers, where the position numbers designate the positions in the polypeptide units or monomers according to the convention of FIG. 1.

(truncated Zvar)
SEQ ID NO: 51
QQ NAFYEILHLP NLTEEQRNAF IQSLKDDPSQ SANLLAEAKK

LNDAQ (truncated C domain)
SEQ ID NO: 52
QQ NAFYEILHLP NLTEEQRNGF IQSLKDDPSV SKEILAEAKK

LNDAQ

In alternative language, the invention discloses an Fc-binding polypeptide which comprises a sequence as defined by, or having at least 90%, at least 95% or at least 98% identity to SEQ ID NO: 53.

SEQ ID NO: 53
$X_1Q$ $X_2AFYEILX_3LP$ $NLTEEQRX_4X_5F$ $IX_6X_7LKDX_8PSX_9$ $SX_{10}X_{11}X_{12}LAEAKX_{13}$ $X_{14}NX_{15}AQ$ wherein individually of each other:
$X_1$=A, Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K, such as S, Y, Q, T, N, F, L, W, I, M, V, D, E, H, R or K
$X_6$=Q or E
$X_7$=S or K
$X_8$=E or D
$X_9$=Q, V or is deleted
$X_{10}$=K, R, A or is deleted
$X_{11}$=A, E, N or is deleted
$X_{12}$=I or L $X_{13}$=K or R $X_{14}$=L or Y $X_{15}$=D, F, Y, W, K or R Specifically, the amino acid residues in SEQ ID NO: 53 may individually of each other be:

$X_1$=A or is deleted $X_2$=E $X_3$=H $X_4$=N $X_6$=Q $X_7$=S $X_8$=D $X_9$=V or is deleted $X_{10}$=K or is deleted $X_{11}$=A or is deleted $X_{12}$=I $X_{13}$=K $X_{14}$=L.

In certain embodiments, the amino acid residues in SEQ ID NO: 53 may be: $X_1$=A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L. In some embodiments $X_2$=E, $X_3$=H, $X_4$=N, $X_5$=A, $X_6$=Q, $X_7$=S, $X_8$=D, $X_{12}$=I, $X_{13}$=K, $X_{14}$=L and $X_{15}$=D and one or more of $X_1$, $X_9$, $X_{10}$ and $X_{11}$ is deleted. In further embodiments, $X_1$=A, $X_2$=E, $X_3$=H, $X_4$=N, $X_5$=S, Y, Q, T, N, F, L, W, I, M, V, D, E, H, R or K, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D, or alternatively $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=F, Y, W, K or R.

The N11 ($X_2$) mutation (e.g. a N11E or N11K mutation) may be the only mutation or the polypeptide may also comprise further mutations, such as substitutions in at least one of the positions corresponding to positions 3, 6, 9, 10, 15, 18, 23, 28, 29, 32, 33, 36, 37, 40, 42, 43, 44, 47, 50, 51, 55 and 57 in SEQ ID NO:4-7. In one or more of these positions, the original amino acid residue may e.g. be substituted with an amino acid which is not asparagine, proline or cysteine. The original amino acid residue may e.g. be substituted with an alanine, a valine, a threonine, a serine, a lysine, a glutamic acid or an aspartic acid. Further, one or more amino acid residues may be deleted, e.g. from positions 1-6 and/or from positions 56-58.

In some embodiments, the amino acid residue at the position corresponding to position 9 in SEQ ID NO:4-7 ($X_1$) is an amino acid other than glutamine, asparagine, proline or cysteine, such as an alanine or it can be deleted. The combination of the mutations at positions 9 and 11 provides particularly good alkali stability, as shown by the examples. In specific embodiments, in SEQ ID NO: 7 the amino acid residue at position 9 is an alanine and the amino acid residue at position 11 is a lysine or glutamic acid, such as a lysine. Mutations at position 9 are also discussed in copending application PCT/SE2014/050872, which is hereby incorporated by reference in its entirety.

In some embodiments, the amino acid residue at the position corresponding to position 50 in SEQ ID NO:4-7 ($X_{13}$) is an arginine or a glutamic acid.

In certain embodiments, the amino acid residue at the position corresponding to position 3 in SEQ ID NO:4-7 is an alanine and/or the amino acid residue at the position corresponding to position 6 in SEQ ID NO:4-7 is an aspartic acid. One of the amino acid residues at positions 3 and 6 may be an asparagine and in an alternative embodiment both amino acid residues at positions 3 and 6 may be asparagines.

In some embodiments the amino acid residue at the position corresponding to position 43 in SEQ ID NO:4-7 ($X_{11}$) is an alanine or a glutamic acid, such as an alanine or it can be deleted. In specific embodiments, the amino acid residues at positions 9 and 11 in SEQ ID NO: 7 are alanine and lysine/glutamic acid respectively, while the amino acid residue at position 43 is alanine or glutamic acid.

In certain embodiments the amino acid residue at the position corresponding to position 28 in SEQ ID NO:4-7 ($X_5$) is an alanine or an asparagine, such as an alanine.

In some embodiments the amino acid residue at the position corresponding to position 40 in SEQ ID NO:4-7 ($X_9$) is selected from the group consisting of asparagine, alanine, glutamic acid and valine, or from the group consisting of glutamic acid and valine or it can be deleted. In specific embodiments, the amino acid residues at positions 9 and 11 in SEQ ID NO: 7 are alanine and glutamic acid respectively, while the amino acid residue at position 40 is valine. Optionally, the amino acid residue at position 43 may then be alanine or glutamic acid.

In certain embodiments, the amino acid residue at the position corresponding to position 42 in SEQ ID NO:4-7 ($X_{10}$) is an alanine, lysine or arginine or it can be deleted.

In some embodiments the amino acid residue at the position corresponding to position 18 in SEQ ID NO:4-7 ($X_3$) is a lysine or a histidine, such as a lysine.

In certain embodiments the amino acid residue at the position corresponding to position 33 in SEQ ID NO:4-7 ($X_7$) is a lysine or a serine, such as a lysine.

In some embodiments the amino acid residue at the position corresponding to position 37 in SEQ ID NO:4-7 ($X_8$) is a glutamic acid or an aspartic acid, such as a glutamic acid.

In certain embodiments the amino acid residue at the position corresponding to position 51 in SEQ ID NO:4-7 ($X_{14}$) is a tyrosine or a leucine, such as a tyrosine.

In some embodiments, the amino acid residue at the position corresponding to position 44 in SEQ ID NO:4-7 ($X_{12}$) is a leucine or an isoleucine. In specific embodiments, the amino acid residues at positions 9 and 11 in SEQ ID NO: 7 are alanine and lysine/glutamic acid respectively, while the amino acid residue at position 44 is isoleucine. Optionally, the amino acid residue at position 43 may then be alanine or glutamic acid.

In some embodiments, the amino acid residues at the positions corresponding to positions 1, 2, 3 and 4 or to positions 3, 4, 5 and 6 in SEQ ID NO: 4-7 have been deleted. In specific variants of these embodiments, the parental polypeptide is the C domain of Protein A (SEQ ID NO: 5). The effects of these deletions on the native C domain are described in U.S. Pat. Nos. 9,018,305 and 8,329,860, which are hereby incorporated by reference in their entireties.

In certain embodiments, the mutation in SEQ ID NO 4-7, such as in SEQ ID NO 7, is selected from the group consisting of: N11K; N11E; N11Y; N11T; N11F; N11L; N11W; N11I; N11M; N11V; N11A; N11H; N11R; N11E,Q32A; N11E,Q32E,Q40E; N11E,Q32E,K50R; Q9A,N11E,N43A; Q9A,N11E,N28A,N43A; Q9A,N11E,Q40V,A42K,N43E,L44I; Q9A,N11E,Q40V,A42K,N43A,L44I; N11K, H18K,S33K,D37E,A42R,N43A,L44I,K50R,L51Y; Q9A, N11E,N28A,Q40V,A42K,N43A,L44I; Q9A,N11K,H18K, S33K,D37E,A42R,N43A,L44I,K50R,L51Y; N11K, H18K, D37E, A42R, N43A, L44I; Q9A, N11K, H18K, D37E, A42R, N43A, L44I; Q9A, N11K, H18K, D37E, A42R, N43A, L44I, K50R; Q9A,N11K,H18K,D37E,A42R; Q9A, N11E,D37E,Q40V,A42K,N43A,L44I and Q9A,N11E, D37E,Q40V,A42R,N43A,L44I. These mutations provide particularly high alkaline stabilities. The mutation in SEQ ID NO 4-7, such as in SEQ ID NO 7, can also be selected from the group consisting of N11K; N11Y; N11F; N11L; N11W; N11I; N11M; N11V; N11A; N11H; N11R; Q9A, N11E,N43A; Q9A,N11E,N28A,N43A; Q9A,N11E,Q40V, A42K,N43E,L44I; Q9A,N11E,Q40V,A42K,N43A,L44I; Q9A,N11E,N28A,Q40V,A42K,N43A,L44I; N11K,H18K, S33K,D37E,A42R,N43A,L44I,K50R,L51Y; Q9A,N11K, H18K,S33K,D37E,A42R,N43A,L44I,K50R,L51Y; N11K, H18K, D37E, A42R, N43A, L44I; Q9A, N11K, H18K, D37E, A42R, N43A, L44I and Q9A, N11K, H18K, D37E, A42R, N43A, L44I, K50R.

In some embodiments, the polypeptide comprises or consists essentially of a sequence defined by or having at least 90%, 95% or 98% identity to an amino acid sequence selected from the group consisting of: SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 23, SEQ ID NO 24, SEQ ID NO 25, SEQ ID NO 26, SEQ ID NO 27, SEQ ID NO 28, SEQ ID NO 29, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49 and SEQ ID NO: 50. It may e.g. comprise or consist essentially of a sequence defined by or having at least 90%, 95% or 98% identity to an amino acid sequence selected from the group consisting of: SEQ ID NO 8, SEQ ID NO 9, SEQ ID NO 10, SEQ ID NO 11, SEQ ID NO 16, SEQ ID NO 23, SEQ ID NO 24, SEQ ID NO 25, SEQ ID NO 26, SEQ ID NO 27, SEQ ID NO 28 and SEQ ID NO 29. It can also comprise or consist essentially of a sequence defined by or having at least 90%, 95% or 98% identity to an amino acid sequence selected from the group consisting of: SEQ ID NO 8, SEQ ID NO 9, SEQ ID NO 10, SEQ ID NO 11, SEQ ID NO 16, SEQ ID NO 23, SEQ ID NO 24, SEQ ID NO 25, SEQ ID NO 27, SEQ ID NO 28, SEQ ID NO 38, SEQ ID NO 40; SEQ ID NO 41; SEQ ID NO 42; SEQ NO 43, SEQ ID NO 44, SEQ ID NO 45, SEQ ID NO 46, SEQ ID NO 47 and SEQ ID NO 48.

In certain embodiments, the polypeptide comprises or consists essentially of a sequence defined by or having at least 90%, 95% or 98% identity to an amino acid sequence selected from the group consisting of SEQ ID NO: 54-70. comprises or consists essentially of a sequence defined by or having at least 90%, 95% or 98% identity to an amino acid sequence selected from the group consisting of SEQ ID NO 71-75, or it may comprise or consist essentially of a sequence defined by or having at least 90%, 95% or 98% identity to an amino acid sequence selected from the group consisting of SEQ ID NO 76-79. It may further comprise or consist essentially of a sequence defined by or having at least 90%, 95% or 98% identity to an amino acid sequence selected from the group consisting of SEQ ID NO 89-95.

The polypeptide may e.g. be defined by a sequence selected from the groups above or from subsets of these groups, but it may also comprise additional amino acid residues at the N- and/or C-terminal end, e.g. a leader sequence at the N-terminal end and/or a tail sequence at the C-terminal end.

```
Zvar(Q9A,N11E,N43A)
                                            SEQ ID NO 8
VDAKFDKEAQ EAFYEILHLP NLTEEQRNAF IQSLKDDPSQ
SAALLAEAKK LNDAQAPK Zvar(Q9A,N11E,N28A,N43A)
                                            SEQ ID NO 9
VDAKFDKEAQ EAFYEILHLP NLTEEQRAAF IQSLKDDPSQ
SAALLAEAKK LNDAQAPK Zvar(Q9A,N11E,Q40V,A42K,N43E,L44I)
                                            SEQ ID NO 10
VDAKFDKEAQ EAFYEILHLP NLTEEQRNAF IQSLKDDPSV
SKEILAEAKK LNDAQAPK Zvar(Q9A,N11E,Q40V,A42K,N43A,L44I)
                                            SEQ ID NO 11
VDAKFDKEAQ EAFYEILHLP NLTEEQRNAF IQSLKDDPSV
SKAILAEAKK LNDAQAPK Zvar(N11E,Q32A)
                                            SEQ ID NO 12
VDAKFDKEQQ EAFYEILHLP NLTEEQRNAF IASLKDDPSQ
SANLLAEAKK LNDAQAPK Zvar(N11E)
                                            SEQ ID NO 13
VDAKFDKEQQ EAFYEILHLP NLTEEQRNAF IQSLKDDPSQ
SANLLAEAKK LNDAQAPK Zvar(N11E,Q32E,Q40E)
                                            SEQ ID NO 14
VDAKFDKEQQ EAFYEILHLP NLTEEQRNAF IESLKDDPSE
SANLLAEAKK LNDAQAPK Zvar(N11E,Q32E,K50R)
                                            SEQ ID NO 15
VDAKFDKEQQ EAFYEILHLP NLTEEQRNAF IESLKDDPSQ
SANLLAEAKR LNDAQAPK Zvar(N11K)
                                            SEQ ID NO 16
VDAKFDKEQQ KAFYEILHLP NLTEEQRNAF IQSLKDDPSQ
SANLLAEAKK LNDAQAPK Zvar(N11K,H18K,S33K,D37E,A42R,N43A,L44I,K50R,L51Y)
                                            SEQ ID NO 23
VDAKFDKEQQ KAFYEILKLP NLTEEQRNAF IQKLKDEPSQ
SRAILAEAKR YNDAQAPK Zvar(Q9A,N11E,N28A,Q40V,A42K,N43A,L44I)
                                            SEQ ID NO 24
VDAKFDKEAQ EAFYEILHLP NLTEEQRAAF IQSLKDDPSV
SKAILAEAKK LNDAQAPK Zvar(Q9A,N11K,H18K,S33K,D37E,A42R,N43A,L44I,K50R,
L51Y)
                                            SEQ ID NO 25
VDAKFDKEAQ KAFYEILKLP NLTEEQRAAF IQKLKDEPSQ
SRAILAEAKR YNDAQAPK Zvar(N11K,H18K,D37E,A42R,N43A,L44I)
                                            SEQ ID NO 26
VDAKFDKEQQ KAFYEILKLP NLTEEQRNAF IQSLKDEPSQ
SRAILAEAKK LNDAQAPK Zvar(Q9A,N11K,H18K,D37E,A42R,N43A,L44I)
                                            SEQ ID NO 27
VDAKFDKEAQ KAFYEILKLP NLTEEQRNAF IQSLKDEPSQ
SRAILAEAKK LNDAQAPK
```

Zvar(Q9A,N11K,H18K,D37E,A42R,N43A,L44I,K50R)
SEQ ID NO 28
VDAKFDKEAQ KAFYEILKLP NLTEEQRNAF IQSLKDEPSQ
SRAILAEAKR LNDAQAPK Zvar(Q9A,N11K,H18K,D37E,A42R)
SEQ ID NO 29
VDAKFDKEAQ KAFYEILKLP NLTEEQRNAF IQSLKDEPSQ
SRNLLAEAKK LNDAQAPK B(Q9A,N11E,Q40V,A42K,N43A,L44I)
SEQ ID NO 36
ADNKFNKEAQ EAFYEILHLP NLNEEQRNGF IQSLKDDPSV
SKAILAEAKK LNDAQAPK C(Q9A,N11E,E43A)
SEQ ID NO 37
ADNKFNKEAQ EAFYEILHLP NLTEEQRNGF IQSLKDDPSV
SKAILAEAKK LNDAQAPK Zvar(N11Y)
SEQ ID NO 38
VDAKFDKEQQ YAFYEILHLP NLTEEQRNAF IQSLKDDPSQ
SANLLAEAKK LNDAQAPK Zvar(N11T)
SEQ ID NO 39
VDAKFDKEQQ TAFYEILHLP NLTEEQRNAF IQSLKDDPSQ
SANLLAEAKK LNDAQAPK Zvar(N11F)
SEQ ID NO 40
VDAKFDKEQQ FAFYEILHLP NLTEEQRNAF IQSLKDDPSQ
SANLLAEAKK LNDAQAPK Zvar(N11L)
SEQ ID NO 41
VDAKFDKEQQ LAFYEILHLP NLTEEQRNAF IQSLKDDPSQ
SANLLAEAKK LNDAQAPK Zvar(N11W)
SEQ ID NO 42
VDAKFDKEQQ WAFYEILHLP NLTEEQRNAF IQSLKDDPSQ
SANLLAEAKK LNDAQAPK Zvar(N11I)
SEQ ID NO 43
VDAKFDKEQQ IAFYEILHLP NLTEEQRNAF IQSLKDDPSQ
SANLLAEAKK LNDAQAPK Zvar(N11M)
SEQ ID NO 44
VDAKFDKEQQ MAFYEILHLP NLTEEQRNAF IQSLKDDPSQ
SANLLAEAKK LNDAQAPK Zvar(N11V)
SEQ ID NO 45
VDAKFDKEQQ VAFYEILHLP NLTEEQRNAF IQSLKDDPSQ
SANLLAEAKK LNDAQAPK Zvar(N11A)
SEQ ID NO 46
VDAKFDKEQQ AAFYEILHLP NLTEEQRNAF IQSLKDDPSQ
SANLLAEAKK LNDAQAPK Zvar(N11H)
SEQ ID NO 47
VDAKFDKEQQ HAFYEILHLP NLTEEQRNAF IQSLKDDPSQ
SANLLAEAKK LNDAQAPK Zvar(N11R)
SEQ ID NO 48
VDAKFDKEQQ RAFYEILHLP NLTEEQRNAF IQSLKDDPSQ
SANLLAEAKK LNDAQAPK Zvar(Q9A,N11E,D37E,Q40V,A42K,N43A,L44I)
SEQ ID NO 49
VDAKFDKEAQ EAFYEILHLP NLTEEQRNAF IQSLKDEPSV
SKAILAEAKK LNDAQAPK Zvar(Q9A,N11E,D37E,Q40V,A42R,N43A,L44I)
SEQ ID NO: 50
VDAKFDKEAQ EAFYEILHLP NLTEEQRNAF IQSLKDEPSV
SRAILAEAKK LNDAQAPK Zvar(Q9A,N11E,A29G,Q40V,A42K,N43A,L44I)
SEQ ID NO: 54
VDAKFDKEAQ EAFYEILHLP NLTEEQRNGF IQSLKDDPSV
SKAILAEAKK LNDAQAPK Zvar(Q9A,N11E,A29S,Q40V,A42K,N43A,L44I)
SEQ ID NO: 55
VDAKFDKEAQ EAFYEILHLP NLTEEQRNSF IQSLKDDPSV
SKAILAEAKK LNDAQAPK Zvar(Q9A,N11E,A29Y,Q40V,A42K,N43A,L44I)
SEQ ID NO: 56
VDAKFDKEAQ EAFYEILHLP NLTEEQRNYF IQSLKDDPSV
SKAILAEAKK LNDAQAPK Zvar(Q9A,N11E,A29Q,Q40V,A42K,N43A,L44I)
SEQ ID NO: 57
VDAKFDKEAQ EAFYEILHLP NLTEEQRNQF IQSLKDDPSV
SKAILAEAKK LNDAQAPK Zvar(Q9A,N11E,A29T,Q40V,A42K,N43A,L44I)
SEQ ID NO: 58
VDAKFDKEAQ EAFYEILHLP NLTEEQRNTF IQSLKDDPSV
SKAILAEAKK LNDAQAPK Zvar(Q9A,N11E,A29N,Q40V,A42K,N43A,L44I)
SEQ ID NO: 59
VDAKFDKEAQ EAFYEILHLP NLTEEQRNNF IQSLKDDPSV
SKAILAEAKK LNDAQAPK Zvar(Q9A,N11E,A29F,Q40V,A42K,N43A,L44I)
SEQ ID NO 60
VDAKFDKEAQ EAFYEILHLP NLTEEQRNFF IQSLKDDPSV
SKAILAEAKK LNDAQAPK Zvar(Q9A,N11E,A29L,Q40V,A42K,N43A,L44I)
SEQ ID NO 61
VDAKFDKEAQ EAFYEILHLP NLTEEQRNLF IQSLKDDPSV
SKAILAEAKK LNDAQAPK Zvar(Q9A,N11E,A29W,Q40V,A42K,N43A,L44I)
SEQ ID NO 62
VDAKFDKEAQ EAFYEILHLP NLTEEQRNWF IQSLKDDPSV
SKAILAEAKK LNDAQAPK Zvar(Q9A,N11E,A29I,Q40V,A42K,N43A,L44I)
SEQ ID NO 63
VDAKFDKEAQ EAFYEILHLP NLTEEQRNIF IQSLKDDPSV

SKAILAEAKK LNDAQAPK

Zvar(Q9A,N11E,A29M,Q40V,A42K,N43A,L44I)
SEQ ID NO 64
VDAKFDKEAQ EAFYEILHLP NLTEEQRNMF IQSLKDDPSV

SKAILAEAKK LNDAQAPK

Zvar(Q9A,N11E,A29V,Q40V,A42K,N43A,L44I)
SEQ ID NO 65
VDAKFDKEAQ EAFYEILHLP NLTEEQRNVF IQSLKDDPSV

SKAILAEAKK LNDAQAPK

Zvar(Q9A,N11E,A29D,Q40V,A42K,N43A,L44I)
SEQ ID NO 66
VDAKFDKEAQ EAFYEILHLP NLTEEQRNDF IQSLKDDPSV

SKAILAEAKK LNDAQAPK

Zvar(Q9A,N11E,A29E,Q40V,A42K,N43A,L44I)
SEQ ID NO 67
VDAKFDKEAQ EAFYEILHLP NLTEEQRNEF IQSLKDDPSV

SKAILAEAKK LNDAQAPK

Zvar(Q9A,N11E,A29H,Q40V,A42K,N43A,L44I)
SEQ ID NO 68
VDAKFDKEAQ EAFYEILHLP NLTEEQRNHF IQSLKDDPSV

SKAILAEAKK LNDAQAPK

Zvar(Q9A,N11E,A29R,Q40V,A42K,N43A,L44I)
SEQ ID NO 69
VDAKFDKEAQ EAFYEILHLP NLTEEQRNRF IQSLKDDPSV

SKAILAEAKK LNDAQAPK

Zvar(Q9A,N11E,A29K,Q40V,A42K,N43A,L44I)
SEQ ID NO 70
VDAKFDKEAQ EAFYEILHLP NLTEEQRNKF IQSLKDDPSV

SKAILAEAKK LNDAQAPK

Zvar(Q9A,N11E,Q40V,A42K,N43A,L44I,D53F)
SEQ ID NO 71
VDAKFDKEAQ EAFYEILHLP NLTEEQRNAF IQSLKDDPSV

SKAILAEAKK LNFAQAPK

Zvar(Q9A,N11E,Q40V,A42K,N43A,L44I,D53Y)
SEQ ID NO 72
VDAKFDKEAQ EAFYEILHLP NLTEEQRNAF IQSLKDDPSV

SKAILAEAKK LNYAQAPK

Zvar(Q9A,N11E,Q40V,A42K,N43A,L44I,D53W)
SEQ ID NO 73
VDAKFDKEAQ EAFYEILHLP NLTEEQRNAF IQSLKDDPSV

SKAILAEAKK LNWAQAPK

Zvar(Q9A,N11E,Q40V,A42K,N43A,L44I,D53K)
SEQ ID NO 74
VDAKFDKEAQ EAFYEILHLP NLTEEQRNAF IQSLKDDPSV

SKAILAEAKK LNKAQAPK

Zvar(Q9A,N11E,Q40V,A42K,N43A,L44I,D53R)
SEQ ID NO 75
VDAKFDKEAQ EAFYEILHLP NLTEEQRNAF IQSLKDDPSV

SKAILAEAKK LNRAQAPK

Zvar(Q9del,N11E,Q40V,A42K,N43A,L44I)
SEQ ID NO 76
VDAKFDKE_Q EAFYEILHLP NLTEEQRNAF IQSLKDDPSV

SKAILAEAKK LNDAQAPK

Zvar(Q9A,N11E,Q40del,A42K,N43A,L44I)
SEQ ID NO 77
VDAKFDKEAQ EAFYEILHLP NLTEEQRNAF IQSLKDDPS_

SKAILAEAKK LNDAQAPK

Zvar(Q9A,N11E,Q40V,A42del,N43A,L44I)
SEQ ID NO 78
VDAKFDKEAQ EAFYEILHLP NLTEEQRNAF IQSLKDDPSV

S_AILAEAKK LNDAQAPK

Zvar(Q9A,N11E,Q40V,A42K,N43del,L44I)
SEQ ID NO 79
VDAKFDKEAQ EAFYEILHLP NLTEEQRNAF IQSLKDDPSV

SK_ILAEAKK LNDAQAPK

Zvar(D2del,A3del,K4del,Q9A,N11E,Q40V,A42K,N43A,L44I)
SEQ ID NO 89
V___FDKEAQ EAFYEILHLP NLTEEQRNAF IQSLKDDPSV

SKAILAEAKK LNDAQAPK

Zvar(V1del,D2del,Q9A,N11E,Q40V,A42K,N43A,L44I,K58del)
SEQ ID NO 90
__AKFDKEAQ EAFYEILHLP NLTEEQRNAF IQSLKDDPSV

SKAILAEAKK LNDAQAP_

Zvar(K4del,F5del,D6del,K7del,E8del,Q9A,N11E,Q40V,A42K,N43A,L44I)
SEQ ID NO 91
VDA_____AQ EAFYEILHLP NLTEEQRNAF IQSLKDDPSV

SKAILAEAKK LNDAQAPK

Zvar(Q9A,N11E,Q40V,A42K,N43A,L44I,A56del,P57del,K58del)
SEQ ID NO 92
VDAKFDKEAQ EAFYEILHLP NLTEEQRNAF IQSLKDDPSV

SKAILAEAKK LNDAQ___

Zvar(V1del, ,D2del,A3del,Q9A,N11E,Q40V,A42K,N43A,L44I)
SEQ ID NO 93
___KFDKEAQ EAFYEILHLP NLTEEQRNAF IQSLKDDPSV

SKAILAEAKK LNDAQAPK

Zvar(V1del,D2del,A3del,K4del,F5del,D6del,K7del,E8del,Q9A,N11E,Q40V,A42K,N43A,L44I)
SEQ ID NO 94
_____AQ EAFYEILHLP NLTEEQRNAF IQSLKDDPSV

SKAILAEAKK LNDAQAPK

Zvar(Q9A,N11E,Q40V,A42K,N43A,L44I,K58_insYEDG)
SEQ ID NO 95
VDAKFDKEAQ EAFYEILHLP NLTEEQRNAF IQSLKDDPSV

SKAILAEAKK LNDAQAPKYE DG

In a second aspect the present invention discloses a multimer comprising, or consisting essentially of, a plurality of polypeptide units as defined by any embodiment disclosed above. The use of multimers may increase the immunoglobulin binding capacity and multimers may also have a higher alkali stability than monomers. The multimer can e.g. be a dimer, a trimer, a tetramer, a pentamer, a hexamer, a heptamer, an octamer or a nonamer. It can be a homomultimer, where all the units in the multimer are identical or it can be a heteromultimer, where at least one unit differs from the others. Advantageously, all the units in the multimer are alkali stable, such as by comprising the mutations disclosed above. The polypeptides can be linked to each other directly by peptide bonds between the C-terminal and N-terminal ends of the polypeptides. Alternatively, two or more units in the multimer can be linked by linkers comprising oligomeric or polymeric species, such as linkers comprising peptides with up to 25 or 30 amino acids, such as 3-25 or 3-20 amino acids. The linkers may e.g. comprise or consist essentially of a peptide sequence defined by, or having at least 90% identity or at least 95% identity, with an amino acid sequence selected from the group consisting of APKVDAKFDKE (SEQ ID NO: 96), APKVDNKFNKE (SEQ ID NO: 97), APKADNKFNKE (SEQ ID NO: 98), APKVFDKE (SEQ ID NO: 99), APAKFDKE (SEQ ID NO: 100), AKFDKE (SEQ ID NO: 101), APKVDA (SEQ ID NO: 102), VDAKFDKE (SEQ ID NO: 103), APKKFDKE (SEQ ID NO: 104), APK, APKYEDGVDAKFDKE (SEQ ID NO: 105) and YEDG (SEQ ID NO:106) or alternatively selected from the group consisting of APKADNKFNKE (SEQ ID NO: 98), APKVFDKE (SEQ ID NO: 99), APAKFDKE (SEQ ID NO: 100), AKFDKE (SEQ ID NO: 101), APKVDA (SEQ ID NO: 102), VDAKFDKE (SEQ ID NO: 103), APKKFDKE (SEQ ID NO: 104), APKYEDGVDAKFDKE (SEQ ID NO: 105) and YEDG (SEQ ID NO: 106). They can also consist essentially of a peptide sequence defined by or having at least 90% identity or at least 95% identity with an amino acid sequence selected from the group consisting of APKADNKFNKE (SEQ ID NO: 98), APKVFDKE (SEQ ID NO: 99), APAKFDKE (SEQ ID NO: 100), AKFDKE (SEQ ID NO: 101), APKVDA (SEQ ID NO: 102), VDAKFDKE (SEQ ID NO: 103), APKKFDKE (SEQ ID NO: 104), APK and APKYEDGVDAKFDKE (SEQ ID NO: 105). In some embodiments the linkers do not consist of the peptides APKVDAKFDKE (SEQ ID NO: 96) or APKVDNKFNKE (SEQ ID NO: 97), or alternatively do not consist of the peptides APKVDAKFDKE (SEQ ID NO: 96), APKVDNKFNKE (SEQ ID NO: 97), APKFNKE (SEQ ID NO: 107), APKFDKE (SEQ ID NO: 108), APKVDKE (SEQ ID NO: 109) or APKADKE (SEQ ID NO: 110).

The nature of such a linker should preferably not destabilize the spatial conformation of the protein units. This can e.g. be achieved by avoiding the presence of proline in the linkers. Furthermore, said linker should preferably also be sufficiently stable in alkaline environments not to impair the properties of the mutated protein units. For this purpose, it is advantageous if the linkers do not contain asparagine. It can additionally be advantageous if the linkers do not contain glutamine. The multimer may further at the N-terminal end comprise a plurality of amino acid residues e.g. originating from the cloning process or constituting a residue from a cleaved off signaling sequence. The number of additional amino acid residues may e.g. be 20 or less, such as 15 or less, such as 10 or less or 5 or less. As a specific example, the multimer may comprise an AQ, AQGT (SEQ ID NO: 111), VDAKFDKE (SEQ ID NO: 103), AQVDAKFDKE (SEQ ID NO: 112) or AQGTVDAKFDKE (SEQ ID NO: 113) sequence at the N-terminal end.

In certain embodiments, the multimer may comprise, or consist essentially, of a sequence selected from the group consisting of: SEQ ID NO 80-87. These and additional sequences are listed below and named as Parent (Mutations) n, where n is the number of monomer units in a multimer.

Zvar(Q9A,N11E,N43A)4
SEQ ID NO 17
AQGT VDAKFDKEAQ EAFYEILHLP NLTEEQRNAF IQSLKDDPSQ

SAALLAEAKK LNDAQAPK VDAKFDKEAQ EAFYEILHLP

NLTEEQRNAF IQSLKDDPSQ SAALLAEAKK LNDAQAPK

VDAKFDKEAQ EAFYEILHLP NLTEEQRNAF IQSLKDDPSQ

SAALLAEAKK LNDAQAPK VDAKFDKEAQ EAFYEILHLP

NLTEEQRNAF IQSLKDDPSQ SAALLAEAKK LNDAQAPKC

Zvar(Q9A,N11E,N28A,N43A)4
SEQ ID NO 18
AQGT VDAKFDKEAQ EAFYEILHLP NLTEEQRAAF IQSLKDDPSQ

SAALLAEAKK LNDAQAPK VDAKFDKEAQ EAFYEILHLP

NLTEEQRAAF IQSLKDDPSQ SAALLAEAKK LNDAQAPK

VDAKFDKEAQ EAFYEILHLP NLTEEQRAAF IQSLKDDPSQ

SAALLAEAKK LNDAQAPK VDAKFDKEAQ EAFYEILHLP

NLTEEQRAAF IQSLKDDPSQ SAALLAEAKK LNDAQAPKC

Zvar(Q9A,N11E,Q40V,A42K,N43E,L44I)4
SEQ ID NO 19
AQGT VDAKFDKEAQ EAFYEILHLP NLTEEQRNAF IQSLKDDPSV

SKEILAEAKK LNDAQAPK VDAKFDKEAQ EAFYEILHLP

NLTEEQRNAF IQSLKDDPSV SKEILAEAKK LNDAQAPK

VDAKFDKEAQ EAFYEILHLP NLTEEQRNAF IQSLKDDPSV

SKEILAEAKK LNDAQAPK VDAKFDKEAQ EAFYEILHLP

NLTEEQRNAF IQSLKDDPSV SKEILAEAKK LNDAQAPKC

Zvar(Q9A,N11E,Q40V,A42K,N43A,L44I)4
SEQ ID NO 20
AQGT VDAKFDKEAQ EAFYEILHLP NLTEEQRNAF IQSLKDDPSV

SKAILAEAKK LNDAQAPK VDAKFDKEAQ EAFYEILHLP

NLTEEQRNAF IQSLKDDPSV SKAILAEAKK LNDAQAPK

VDAKFDKEAQ EAFYEILHLP NLTEEQRNAF IQSLKDDPSV

SKAILAEAKK LNDAQAPK VDAKFDKEAQ EAFYEILHLP

NLTEEQRNAF IQSLKDDPSV SKAILAEAKK LNDAQAPKC

Zvar(N11K,H18K,S33K,D37E,A42R,N43A,L44I,K50R,L51Y)4
SEQ ID NO 30
AQGT VDAKFDKEQQ KAFYEILKLP NLTEEQRNAF IQKLKDEPSQ

SRAILAEAKR YNDAQAPK VDAKFDKEQQ KAFYEILKLP

NLTEEQRNAF IQKLKDEPSQ SRAILAEAKR YNDAQAPK

VDAKFDKEQQ KAFYEILKLP NLTEEQRNAF IQKLKDEPSQ

SRAILAEAKR YNDAQAPK VDAKFDKEQQ KAFYEILKLP

NLTEEQRNAF IQKLKDEPSQ SRAILAEAKR YNDAQAPKC

Zvar(Q9A,N11K,H18K,D37E,A42R)4
SEQ ID NO 31
AQGT VDAKFDKEAQ KAFYEILKLP NLTEEQRNAF IQSLKDEPSQ

SRNLLAEAKK LNDAQAPK VDAKFDKEAQ KAFYEILKLP

NLTEEQRNAF IQSLKDEPSQ SRNLLAEAKK LNDAQAPK

VDAKFDKEAQ KAFYEILKLP NLTEEQRNAF IQSLKDEPSQ

```
SRNLLAEAKK LNDAQAPK VDAKFDKEAQ KAFYEILKLP

NLTEEQRNAF IQSLKDEPSQ SRNLLAEAKK LNDAQAPKC

Zvar(Q9A,N11E,N28A,Q40V,A42K,N43A,L44I)4
                                           SEQ ID NO 32
AQGT VDAKFDKEAQ EAFYEILHLP NLTEEQRAAF IQSLKDDPSV

SKAILAEAKK LNDAQAPK VDAKFDKEAQ EAFYEILHLP

NLTEEQRAAF IQSLKDDPSV SKAILAEAKK LNDAQAPK

VDAKFDKEAQ EAFYEILHLP NLTEEQRAAF IQSLKDDPSV

SKAILAEAKK LNDAQAPK VDAKFDKEAQ EAFYEILHLP

NLTEEQRAAF IQSLKDDPSV SKAILAEAKK LNDAQAPKC

Zvar(Q9A,N11E,Q40V,A42K,N43A,L44I)6
                                           SEQ ID NO 33
AQGT VDAKFDKEAQ EAFYEILHLP NLTEEQRNAF IQSLKDDPSV

SKAILAEAKK LNDAQAPK VDAKFDKEAQ EAFYEILHLP

NLTEEQRNAF IQSLKDDPSV SKAILAEAKK LNDAQAPK

VDAKFDKEAQ EAFYEILHLP NLTEEQRNAF IQSLKDDPSV

SKAILAEAKK LNDAQAPK VDAKFDKEAQ EAFYEILHLP

NLTEEQRNAF IQSLKDDPSV SKAILAEAKK LNDAQAPK

VDAKFDKEAQ EAFYEILHLP NLTEEQRNAF IQSLKDDPSV

SKAILAEAKK LNDAQAPK VDAKFDKEAQ EAFYEILHLP

NLTEEQRNAF IQSLKDDPSV SKAILAEAKK LNDAQAPKC

Zvar(Q9A,N11E,D37E,Q40V,A42K,N43A,L44I)4
                                           SEQ ID NO 34
AQGT VDAKFDKEAQ EAFYEILHLP NLTEEQRNAF IQSLKDEPSV

SKAILAEAKK LNDAQAPK VDAKFDKEAQ EAFYEILHLP

NLTEEQRNAF IQSLKDEPSV SKAILAEAKK LNDAQAPK

VDAKFDKEAQ EAFYEILHLP NLTEEQRNAF IQSLKDEPSV

SKAILAEAKK LNDAQAPK VDAKFDKEAQ EAFYEILHLP

NLTEEQRNAF IQSLKDEPSV SKAILAEAKK LNDAQAPKC

Zvar(Q9A,N11E,D37E,Q40V,A42R,N43A,L44I)4
                                           SEQ ID NO 35
AQGT VDAKFDKEAQ EAFYEILHLP NLTEEQRNAF IQSLKDEPSV

SRAILAEAKK LNDAQAPK VDAKFDKEAQ EAFYEILHLP

NLTEEQRNAF IQSLKDEPSV SRAILAEAKK LNDAQAPK

VDAKFDKEAQ EAFYEILHLP NLTEEQRNAF IQSLKDEPSV

SRAILAEAKK LNDAQAPK VDAKFDKEAQ EAFYEILHLP

NLTEEQRNAF IQSLKDEPSV SRAILAEAKK LNDAQAPKC

Zvar(Q9A,N11E,Q40V,A42K,N43A,L44I)2 with D2, A3 and
K4 in linker deleted
                                           SEQ ID NO 80
VDAKFDKEAQ EAFYEILHLP NLTEEQRNAF IQSLKDDPSV

SKAILAEAKK LNDAQAPK VFDKEAQ EAFYEILHLP NLTEEQRNAF

IQSLKDDPSV SKAILAEAKK LNDAQAPKC

Zvar(Q9A,N11E,Q40V,A42K,N43A,L44I)2 with K58, V1
and D2 in linker deleted
                                           SEQ ID NO 81
VDAKFDKEAQ EAFYEILHLP NLTEEQRNAF IQSLKDDPSV

SKAILAEAKK LNDAQAP AKFDKEAQ EAFYEILHLP NLTEEQRNAF

IQSLKDDPSV SKAILAEAKK LNDAQAPKC

Zvar(Q9A,N11E,Q40V,A42K,N43A,L44I)2 with P57, K58,
V1, D2 and A3 in linker deleted
                                           SEQ ID NO 82
VDAKFDKEAQ EAFYEILHLP NLTEEQRNAF IQSLKDDPSV

SKAILAEAKK LNDAQAP AKFDKEAQ EAFYEILHLP NLTEEQRNAF

IQSLKDDPSV SKAILAEAKK LNDAQAPKC

Zvar(Q9A,N11E,Q40V,A42K,N43A,L44I)2 with K4, F5,
D6, K7 and E8 in linker deleted
                                           SEQ ID NO C-terminal end. The coupling element(s) may be directly linked to the C- or N-terminal end, or it/they may be linked via a stretch comprising up to 15 amino acids, such as 1-5, 1-10 or 5-10 amino acids. This stretch should preferably also be sufficiently stable in alkaline environments not to impair the properties of the mutated protein. For this purpose, it is advantageous if the stretch does not contain asparagine. It can additionally be advantageous if the stretch does not contain glutamine. An advantage of having a C-terminal cysteine is that endpoint coupling of the protein can be achieved through reaction of the cysteine thiol with an electrophilic group on a support. This provides excellent mobility of the coupled protein which is important for the binding capacity.

The alkali stability of the polypeptide or multimer can be assessed by coupling it to an SPR chip, e.g. to Biacore CM5 sensor chips as described in the examples, using e.g. NHS- or maleimide coupling chemistries, and measuring the immunoglobulin-binding capacity of the chip, typically using polyclonal human IgG, before and after incubation in alkaline solutions at a specified temperature, e.g. 22+/−2° C. The incubation can e.g. be performed in 0.5 M NaOH for a number of 10 min cycles, such as 100, 200 or 300 cycles. The IgG capacity of the matrix after 100 10 min incubation cycles in 0.5 M NaOH at 22+/−2° C. can be at least 55, such as at least 60, at least 80 or at least 90% of the IgG capacity before the incubation. Alternatively, the remaining IgG capacity after 100 cycles for a particular mutant measured as above can be compared with the remaining IgG capacity for the parental polypeptide/multimer. In this case, the remaining IgG capacity for the mutant may be at least 105%, such as at least 110%, at least 125%, at least 150% or at least 200% of the parental polypeptide/multimer.

In a third aspect the present invention discloses a nucleic acid encoding a polypeptide or multimer according to any embodiment disclosed above. Thus, the invention encompasses all forms of the present nucleic acid sequence such as the RNA and the DNA encoding the polypeptide or multimer. The invention embraces a vector, such as a plasmid, which in addition to the coding sequence comprises the required signal sequences for expression of the polypeptide or multimer according the invention. In one embodiment, the vector comprises nucleic acid encoding a multimer according to the invention, wherein the separate nucleic acids encoding each unit may have homologous or heterologous DNA sequences.

In a fourth aspect the present invention discloses an expression system, which comprises, a nucleic acid or a vector as disclosed above. The expression system may e.g. be a gram-positive or gram-negative prokaryotic host cell system, e.g. *E. coli* or *Bacillus* sp. which has been modified to express the present polypeptide or multimer. In an alternative embodiment, the expression system is a eukaryotic host cell system, such as a yeast, e.g. *Pichia pastoris* or *Saccharomyces cerevisiae*, or mammalian cells, e.g. CHO cells.

In a fifth aspect, the present invention discloses a separation matrix, wherein a plurality of polypeptides or multimers according to any embodiment disclosed above have been coupled to a solid support. The separation matrix may comprise at least 11, such as 11-21, 15-21 or 15-18 mg/ml Fc-binding ligands covalently coupled to a porous support, wherein:

a) the ligands comprise multimers of alkali-stabilized Protein A domains,
b) the porous support comprises cross-linked polymer particles having a volume-weighted median diameter (d50,v) of 56-70, such as 56-66, micrometers and a dry solids weight of 55-80, such as 60-78 or 65-78, mg/ml. The cross-linked polymer particles may further have a pore size corresponding to an inverse gel filtration chromatography Kd value of 0.69-0.85, such as 0.70-0.85 or 0.69-0.80, for dextran of Mw 110 kDa. Suitably, the cross-linked polymer particles can have a high rigidity, to be able to withstand high flow rates. The rigidity can be measured with a pressure-flow test as further described in Example 11, where a column packed with the matrix is subjected to increasing flow rates of distilled water. The pressure is increased stepwise and the flow rate and back pressure measured, until the flow rate starts to decrease with increasing pressures. The maximum flow rate achieved and the maximum pressure (the back pressure corresponding to the maximum flow rate) are measured and used as measures of the rigidity. When measured in a FineLine™ 35 column (GE Healthcare Life Sciences) at a bed height of 300+/−10 mm, the max pressure can suitably be at least 0.58 MPa, such as at least 0.60 MPa. This allows for the use of smaller particle diameters, which is beneficial for the dynamic capacity. The multimers may e.g. comprise tetramers, pentamers, hexamers or heptamers of alkali-stabilized Protein A domains, such as hexamers of of alkali-stabilized Protein A domains. The combination of the high ligand contents with the particle size range, the dry solids weight range and the optional Kd range provides for a high binding capacity, e.g. such that the 10% breakthrough dynamic binding capacity for IgG is at least 45 mg/ml, such as at least 50 or at least 55 mg/ml at 2.4 min residence time. Alternatively, or additionally, the 10% breakthrough dynamic binding capacity for IgG may be at least 60 mg/ml, such as at least 65, at least 70 or at least 75 mg/ml at 6 min residence time. The alkali-stabilized Protein A multimers are highly selective for IgG and the separation matrix can suitably have a dissociation constant for human IgG2 of below 0.2 mg/ml, such as below 0.1 mg/ml, in 20 mM phosphate buffer, 180 mM NaCl, pH 7.5. This can be determined according to the adsorption isotherm method described in N Pakiman et al: J Appl Sci 12, 1136-1141 (2012).

In certain embodiments the alkali-stabilized Protein A domains comprise mutants of a parental Fc-binding domain of *Staphylococcus* Protein A (SpA), as defined by, or having at least 80% such as at least 90%, 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO: 51 or SEQ ID NO: 52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine, such as an amino acid selected from the group consisting of glutamic acid and lysine. The amino acid residue at the position corresponding to position 40 in SEQ ID NO:4-7 may further be, or be mutated to, a valine. The alkali-stabilized Protein A domains may also comprise any mutations as described in the polypeptide and/or multimer embodiments above.

In some embodiments the alkali-stabilized Protein A domains comprise an Fc-binding polypeptide having an amino acid sequence as defined by, or having at least 80% or at least 90%, 95% or 98% identity to SEQ ID NO: 53.

(SEQ ID NO: 53)
$X_1Q$ $X_2AFYEILX_3LP$ $NLTEEQRX_4X_5F$ $IX_6X_7LKDX_8PSX_9$ $SX_{10}X_{11}X_{12}LAEAKX_{13}$ $X_{14}NX_{15}AQ$ wherein individually of each other:
$X_1$=A or Q or is deleted
$X_2$=E, K, Y, T, F, L, W, I, M, V, A, H or R $X_3$=H or K
$X_4$=A or N
$X_5$=A, G, S, Y, Q, T, N, F, L, W, I, M, V, D, E, H, R or K
$X_6$=Q or E
$X_7$=S or K
$X_8$=E or D
$X_9$=Q or V or is deleted
$X_{10}$=K, R or A or is deleted
$X_{11}$=A, E or N or is deleted
$X_{12}$=I or L
$X_{13}$=K or R
$X_{14}$=L or Y
$X_{15}$=D, F, Y, W, K or R In some embodiments, the amino acid residues may individually of each other be:

a) $X_1$=A or is deleted, $X_2$=E, $X_3$=H, $X_4$=N, $X_6$=Q, $X_7$=5, $X_8$=D, $X_9$=V or is deleted, $X_{10}$=K or is deleted, $X_{11}$=A or is deleted, $X_{12}$=I, $X_{13}$=K, $X_{14}$=L.

b) $X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

c) $X_1$ is A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D or d) $X_1$ is A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

In certain embodiments the invention discloses a separation matrix comprising at least 15, such as 15-21 or 15-18 mg/ml Fc-binding ligands covalently coupled to a porous support, wherein the ligands comprise multimers of alkali-stabilized Protein A domains. These multimers can suitably be as disclosed in any of the embodiments described above or as specified below.

Such a matrix is useful for separation of immunoglobulins or other Fc-containing proteins and, due to the improved alkali stability of the polypeptides/multimers, the matrix will withstand highly alkaline conditions during cleaning, which is essential for long-term repeated use in a bioprocess separation setting. The alkali stability of the matrix can be assessed by measuring the immunoglobulin-binding capacity, typically using polyclonal human IgG, before and after incubation in alkaline solutions at a specified temperature, e.g. 22+/−2° C. The incubation can e.g. be performed in 0.5 M or 1.0 M NaOH for a number of 15 min cycles, such as 100, 200 or 300 cycles, corresponding to a total incubation time of 25, 50 or 75 h. The IgG capacity of the matrix after 96-100 15 min incubation cycles or a total incubation time of 24 or 25 h in 0.5 M NaOH at 22+/−2° C. can be at least 80, such as at least 85, at least 90 or at least 95% of the IgG capacity before the incubation. The capacity of the matrix after a total incubation time of 24 h in 1.0 M NaOH at 22+/−2° C. can be at least 70, such as at least 80 or at least 90% of the IgG capacity before the incubation. The the 10% breakthrough dynamic binding capacity (Qb10%) for IgG at 2.4 min or 6 min residence time may e.g. be reduced by less than 20% after incubation 31 h in 1.0 M aqueous NaOH at 22+/−2 C.

As the skilled person will understand, the expressed polypeptide or multimer should be purified to an appropriate extent before being immobilized to a support. Such purification methods are well known in the field, and the immobilization of protein-based ligands to supports is easily carried out using standard methods. Suitable methods and supports will be discussed below in more detail.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. The solid support can suitably be porous. The porosity can be expressed as a Kay or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. Kay is determined as the ratio $(V_e—V_0)/(V_t—V_0)$, where Ve is the elution volume of a probe molecule (e.g. Dextran 110 kD), $V_0$ is the void volume of the column (e.g. the elution volume of a high Mw void marker, such as raw dextran) and $V_t$ is the total volume of the column. Kd can be determined as $(V_e—V_0)/V_i$, where $V_i$ is the elution volume of a salt (e.g. NaCl) able to access all the volume except the matrix volume (the volume occupied by the matrix polymer molecules). By definition, both Kd and Kay values always lie within the range 0-1. The Kay value can advantageously be 0.6-0.95, e.g. 0.7-0.90 or 0.6-0.8, as measured with dextran of Mw 110 kDa as a probe molecule. The Kd value as measured with dextran of Mw 110 kDa can suitably be 0.68-0.90, such as 0.68-0.85 or 0.70-0.85. An advantage of this is that the support has a large fraction of pores able to accommodate both the polypeptides/multimers of the invention and immunoglobulins binding to the polypeptides/multimers and to provide mass transport of the immunoglobulins to and from the binding sites.

The polypeptides or multimers may be attached to the support via conventional coupling techniques utilising e.g. thiol, amino and/or carboxy groups present in the ligand. Bisepoxides, epichlorohydrin, CNBr, N-hydroxysuccinimide (NHS) etc are well-known coupling reagents. Between the support and the polypeptide/multimer, a molecule known as a spacer can be introduced, which improves the availability of the polypeptide/multimer and facilitates the chemical coupling of the polypeptide/multimer to the support. Depending on the nature of the polypeptide/multimer and the coupling conditions, the coupling may be a multipoint coupling (e.g. via a plurality of lysines) or a single point coupling (e.g. via a single cysteine). Alternatively, the polypeptide/multimer may be attached to the support by non-covalent bonding, such as physical adsorption or biospecific adsorption.

In some embodiments the matrix comprises 5-25, such as 5-20 mg/ml, 5-15 mg/ml, 5-11 mg/ml or 6-11 mg/ml of the polypeptide or multimer coupled to the support. The amount of coupled polypeptide/multimer can be controlled by the concentration of polypeptide/multimer used in the coupling process, by the activation and coupling conditions used and/or by the pore structure of the support used. As a general rule the absolute binding capacity of the matrix increases with the amount of coupled polypeptide/multimer, at least up to a point where the pores become significantly constricted by the coupled polypeptide/multimer. Without being bound by theory, it appears though that for the Kd values recited for the support, the constriction of the pores by coupled ligand is of lower significance. The relative binding capacity per mg coupled polypeptide/multimer will decrease at high coupling levels, resulting in a cost-benefit optimum within the ranges specified above.

In certain embodiments the polypeptides or multimers are coupled to the support via thioether bonds. Methods for performing such coupling are well-known in this field and easily performed by the skilled person in this field using standard techniques and equipment. Thioether bonds are flexible and stable and generally suited for use in affinity chromatography. In particular when the thioether bond is via a terminal or near-terminal cysteine residue on the polypeptide or multimer, the mobility of the coupled polypeptide/multimer is enhanced which provides improved binding capacity and binding kinetics. In some embodiments the polypeptide/multimer is coupled via a C-terminal cysteine provided on the protein as described above. This allows for efficient coupling of the cysteine thiol to electrophilic groups, e.g. epoxide groups, halohydrin groups etc. on a support, resulting in a thioether bridge coupling.

In certain embodiments the support comprises a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline cleaning solutions used in bioprocessing.

In some embodiments the support comprises agar or agarose. The supports used in the present invention can easily be prepared according to standard methods, such as inverse suspension gelation (S Hjertén: Biochim Biophys Acta 79(2), 393-398 (1964). Alternatively, the base matrices are commercially available products, such as crosslinked agarose beads sold under the name of SEPHAROSE™ FF (GE Healthcare). In an embodiment, which is especially advantageous for large-scale separations, the support has been adapted to increase its rigidity using the methods described in U.S. Pat. No. 6,602,990 or 7,396,467, which are hereby incorporated by reference in their entireties, and hence renders the matrix more suitable for high flow rates.

In certain embodiments the support, such as a polymer, polysaccharide or agarose support, is crosslinked, such as with hydroxyalkyl ether crosslinks. Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support and improves the chemical stability. Hydroxyalkyl ether crosslinks are alkali stable and do not cause significant nonspecific adsorption.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the solid support according to the invention comprises a support of inorganic nature, e.g. silica, zirconium oxide etc.

In yet another embodiment, the solid support is in another form such as a surface, a chip, capillaries, or a filter (e.g. a membrane or a depth filter matrix).

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

In a sixth aspect, the present invention discloses a method of isolating an immunoglobulin, wherein a separation matrix as disclosed above is used. The method may comprise the steps of:

a) contacting a liquid sample comprising an immunoglobulin with a separation matrix as disclosed above, b) washing the separation matrix with a washing liquid, c) eluting the immunoglobulin from the separation matrix with an elution liquid, and d) cleaning the separation matrix with a cleaning liquid, which may comprise 0.1-1.0 M NaOH or KOH, such as 0.4-1.0 M NaOH or KOH.

Steps a)-d) may be repeated at least 10 times, such as at least 50 times or 50-200 times.

The invention also discloses a method of isolating an immunoglobulin, comprising the steps of:

a) providing a separation matrix comprising multimers of immunoglobulin-binding alkali-stabilized Protein A domains covalently coupled to a porous support, b) contacting a liquid sample comprising an immunoglobulin with said separation matrix, c) washing said separation matrix with a washing liquid, d) eluting the immunoglobulin from the separation matrix with an elution liquid, and e) cleaning the separation matrix with a cleaning liquid, wherein said alkali-stabilized Protein A domains comprise mutants of a parental Fc-binding domain of *Staphylococcus* Protein A (SpA), as defined by, or having at least 80% such as at least 90%, 95% or 98% identity to, SEQ ID NO: 51 or SEQ ID NO: 52, wherein the amino acid residues at positions 13 and 44 of SEQ ID NO: 51 or 52 are asparagines and wherein at least the asparagine residue at position 3 of SEQ ID NO: 51 or 52 has been mutated to an amino acid selected from the group consisting of glutamic acid, lysine, tyrosine, threonine, phenylalanine, leucine, isoleucine, tryptophan, methionine, valine, alanine, histidine and arginine.

The glutamine residue at position 1 of SEQ ID NO: 51 or 52 may further be mutated to an alanine and/or the asparagine or glutamic acid residue at position 35 of SEQ ID NO: 51 or 52 may be mutated to an alanine.

The separation matrix may e.g. comprise at least 11 mg/ml, such as at least 15 mg/ml or 11-20 mg/ml, of the multimers of immunoglobulin-binding alkali-stabilized Protein A domains covalently coupled to the porous support.

In step b) at least 40 mg immunoglobulin per ml separation matrix, such as at least 50 mg per ml, 40-90, 40-80, 40-70 or 40-60 mg per ml matrix may be contacted with the separation matrix. A high degree of loading in step b) is highly desirable for the process economy and can be achieved due to the high dynamic binding capacity of the matrix.

In step e) the cleaning liquid may comprise at least 0.5 M NaOH, such as at least 0.7 M, at least 0.9 M or at least 1 M NaOH. It may also comprise 0.5-1.5 M NaOH, such as 0.5-1.1, 0.7-1.2 or 0.9-1.1 M NaOH. As an alternative to NaOH it is also possible to use KOH, or NaOH/KOH mixtures, at the same concentrations.

Steps b)-e) may be repeated at least 10 times, such as at least 50 times, at least 100 times, 50-200 times or 50-150 times. The duration of step e) may e.g. be at least 5 min, such as at least 10 min or 5-60 min, such as 5-30 min or 10-20 min.

The liquid sample may be a clarified cell broth, e.g. a clarified mammalian cell broth such as a CHO cell broth. In step d) the immunoglobulin may be recovered as an eluate comprising less than 2000 ppm, such as less than 1500 ppm or less than 1200 ppm host cell proteins, e.g. CHO cell proteins. In relative terms, the ratio of the host cell protein concentration in the liquid sample to the host cell concentration in the eluate may be at least 100, such as at least 200 or at least 300. A high clearance of host cell proteins, in either relative or absolute terms, as early as possible in the process is desirable to facilitate the further purification of the antibody.

If so desired, the method may further comprise a virus inactivation step. The virus inactivation can be performed after elution in the conventional way but it may also be performed when the immunoglobulin is present in the column, e.g. as disclosed in WO2015048330 or WO2015166072, which are both incorporated by reference in their entireties.

In step d) the elution liquid may e.g. have a pH of 2.5-5.0 or 3.0-5.0, such as 2.5-4.5, 3.0-4.5 or 3.2-4.5. The elution liquid may in some cases contain additives such as salts, amino acids, specific buffering agents etc. The elution may be performed by a distinct step change or by the application of a gradient, e.g. a pH gradient. Suitable elution conditions are described in e.g. WO2014159064, U.S. Pat. Nos. 8,084, 032, 8,853,371, US20080167450, US20110144311, US20130096284, US20120238730, US20140018525, WO2013033517, US20140228548, WO2014159064, US20150093800, which are all incorporated by reference in their entireties.

The immunoglobulin may in particular comprise IgG1, IgG2 and/or IgG4. As shown in the examples, the current matrices bind these IgG classes.

The washing liquid may e.g. have a pH of 5-8. The washing liquid may comprise an additive for improving the washing efficiency, e.g. to improve the host cell protein clearance. Such additives are known in the art and may comprise one or more of a detergent, a water-miscible organic solvent, a chaotrope, arginine or an arginine derivative, calcium ions and tetraalkylammonium ions. The following documents describing suitable additives are hereby incorporated by reference in their entireties: U.S. Pat. Nos. 6,127,526, 6,870,034, 7,820,799, 7,834,162, 8,263,750, 7,714,111, 9,284,347, US20120283416, US20130197197, WO2014186350, WO2014192877, US20140094593, US20160108084 and US20160024147.

The multimers may be coupled to the support via thioether links as described above.

In step b) the pH may e.g. be 6-8. The residence time in this step may e.g. be 2-20 min, such as 2-10 min. Specific loading conditions are described e.g. in U.S. Pat. Nos. 4,704,366, 4,801,687, 4,933,435, EP2782925A1, US20140154270, which are all incorporated by reference in their entireties.

The porous support may e.g. comprise cross-linked polymer particles having a volume-weighted median diameter (d50,v) of 56-70 micrometers and a dry solids weight of 55-80 mg/ml. The cross-linked polymer particles may e.g. have a pore size corresponding to an inverse gel filtration chromatography Kd value of 0.69-0.85 for dextran of Mw 110 kDa.

In certain embodiments the method of the invention comprises the steps of:
a) providing a separation matrix comprising at least 15 mg/ml multimers of immunoglobulin-binding alkali-stabilized Protein A domains covalently coupled to a porous support,
b) contacting a liquid sample comprising an immunoglobulin with said separation matrix,
c) washing said separation matrix with a washing liquid,
d) eluting the immunoglobulin from the separation matrix with an elution liquid, and
e) cleaning the separation matrix with a cleaning liquid comprising at least 0.5 M NaOH, wherein in step b) at least 40 mg immunoglobulin per ml separation matrix is contacted with said separation matrix.

In certain embodiments, the method comprises the steps of:
a) contacting a liquid sample comprising an immunoglobulin with a separation matrix as disclosed above,
b) washing said separation matrix with a washing liquid,
c) eluting the immunoglobulin from the separation matrix with an elution liquid, and
d) cleaning the separation matrix with a cleaning liquid, which can alternatively be called a cleaning-in-place (CIP) liquid, e.g. with a contact (incubation) time of at least 10 min.

The method may also comprise steps of, before step a), providing an affinity separation matrix according to any of the embodiments described above and providing a solution comprising an immunoglobulin and at least one other substance as a liquid sample and of, after step c), recovering the eluate and optionally subjecting the eluate to further separation steps, e.g. by anion or cation exchange chromatography, multimodal chromatography and/or hydrophobic interaction chromatography. Suitable compositions of the liquid sample, the washing liquid and the elution liquid, as well as the general conditions for performing the separation are well known in the art of affinity chromatography and in particular in the art of Protein A chromatography. The liquid sample comprising an Fc-containing protein and at least one other substance may comprise host cell proteins (HCP), such as CHO cell, *E Coli* or yeast proteins. Contents of CHO cell and *E Coli* proteins can conveniently be determined by immunoassays directed towards these proteins, e.g. the CHO HCP or *E Coli* HCP ELISA kits from *Cygnus* Technologies. The host cell proteins or CHO cell/*E Coli* proteins may be desorbed during step b).

The elution may be performed by using any suitable solution used for elution from Protein A media. This can e.g. be a solution or buffer with pH 5 or lower, such as pH 2.5-5 or 3-5. It can also in some cases be a solution or buffer with pH 11 or higher, such as pH 11-14 or pH 11-13. In some embodiments the elution buffer or the elution buffer gradient comprises at least one mono- di- or trifunctional carboxylic acid or salt of such a carboxylic acid. In certain embodiments the elution buffer or the elution buffer gradient comprises at least one anion species selected from the group consisting of acetate, citrate, glycine, succinate, phosphate, and formiate.

In some embodiments, the cleaning liquid is alkaline, such as with a pH of 13-14. Such solutions provide efficient cleaning of the matrix, in particular at the upper end of the interval In certain embodiments, the cleaning liquid comprises 0.1-2.0 M NaOH or KOH, such as 0.5-2.0 or 0.5-1.0 M NaOH or KOH. These are efficient cleaning solutions, and in particular so when the NaOH or KOH concentration is above 0.1 M or at least 0.5 M. The high stability of the polypeptides of the invention enables the use of such strongly alkaline solutions.

The method may also include a step of sanitizing the matrix with a sanitization liquid, which may e.g. comprise a peroxide, such as hydrogen peroxide and/or a peracid, such as peracetic acid or performic acid.

In some embodiments, steps a)-d) are repeated at least 10 times, such as at least 50 times, 50-200, 50-300 or 50-500 times. This is important for the process economy in that the matrix can be re-used many times.

Steps a)-c) can also be repeated at least 10 times, such as at least 50 times, 50-200, 50-300 or 50-500 times, with step d) being performed after a plurality of instances of step c), such that step d) is performed at least 10 times, such as at least 50 times. Step d) can e.g. be performed every second to twentieth instance of step c).

EXAMPLES

Mutagenesis of Protein

Site-directed mutagenesis was performed by a two-step PCR using oligonucleotides coding for the mutations. As template a plasmid containing a single domain of either Z, B or C was used. The PCR fragments were ligated into an E. coli expression vector. DNA sequencing was used to verify the correct sequence of inserted fragments.

To form multimers of mutants an Acc I site located in the starting codons (GTA GAC) of the B, C or Z domain was used, corresponding to amino acids VD. The vector for the monomeric domain was digested with Acc I and phosphatase treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.→25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing the desired mutant. Positive clones were verified by DNA sequencing.

Construct Expression and Purification

The constructs were expressed in the bacterial periplasm by fermentation of E. coli K12 in standard media. After fermentation the cells were heat-treated to release the periplasm content into the media. The constructs released into the medium were recovered by microfiltration with a membrane having a 0.2 μm pore size.

Each construct, now in the permeate from the filtration step, was purified by affinity. The permeate was loaded onto a chromatography medium containing immobilized IgG (IgG Sepharose 6FF, GE Healthcare). The loaded product was washed with phosphate buffered saline and eluted by lowering the pH.

The elution pool was adjusted to a neutral pH (pH 8) and reduced by addition of dithiothreitol. The sample was then loaded onto an anion exchanger. After a wash step the construct was eluted in a NaCl gradient to separate it from any contaminants. The elution pool was concentrated by ultrafiltration to 40-50 mg/ml. It should be noted that the successful affinity purification of a construct on an immobilized IgG medium indicates that the construct in question has a high affinity to IgG.

The purified ligands were analyzed with RPC LC-MS to determine the purity and to ascertain that the molecular weight corresponded to the expected (based on the amino acid sequence).

Example 1

The purified monomeric ligands listed in Table 1, further comprising for SEQ ID NO 8-16, 23-28 and 36-48 an AQGT leader sequence at the N-terminus and a cysteine at the C terminus, were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 200-1500 RU in a Biacore surface plasmon resonance (SPR) instrument (GE Healthcare, Sweden). To follow the IgG binding capacity of the immobilized surface 1 mg/ml human polyclonal IgG (Gammanorm) was flowed over the chip and the signal strength (proportional to the amount of binding) was noted. The surface was then cleaned-in-place (CIP), i.e. flushed with 500 mM NaOH for 10 minutes at room temperature (22+/−2° C.). This was repeated for 96-100 cycles and the immobilized ligand alkaline stability was followed as the remaining IgG binding capacity (signal strength) after each cycle. The results are shown in Table 1 and indicate that at least the ligands Zvar(N11K)1, Zvar(N11E)1, Zvar(N11Y)1, Zvar(N11T)1, Zvar(N11F)1, Zvar(N11L)1, Zvar(N11W)1, ZN11I)1, Zvar(N11M)1, Zvar(N11V)1, Zvar(N11A)1, Zvar(N11H)1, Zvar(N11R)1, Zvar(N11E,Q32A)1, Zvar(N11E,Q32E,Q40E)1 and Zvar(N11E,Q32E,K50R)1, Zvar(Q9A,N11E,N43A)1, Zvar(Q9A,N11E,N28A,N43A)1, Zvar(Q9A,N11E,Q40V,A42K,N43E,L44I)1, Zvar(Q9A,N11E,Q40V,A42K,N43A,L44I)1, Zvar(Q9A,N11E,N28A,Q40V,A42K,N43A,L44I)1, Zvar(N11K,H18K,S33K,D37E,A42R,N43A,L44I, K50R,L51Y)1, Zvar(Q9A,N11K,H18K,S33K,D37E,A42R,N43A,L44I,K50R,L51Y)1, Zvar(N11K, H18K, D37E, A42R, N43A, L44I)1, Zvar(Q9A, N11K, H18K, D37E, A42R, N43A, L44I)1 and Zvar(Q9A, N11K, H18K, D37E, A42R, N43A, L44I, K50R)1, as well as the varieties of Zvar(Q9A,N11E,Q40V,A42K,N43A,L44I)1 having G,S, Y, Q, T, N, F, L, W, I, M, V, D, E, H, R or K in position 29, the varieties of Zvar(Q9A,N11E,Q40V,A42K,N43A,L44I)1 having F, Y, W, K or R in position 53 and the varieties of Zvar(Q9A,N11E,Q40V,A42K,N43A,L44I)1 where Q9, Q40, A42 or N43 has been deleted, have an improved alkali stability compared to the parental structure Zvar1, used as the reference. Further, the ligands B(Q9A, N11E,Q40V,A42K,N43A,L44I)1 and C(Q9A,N11E, E43A)1 have an improved stability compared to the parental B and C domains, used as references.

TABLE 1

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(N11E, Q32A)1 | SEQ ID NO 12 | 57% | 55% | 1.036 |
| Zvar(N11E)1 | SEQ ID NO 13 | 59% | 55% | 1.073 |

TABLE 1-continued

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(N11E, Q32E, Q40E)1 | SEQ ID NO 14 | 52% | 51% | 1.020 |
| Zvar(N11E, Q32E, K50R)1 | SEQ ID NO 15 | 53% | 51% | 1.039 |
| Zvar(N11K)1 | SEQ ID NO 16 | 62% | 49% | 1.270 |
| Zvar(N11Y)1 | SEQ ID NO 38 | 55% | 46% | 1.20 |
| Zvar(N11T)1 | SEQ ID NO 39 | 50% | 46% | 1.09 |
| Zvar(N11F)1 | SEQ ID NO 40 | 55% | 46% | 1.20 |
| Zvar(N11L)1 | SEQ ID NO 41 | 57% | 47% | 1.21 |
| Zvar(N11W)1 | SEQ ID NO 42 | 57% | 47% | 1.21 |
| Zvar(N11I)1 | SEQ ID NO 43 | 57% | 47% | 1.21 |
| Zvar(N11M)1 | SEQ ID NO 44 | 58% | 46% | 1.26 |
| Zvar(N11V)1 | SEQ ID NO 45 | 56% | 46% | 1.22 |
| Zvar(N11A)1 | SEQ ID NO 46 | 58% | 46% | 1.26 |
| Zvar(N11H)1 | SEQ ID NO 47 | 57% | 46% | 1.24 |
| Zvar(N11R)1 | SEQ ID NO 48 | 59% | 46% | 1.28 |
| Zvar(Q9A, N11E, N43A)1 | SEQ ID NO 8 | 70% | 47% | 1.49 |
| Zvar(Q9A, N11E, N28A, N43A)1 | SEQ ID NO 9 | 68% | 47% | 1.45 |
| Zvar(Q9A, N11E, Q40V, A42K, N43E, L44I)1 | SEQ ID NO 10 | 67% | 47% | 1.43 |
| Zvar(Q9A, N11E, Q40V, A42K, N43A, L44I)1 | SEQ ID NO 11 | 66% | 47% | 1.40 |
| Zvar(Q9A, N11E, N28A, Q40V, A42K, N43A, L44I)1 | SEQ ID NO 24 | 65% | 48% | 1.35 |
| Zvar(N11K, H18K, S33K, D37E, A42R, N43A, L44I, K50R, L51Y)1 | SEQ ID NO 23 | 67% | 46% | 1.46 |
| Zvar(Q9A, N11K, H18K, S33K, D37E, A42R, N43A, L44I, K50R, L51Y)1 | SEQ ID NO 25 | 59% | 46% | 1.28 |
| Zvar(N11K, H18K, D37E, A42R, N43A, L44I)1 | SEQ ID NO 26 | 59% | 45% | 1.31 |
| Zvar(Q9A, N11K, H18K, D37E, A42R, N43A, L44I)1 | SEQ ID NO 27 | 63% | 45% | 1.40 |
| Zvar(Q9A, N11K, H18K, D37E, A42R, N43A, L44I, K50R)1 | SEQ ID NO 28 | 67% | 45% | 1.49 |
| B(Q9A, N11E, Q40V, A42K, N43A, L44I)1 | SEQ ID NO 36 | 39% | 35% | 1.11 |
| C(Q9A, N11E, E43A)1 | SEQ ID NO 37 | 60% | 49% | 1.22 |
| Zvar(Q9A, N11E, A29G, Q40V, A42K, N43A, L44I)1 | SEQ ID NO: 54 | 69% | 48% | 1.44 |
| Zvar(Q9A, N11E, A29S, Q40V, A42K, N43A, L44I)1 | SEQ ID NO: 55 | 66% | 48% | 1.38 |
| Zvar(Q9A, N11E, A29Y, Q40V, A42K, N43A, L44I)1 | SEQ ID NO: 56 | 61% | 48% | 1.27 |
| Zvar(Q9A, N11E, A29Q, Q40V, A42K, N43A, L44I)1 | SEQ ID NO: 57 | 60% | 47% | 1.28 |
| Zvar(Q9A, N11E, A29T, Q40V, A42K, N43A, L44I)1 | SEQ ID NO: 58 | 60% | 47% | 1.28 |
| Zvar(Q9A, N11E, A29N, Q40V, A42K, N43A, L44I)1 | SEQ ID NO: 59 | 61% | 47% | 1.30 |
| Zvar(Q9A, N11E, A29F, Q40V, A42K, N43A, L44I)1 | SEQ ID NO 60 | 62% | 46% | 1.35 |

TABLE 1-continued

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(Q9A, N11E, A29L, Q40V, A42K, N43A, L44I)1 | SEQ ID NO 61 | 61% | 46% | 1.33 |
| Zvar(Q9A, N11E, A29W, Q40V, A42K, N43A, L44I)1 | SEQ ID NO 62 | 60% | 46% | 1.30 |
| Zvar(Q9A, N11E, A29I, Q40V, A42K, N43A, L44I)1 | SEQ ID NO 63 | 58% | 47% | 1.23 |
| Zvar(Q9A, N11E, A29M, Q40V, A42K, N43A, L44I)1 | SEQ ID NO 64 | 62% | 47% | 1.32 |
| Zvar(Q9A, N11E, A29V, Q40V, A42K, N43A, L44I)1 | SEQ ID NO 65 | 62% | 47% | 1.32 |
| Zvar(Q9A, N11E, A29D, Q40V, A42K, N43A, L44I)1 | SEQ ID NO 66 | 56% | 47% | 1.19 |
| Zvar(Q9A, N11E, A29E, Q40V, A42K, N43A, L44I)1 | SEQ ID NO 67 | 57% | 47% | 1.21 |
| Zvar(Q9A, N11E, A29H, Q40V, A42K, N43A, L44I)1 | SEQ ID NO 68 | 57% | 47% | 1.21 |
| Zvar(Q9A, N11E, A29R, Q40V, A42K, N43A, L44I)1 | SEQ ID NO 69 | 58% | 46% | 1.26 |
| Zvar(Q9A, N11E, A29K, Q40V, A42K, N43A, L44I)1 | SEQ ID NO 70 | 59% | 46% | 1.28 |
| Zvar(Q9A, N11E, Q40V, A42K, N43A, L44I, D53F)1 | SEQ ID NO 71 | 58% | 46% | 1.26 |
| Zvar(Q9A, N11E, Q40V, A42K, N43A, L44I, D53Y)1 | SEQ ID NO 72 | 59% | 46% | 1.28 |
| Zvar(Q9A, N11E, Q40V, A42K, N43A, L44I, D53W)1 | SEQ ID NO 73 | 62% | 46% | 1.35 |
| Zvar(Q9A, N11E, Q40V, A42K, N43A, L44I, D53K)1 | SEQ ID NO 74 | 65% | 46% | 1.41 |
| Zvar(Q9A, N11E, Q40V, A42K, N43A, L44I, D53R)1 | SEQ ID NO 75 | 60% | 46% | 1.30 |
| Zvar(Q9del, N11E, Q40V, A42K, N43A, L44I)1 | SEQ ID NO 76 | 60% | 46% | 1.30 |
| Zvar(Q9A, N11E, Q40del, A42K, N43A, L44I)1 | SEQ ID NO 77 | 59% | 46% | 1.28 |
| Zvar(Q9A, N11E, Q40V, A42del, N43A, L44I)1 | SEQ ID NO 78 | 57% | 46% | 1.24 |
| Zvar(Q9A, N11E, Q40V, A42K, N43del, L44I)1 | SEQ ID NO 79 | 55% | 46% | 1.20 |

The Biacore experiment can also be used to determine the binding and dissociation rates between the ligand and IgG. This was used with the set-up as described above and with an IgG1 monoclonal antibody as probe molecule. For the reference Zvar1, the on-rate ($10^5$ M$^{-1}$ s$^{-1}$) was 3.1 and the off-rate ($10^5$ s$^{-1}$) was 22.1, giving an affinity (off-rate/on-rate) of 713 pM. For Zvar(Q9A,N11E,Q40V,A42K,N43A, L44I)1 (SEQ ID NO. 11), the on-rate was 4.1 and the off-rate 43.7, with affinity 1070 pM. The IgG affinity was thus somewhat higher for the mutated variant.

Example 2

The purified dimeric, tetrameric and hexameric ligands listed in Table 2 were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 200-1500 RU in a Biacore instrument (GE Healthcare, Sweden). To follow the IgG binding capacity of the immobilized surface 1 mg/ml human polyclonal IgG (Gammanorm) was flowed over the chip and the signal strength (proportional to the amount of binding) was noted. The surface was then cleaned-in-place (CIP), i.e. flushed with 500 mM NaOH for 10 minutes at room temperature (22+/−2° C.). This was repeated for 300 cycles and the immobilized ligand alkaline stability was followed as the remaining IgG binding capacity (signal strength) after each cycle. The results are shown in Table 2 and in FIG. 2 and indicate that at least the ligands Zvar(Q9A,N11E,N43A)4, Zvar(Q9A,N11E,N28A,N43A)4, Zvar(Q9A,N11E,Q40V,A42K,N43E,L44I)4 and Zvar(Q9A, N11E,Q40V,A42K,N43A,L44I)4, Zvar(Q9A,N11E,D37E, Q40V,A42K,N43A,L44I)4 and Zvar(Q9A,N11E,D37E, Q40V,A42R,N43A,L44I)4 have an improved alkali stability compared to the parental structure Zvar4, which was used as a reference. The hexameric ligand Zvar(Q9A,N11E,Q40V, A42K,N43A,L44I)6 also has improved alkali stability compared to the parental structure Zvar6, used as a reference. Further, Zvar(Q9A,N11E,Q40V,A42K,N43A,L44I) dimers with deletions of a) D2,A3,K4; b) K58,V1,D2; c) P57,K58, V1,D2,A3; d) K4,F5,D6,K7,E8; e) A56,P57,K58; V1,D2, A3 or f) V1,D2,A3,K4,F5,D6,K7,E8 from the linker region between the two monomer units have improved alkali stability compared to the parental structure Zvar2, used as a reference. Also Zvar(Q9A,N11E,Q40V,A42K,N43A,L44I) dimers with an insertion of YEDG between K58 and V1 in the linker region have improved alkali stability compared to Zvar2.

TABLE 2

| Ligand | SEQ ID NO: | Remaining capacity 100 cycles (%) | Capacity relative to ref. 100 cycles | Remaining capacity 200 cycles (%) | Capacity relative to ref. 200 cycles | Remaining capacity 300 cycles (%) | Capacity relative to ref. 300 cycles |
|---|---|---|---|---|---|---|---|
| Dimeric, tetrameric and hexameric ligands, evaluated by Biacore (0.5M NaOH). | | | | | | | |
| Zvar4 | 21 | 67 | 1 | 36 | 1 | 16 | 1 |
| Zvar(Q9A, N11E, N43A)4 | 17 | 81 | 1.21 | 62 | 1.72 | 41 | 2.56 |
| Zvar(Q9A, N11E, N28A, N43A)4 | 18 | 80 | 1.19 | 62 | 1.72 | 42 | 2.62 |
| Zvar(Q9A, N11E, Q40V, A42K, N43E, L44I)4 | 19 | 84 | 1.25 | 65 | 1.81 | 48 | 3.00 |
| Zvar(Q9A, N11E, Q40V, A42K, N43A, L44I)4 | 20 | 90 | 1.34 | 74 | 2.06 | 57 | 3.56 |
| Zvar(Q9A, N11E, N28A, Q40V, A42K, N43A, L44I)4 | 32 | 84 | 1.24 | Not tested | Not tested | Not tested | Not tested |
| Zvar(Q9A, N11E, Q40V, A42K, N43A, L44I)6 | 33 | 87 | 1.30 | Not tested | Not tested | Not tested | Not tested |
| Zvar(Q9A, N11E, D37E, Q40V, A42K, N43A, L44I)4 | 34 | 81 | 1.13 | Not tested | Not tested | Not tested | Not tested |
| Zvar(Q9A, N11E, D37E, Q40V, A42R, N43A, L44I)4 | 35 | 84 | 1.17 | Not tested | Not tested | Not tested | Not tested |
| Zvar(Q9A, N11E, Q40V, A42K, N43A, L44I)2 with D2, A3 and K4 in linker deleted | 80 | 70 | 1.27 | Not tested | Not tested | Not tested | Not tested |
| Zvar(Q9A, N11E, Q40V, A42K, N43A, L44I)2 with K58, V1 and D2 in linker deleted | 81 | 76 | 1.38 | Not tested | Not tested | Not tested | Not tested |
| Zvar(Q9A, N11E, Q40V, A42K, N43A, L44I)2 with P57, K58, V1, D2 and A3 in linker deleted | 82 | 74 | 1.35 | Not tested | Not tested | Not tested | Not tested |
| Zvar(Q9A, N11E, Q40V, A42K, N43A, L44I)2 with K4, F5, D6, K7 and E8 in linker deleted | 83 | 70 | 1.30 | Not tested | Not tested | Not tested | Not tested |
| Zvar(Q9A, N11E, Q40V, A42K, N43A, L44I)2 with A56, P57 and K58 in linker deleted | 84 | 68 | 1.26 | Not tested | Not tested | Not tested | Not tested |
| Zvar(Q9A, N11E, Q40V, A42K, N43A, L44I)2 with V1, D2 and A3 in linker deleted | 85 | 75 | 1.39 | Not tested | Not tested | Not tested | Not tested |
| Zvar(Q9A, N11E, Q40V, A42K, N43A, L44I)2 with V1, D2, A3, K4, F5, D6, K7 and E8 in linker deleted | 86 | 62 | 1.13 | Not tested | Not tested | Not tested | Not tested |
| Zvar(Q9A, N11E, Q40V, A42K, N43A, L44I)2 with YEDG inserted in linker between K58 and V1 | 87 | 72 | 1.31 | Not tested | Not tested | Not tested | Not tested |
| Zvar2 | 88 | 55 | 1 | Not tested | Not tested | Not tested | Not tested |

Example 3

Example 2 was repeated with 100 CIP cycles of three ligands using 1 M NaOH instead of 500 mM as in Example 2. The results are shown in Table 3 and show that all three ligands have an improved alkali stability also in 1M NaOH, compared to the parental structure Zvar4 which was used as a reference.

TABLE 3

Tetrameric ligands, evaluated by Biacore (1M NaOH).

| Ligand | Sequence | Remaining capacity 100 cycles (%) | Capacity relative to ref. 100 cycles |
|---|---|---|---|
| Zvar4 | SEQ ID NO 21 | 27 | 1 |
| Zvar(Q9A, N11E, N28A, N43A)4 | SEQ ID NO 18 | 55 | 2.04 |
| Zvar(Q9A, N11E, Q40V, A42K, N43E, L44I)4 | SEQ ID NO 19 | 54 | 2.00 |
| Zvar(Q9A, N11E, Q40V, A42K, N43A, L44I)4 | SEQ ID NO 20 | 56 | 2.07 |

Example 4

Figure 3:
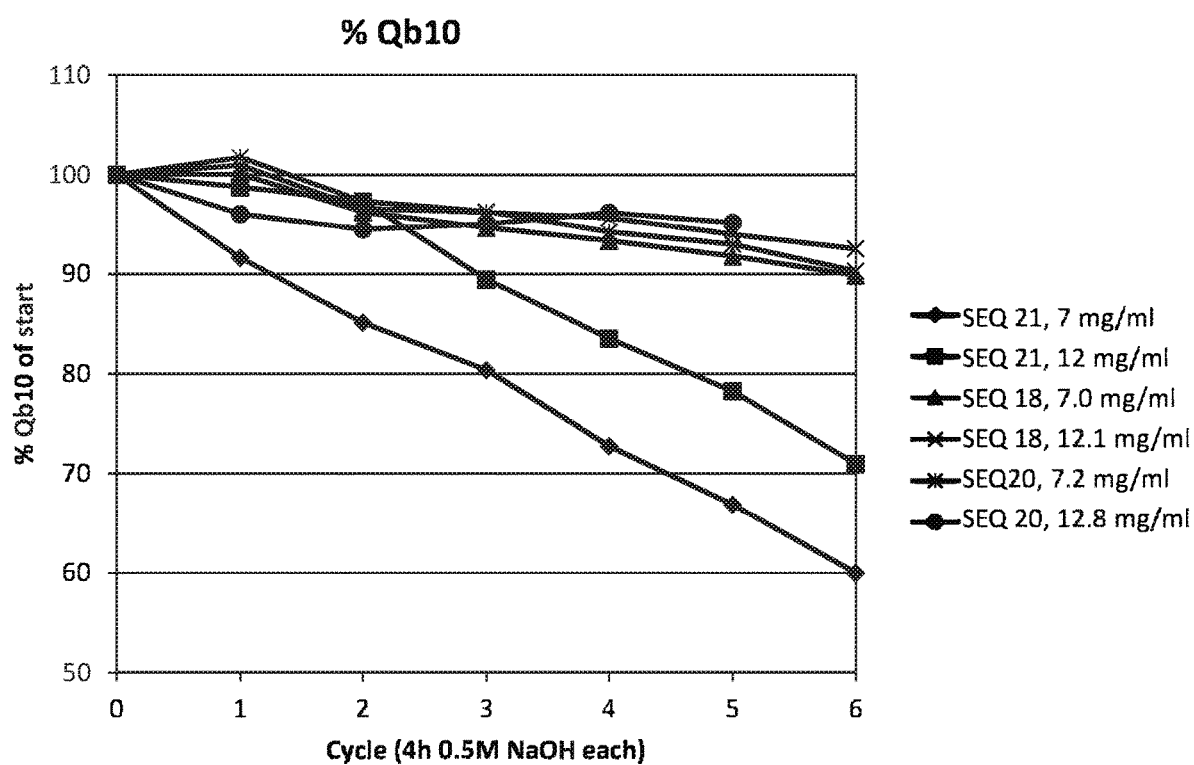
FIG. 3 shows results from Example 4 for the alkali stability (0.5 M NaOH) of parental and mutated tetrameric Zvar (SEQ ID NO 7) polypeptide variants coupled to agarose beads.

The purified tetrameric ligands of Table 2 (all with an additional N-terminal cysteine) were immobilized on agarose beads using the methods described below and assessed for capacity and stability. The results are shown in Table 4 and FIG. 3.

TABLE 4

Matrices with tetrametric ligands, evaluated in columns (0.5M NaOH).

| Ligand | SEQ ID NO. | Ligand content (mg/ml) | Initial IgG capacity Qb10 (mg/ml) | Remaining IgG capacity Qb10 after six 4 h cycles (mg/ml) | Remaining IgG capacity after six 4 h cycles (%) | Capacity retention relative to ref. after six 4 h cycles |
|---|---|---|---|---|---|---|
| Zvar4 | 21 | 7 | 52.5 | 36.5 | 60 | 1 |
| Zvar4 | 21 | 12 | 61.1 | 43.4 | 71 | 1 |
| Zvar(Q9A, N11E, N28A, N43A)4 | 18 | 7.0 | 49.1 | 44.1 | 90 | 1.50 |
| Zvar(Q9A, N11E, N28A, N43A)4 | 18 | 12.1 | 50.0 | 46.2 | 93 | 1.31 |
| Zvar(Q9A, N11E, Q40V, A42K, N43A, L44I)4 | 20 | 7.2 | 49.0 | 44.2 | 90 | 1.50 |
| Zvar(Q9A, N11E, Q40V, A42K, N43A, L44I)4 | 20 | 12.8 | 56.3 | 53.6 | 95 | 1.34 |
| Zvar(N11K, H18K, S33K, D37E, A42R, N43A, L44I, K50R, L51Y)4 | 30 | 9.7 | 56.3 | 52.0 | 92 | 1.53 |
| Zvar(Q9A, N11K, H18K, D37E, A42R)4 | 31 | 10.8 | 56.9 | 52.5 | 92 | 1.30 |

Activation

The base matrix used was rigid cross-linked agarose beads of 85 micrometers (volume-weighted, d50V) median diameter, prepared according to the methods of U.S. Pat. No. 6,602,990, hereby incorporated by reference in its entirety, and with a pore size corresponding to an inverse gel filtration chromatography Kay value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750, hereby incorporated by reference in its entirety. All buffers used in the experiments had been degassed by nitrogen gas for at least 5-10 min. The ligand content of the gels could be controlled by varying the amount and concentration of the ligand solution.

After immobilization the gels were washed 3×GV with distilled water. The gels+1 GV {0.1 M phosphate/1 mM EDTA/10% thioglycerol pH 8.6} was mixed and the tubes were left in a shaking table at room temperature overnight. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

Protein

Gammanorm 165 mg/ml (Octapharma), diluted to 2 mg/ml in Equilibration buffer.

Equilibration Buffer

PBS Phosphate buffer 10 mM+0.14 M NaCl+0.0027 M KCl, pH 7.4 (Medicago)

Adsorption Buffer

PBS Phosphate buffer 10 mM+0.14 M NaCl+0.0027 M KCl, pH 7.4 (Medicago)

Elution Buffers 100 mM acetate pH 2.9

Dynamic Binding Capacity 2 ml of resin was packed in TRICORN™ 5 100 columns. The breakthrough capacity was determined with an ÄKTA-Explorer 10 system at a residence time of 6 minutes (0.33 ml/min flow rate). Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with 5 column volumes (CV) equilibration buffer at flow rate 0.5 ml/min. The protein was eluted with 5 CV elution buffer at a flow rate of 0.5 ml/min. Then the column was cleaned with 0.5M NaOH at flow rate 0.2 ml/min and re-equilibrated with equilibration buffer.

For calculation of breakthrough capacity at 10%, the equation below was used. That is the amount of IgG that is loaded onto the column until the concentration of IgG in the column effluent is 10% of the IgG concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
$A(V)$=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) at 10% breakthrough was calculated. The dynamic binding capacity (DBC) was calculated for 10 and 80% breakthrough.

CIP—0.5 M NaOH

The 10% breakthrough DBC (Qb10) was determined both before and after repeated exposures to alkaline cleaning solutions. Each cycle included a CIP step with 0.5 M NaOH pumped through the column at a rate of 0.5/min for 20 min, after which the column was left standing for 4 h. The exposure took place at room temperature (22+/−2° C.). After this incubation, the column was washed with equilibration buffer for 20 min at a flow rate of 0.5 ml/min. Table 4 shows the remaining capacity after six 4 h cycles (i.e. 24 h cumulative exposure time to 0.5 M NaOH), both in absolute numbers and relative to the initial capacity.

Example 5

Figure 4:
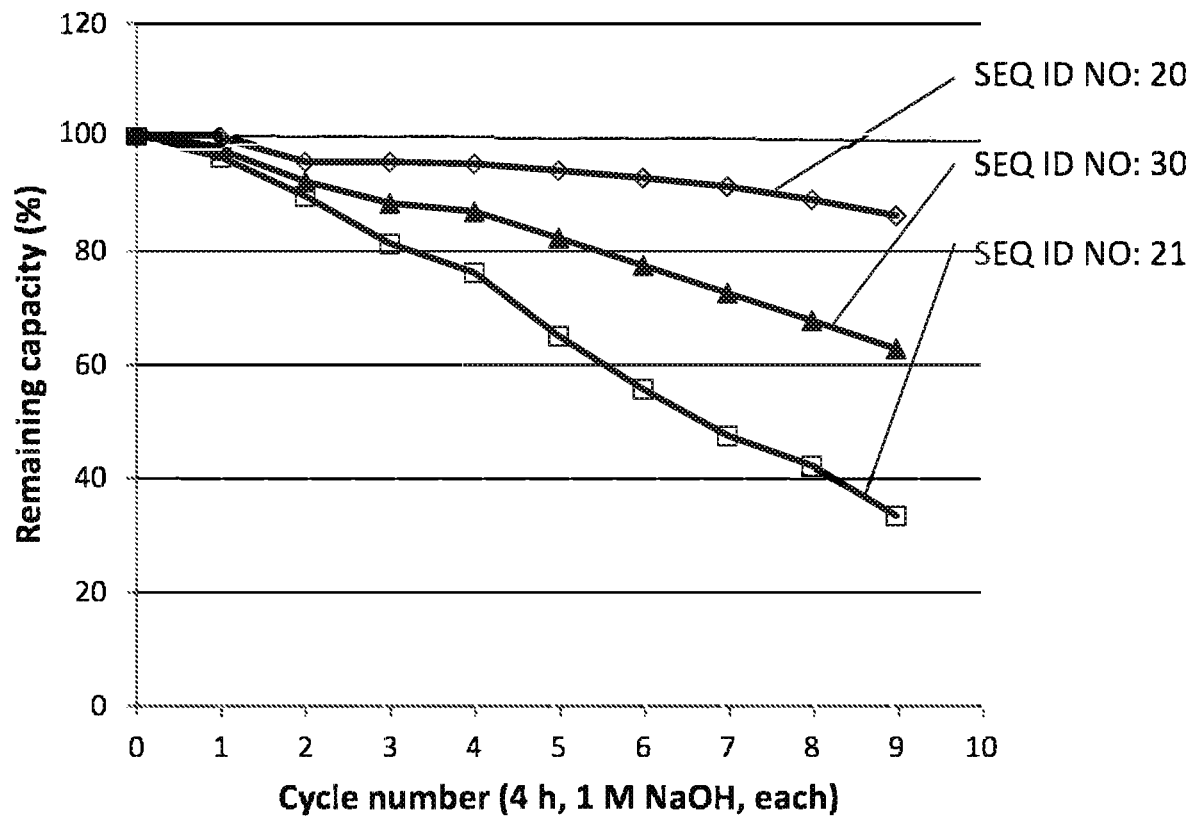
FIG. 4 shows results from Example 4 for the alkali stability (1.0 M NaOH) of parental and mutated tetrameric Zvar (SEQ ID NO 7) polypeptide variants coupled to agarose beads.

Example 4 was repeated with the tetrameric ligands shown in Table 5, but with 1.0 M NaOH used in the CIP steps instead of 0.5 M. The results are shown in Table 5 and in FIG. 4.

Example 6

Base Matrices

The base matrices used were a set of rigid cross-linked agarose bead samples of 59-93 micrometers (volume-weighted, d50V) median diameter (determined on a Malvern Mastersizer 2000 laser diffraction instrument), prepared according to the methods of U.S. Pat. No. 6,602,990 and with a pore size corresponding to an inverse gel filtration chromatography Kd value of 0.62-0.82 for dextran of Mw 110 kDa, according to the methods described above, using HR10/30 columns (GE Healthcare) packed with the prototypes in 0.2 M NaCl and with a range of dextran fractions as probe molecules (flow rate 0.2 ml/min). The dry weight of the bead samples ranged from 53 to 86 mg/ml, as determined by drying 1.0 ml drained filter cake samples at 105° C. over night and weighing.

TABLE 6

| Base matrix samples | | | |
|---|---|---|---|
| Base matrix | Kd | d50v (μm) | Dry weight (mg/ml) |
| A18 | 0.704 | 59.0 | 56.0 |
| A20 | 0.70 | 69.2 | 55.8 |
| A27 | 0.633 | 87.2 | 74.2 |
| A28 | 0.638 | 67.4 | 70.2 |
| A29 | 0.655 | 92.6 | 57.5 |
| A32 | 0.654 | 73.0 | 70.5 |
| A33 | 0.760 | 73.1 | 55.5 |
| A38 | 0.657 | 70.9 | 56.2 |
| A39 | 0.654 | 66.0 | 79.1 |
| A40 | 0.687 | 64.9 | 74.9 |
| A41 | 0.708 | 81.7 | 67.0 |
| A42 | 0.638 | 88.0 | 59.4 |
| A43 | 0.689 | 87.5 | 77.0 |
| A45 | 0.670 | 56.6 | 66.0 |
| A52 | 0.620 | 53.10 | 63.70 |
| A53 | 0.630 | 52.6 | 86.0 |
| A54 | 0.670 | 61.3 | 75.3 |
| A55 | 0.640 | 62.0 | 69.6 |
| A56 | 0.740 | 61.0 | 56.0 |
| A56-2 | 0.740 | 51.0 | 56.0 |
| A62a | 0.788 | 48.8 | 70.1 |
| A62b | 0.823 | 50.0 | 46.9 |
| A63a | 0.790 | 66.8 | 59.6 |
| A63b | 0.765 | 54.0 | 79.0 |
| A65a | 0.796 | 58.0 | 60.0 |
| A65b | 0.805 | 57.3 | 46.0 |
| B5 | 0.793 | 69.0 | 84.4 |
| C1 | 0.699 | 71.0 | 73.4 |
| C2 | 0.642 | 66.5 | 81.1 |
| C3 | 0.711 | 62.0 | 82.0 |
| C4 | 0.760 | 62.0 | 82.0 |
| H31 | 0.717 | 82.0 | 59.0 |
| H35 | 0.710 | 81.1 | 61.0 |
| H40 | 0.650 | 52.8 | 65.0 |
| I1 | 0.640 | 50.0 | 67.0 |

TABLE 5

| Matrices with tetrameric ligands, evaluated in columns - 1.0M NaOH. | | | | | |
|---|---|---|---|---|---|
| Ligand | SEQ ID NO. | Ligand content (mg/ml) | Initial IgG capacity Qb10 (mg/ml) | Remaining IgG capacity Qb10 after six 4 h cycles (mg/ml) | Remaining IgG capacity after six 4 h cycles (%) | Capacity retention relative to ref. after six 4 h cycles |
| Zvar4 | 21 | 12 | 60.1 | 33.5 | 56 | 1 |
| Zvar(Q9A, N11E, Q40V, A42K, N43A, L44I)4 | 20 | 12.8 | 60.3 | 56.0 | 93 | 1.67 |
| Zvar(N11K, H18K, S33K, D37E, A42R, N43A, L44I, K50R, L51Y)4 | 30 | 9.7 | 62.1 | 48.1 | 77 | 1.44 |

TABLE 6-continued

Base matrix samples

| Base matrix | Kd | d50v (μm) | Dry weight (mg/ml) |
|---|---|---|---|
| 41 | 0.702 | 81.6 | 60.6 |
| 517 | 0.685 | 87.9 | 64.4 |
| 106 | 0.692 | 86.7 | 64.6 |
| 531C | 0.661 | 51.7 | 63.8 |
| P10 | 0.741 | 59.3 | 70.0 |
| S9 | 0.736 | 64.1 | 72.2 |

Coupling 100 ml base matrix was washed with 10 gel volumes distilled water on a glass filter. The gel was weighed (1 g=1 ml) and mixed with 30 ml distilled water and 8.08 g NaOH (0.202 mol) in a 250 ml flask with an agitator. The temperature was adjusted to 27+/−2° C. in a water bath. 16 ml epichlorohydrin (0.202 mol) was added under vigorous agitation (about 250 rpm) during 90+/−10 minutes. The reaction was allowed to continue for another 80+/−10 minutes and the gel was then washed with >10 gel volumes distilled water on a glass filter until neutral pH was reached. This activated gel was used directly for coupling as below.

To 16.4 mL of ligand solution (50 mg/mL) in a 50 ml Falcon tube, 139 mg NaHCO$_3$, 17.4 mg Na$_2$CO$_3$, 143.8 mg NaCl and 141 mg EDTA, was added. The Falcon tube was placed on a roller table for 5-10 min, and then 63 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750 5.2.2, although with considerably higher ligand amounts (see below). All buffers used in the experiments had been degassed by nitrogen gas for at least 5-10 min. The ligand content of the gels was controlled by varying the amount and concentration of the ligand solution, adding 5-20 mg ligand per ml gel. The ligand was either a tetramer (SEQ ID NO. 20) or a hexamer (SEQ ID NO. 33) of an alkali-stabilized mutant.

After immobilization the gels were washed 3×GV with distilled water. The gels+1 GV {0.1 M phosphate/1 mM EDTA/10% thioglycerol pH 8.6} was mixed and the tubes were left in a shaking table at room temperature overnight. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

Evaluation

The Qb10% dynamic capacity for polyclonal human IgG at 2.4 and 6 min residence time was determined as outlined in Example 4.

TABLE 7

Prototype results

| Prototype | Base matrix | Ligand content (mg/ml) | Multimer | Qb10% 2.4 min (mg/ml) | Qb10% 6 min (mg/ml) |
|---|---|---|---|---|---|
| N1 | A38 | 7.45 | tetramer | 44.4 | 58.25 |
| N2 | A20 | 7.3 | tetramer | 45.12 | 57.21 |
| N3 | A42 | 6.72 | tetramer | 33.56 | 50.02 |
| N4 | A29 | 7.3 | tetramer | 36.34 | 51.8 |
| N5 | A28 | 7.9 | tetramer | 42.38 | 58.25 |
| N6 | A39 | 6.96 | tetramer | 41.88 | 54.67 |
| N7 | A27 | 7.5 | tetramer | 29.19 | 48.73 |
| N8 | A43 | 6.99 | tetramer | 33.43 | 49.79 |
| N9 | A38 | 11.34 | tetramer | 48.1 | 72.78 |
| N10 | A20 | 10.6 | tetramer | 50.66 | 70.07 |
| N11 | A42 | 11.1 | tetramer | 32.25 | 57.78 |
| N12 | A29 | 11 | tetramer | 34.85 | 64.68 |
| N13 | A28 | 11.9 | tetramer | 39.92 | 63.75 |
| N14 | A39 | 10.48 | tetramer | 44.37 | 64.79 |
| N15 | A27 | 12.1 | tetramer | 24.8 | 55.56 |
| N16 | A43 | 10.51 | tetramer | 31.82 | 58.04 |
| N17 | A41 | 8.83 | tetramer | 38.5 | 56.8 |
| N18 | A41 | 8.83 | tetramer | 37.84 | 58.6 |
| N19 | A41 | 8.83 | tetramer | 35.06 | 57.23 |
| N20 | A41 | 5.0 | tetramer | 35.64 | 46.04 |
| N21 | A41 | 13.0 | tetramer | 34.95 | 62.23 |
| N22 | A40 | 13.15 | tetramer | 56.85 | 71.09 |
| N23 | A33 | 7.33 | tetramer | 48.69 | 55.76 |
| N24 | A40 | 11.03 | tetramer | 54.96 | 73.8 |
| 033A | A38 | 7.5 | tetramer | 44 | 58 |
| 033B | A38 | 11.3 | tetramer | 48 | 73 |
| 097A | A20 | 7.3 | tetramer | 45 | 57 |
| 097B | A20 | 10.6 | tetramer | 51 | 70 |
| 003A | A28 | 7.9 | tetramer | 42 | 58 |
| 003B | A28 | 11.9 | tetramer | 40 | 64 |
| 003C | A28 | 15.8 | tetramer | 37 | 67 |
| 038A | A39 | 7.0 | tetramer | 42 | 55 |
| 038B | A39 | 10.5 | tetramer | 44 | 65 |
| 074 | A40 | 13.2 | tetramer | 57 | 71 |
| 093 | A33 | 7.3 | tetramer | 49 | 56 |
| 058A | A40 | 11.0 | tetramer | 55 | 74 |
| 077 | A18 | 8.2 | tetramer | 52 | 59 |
| 010 | A32 | 10.7 | tetramer | 40 | 57 |
| 099 | A32 | 13.3 | tetramer | 37 | 66 |
| 030A | B5 | 6.3 | tetramer | 32 | 38 |
| 030B | B5 | 9.6 | tetramer | 45 | 47 |
| 293A | C1 | 5.4 | tetramer | 38 | 47 |
| 293B | C1 | 10.8 | tetramer | 43 | 60 |
| 294A | C2 | 5.1 | tetramer | 39 | 46 |
| 294B | C2 | 10.5 | tetramer | 42 | 57 |
| 336A | H40 | 5.6 | tetramer | 47 | 52 |
| 336B | H40 | 9.1 | tetramer | 52 | 67 |
| 091 | A18 | 13.4 | tetramer | N/A | 63 |
| 092 | A20 | 12.8 | tetramer | 49 | 67 |
| 080 | A33 | 9.4 | tetramer | 51 | 58 |
| 089 | A40 | 6.1 | tetramer | 49 | 59 |
| 688A | A62a | 6.6 | tetramer | 41 | 46 |
| 688B | A62a | 14.8 | tetramer | 55 | 62 |
| 871 | A62a | 9.7 | tetramer | 48 | 60 |
| 934A | A63a | 6.6 | tetramer | 40 | 44 |
| 934B | A63a | 14.0 | tetramer | 48 | 56 |
| 017B | A65a | 13.1 | tetramer | 56 | 64 |
| 041A | A62b | 5.2 | tetramer | 40 | N/A |
| 041B | A62b | 11.1 | tetramer | 52 | N/A |
| 116A | A65b | 5.8 | tetramer | 42 | 46 |
| 116B | A65b | 8.8 | tetramer | 49 | 56 |
| 017A | A65a | 6.1 | tetramer | 40 | 44 |
| 387A | A62a | 6.4 | tetramer | 43 | 45 |
| 387B | A62a | 7.5 | tetramer | 47 | 56 |
| 432 | A63a | 6.1 | tetramer | 39 | 44 |
| 433A | A65a | 6.6 | tetramer | 42 | 47 |
| 433B | A65a | 13.6 | tetramer | 52 | 61 |
| 579A | I1 | 6.1 | tetramer | 45 | 51 |
| 579B | I1 | 11.2 | tetramer | 57 | 68 |
| 064A | C3 | 5.9 | tetramer | 44 | 52 |
| 064B | C3 | 9.0 | tetramer | 49 | 62 |
| 064C | C3 | 14.3 | tetramer | 51 | 70 |
| 352A | C4 | 10.1 | tetramer | 55 | 63 |
| 352B | C4 | 14.4 | tetramer | 59 | 67 |
| 066A | C3 | 6.8 | hexamer | 48 | 59 |
| 066B | C3 | 11.9 | hexamer | 51 | 73 |

TABLE 7-continued

Prototype results

| Prototype | Base matrix | Ligand content (mg/ml) | Multimer | Qb10% 2.4 min (mg/ml) | Qb10% 6 min (mg/ml) |
|---|---|---|---|---|---|
| 066C | C3 | 15.1 | hexamer | 43 | 61 |
| 353A | C4 | 11.2 | hexamer | 62 | 74 |
| 353B | C4 | 15.2 | hexamer | 57 | 82 |
| 872A | A62a | 9.6 | hexamer | 56 | 72 |
| 872B | A62a | 14.5 | hexamer | 62 | 84 |
| 869A | H40 | 6.9 | hexamer | 50 | 56 |
| 869B | H40 | 14.3 | hexamer | 56 | 75 |
| 869C | H40 | 23.0 | hexamer | 41 | 65 |
| 962A | H35 | 6.8 | hexamer | 36 | 49 |
| 962B | H35 | 12.3 | hexamer | 31 | 54 |
| 962C | H35 | 20.3 | hexamer | 20 | 43 |
| 112A | A56 | 7.9 | hexamer | 47 | 55 |
| 112B | A56 | 12.4 | hexamer | 57 | 73 |
| 112C | A56 | 19.2 | hexamer | 55 | 80 |
| 113A | A56 | 7.1 | hexamer | 48 | 57 |
| 113B | A56 | 12.4 | hexamer | 53 | 73 |
| 113C | A56 | 15.2 | hexamer | 48 | 76 |
| 212A | H31 | 6.5 | hexamer | 37 | 38 |
| 212B | H31 | 10.4 | hexamer | 50 | 61 |
| 212C | H31 | 20.0 | hexamer | 31 | 52 |
| 213A | A33 | 6.5 | hexamer | 44 | 53 |
| 213B | A33 | 10.9 | hexamer | 50 | 65 |
| 213C | A33 | 11.1 | hexamer | 50 | 68 |
| 432A | A20 | 6.4 | hexamer | 41 | 56 |
| 432B | A20 | 12.4 | hexamer | 38 | 64 |
| 432C | A20 | 21.1 | hexamer | 44 | 43 |
| 433A | A38 | 5.9 | hexamer | 47 | 57 |
| 433B | A38 | 11.6 | hexamer | 48 | 72 |
| 433C | A38 | 15.8 | hexamer | 36 | 62 |
| 742A | A54 | 6.7 | hexamer | 38 | 46 |
| 742B | A54 | 12.6 | hexamer | 45 | 52 |
| 742C | A54 | 21.1 | hexamer | 38 | 65 |
| 726A | A63b | 6.4 | hexamer | 42 | 46 |
| 726B | A63b | 10.6 | hexamer | 49 | 60 |
| 726C | A63b | 16.7 | hexamer | 53 | 69 |
| 793A | A56-2 | 6.8 | hexamer | 50 | 58 |
| 793B | A56-2 | 12.5 | hexamer | 59 | 72 |
| 793C | A56-2 | 19.2 | hexamer | 61 | 82 |
| 517 | 517 | 12.0 | tetramer* | 35 | 56 |
| 106 | 106 | 5.8 | tetramer* | 33 | 45 |
| 531C | 531C | 11.2 | tetramer* | 54 | 65 |
| P10 | P10 | 19.0 | hexamer |  | 76 |
| S9 | S9 | 18.4 | hexamer | 56 | 75 |

*SEQ ID NO 21

Example 7

Figure 5:
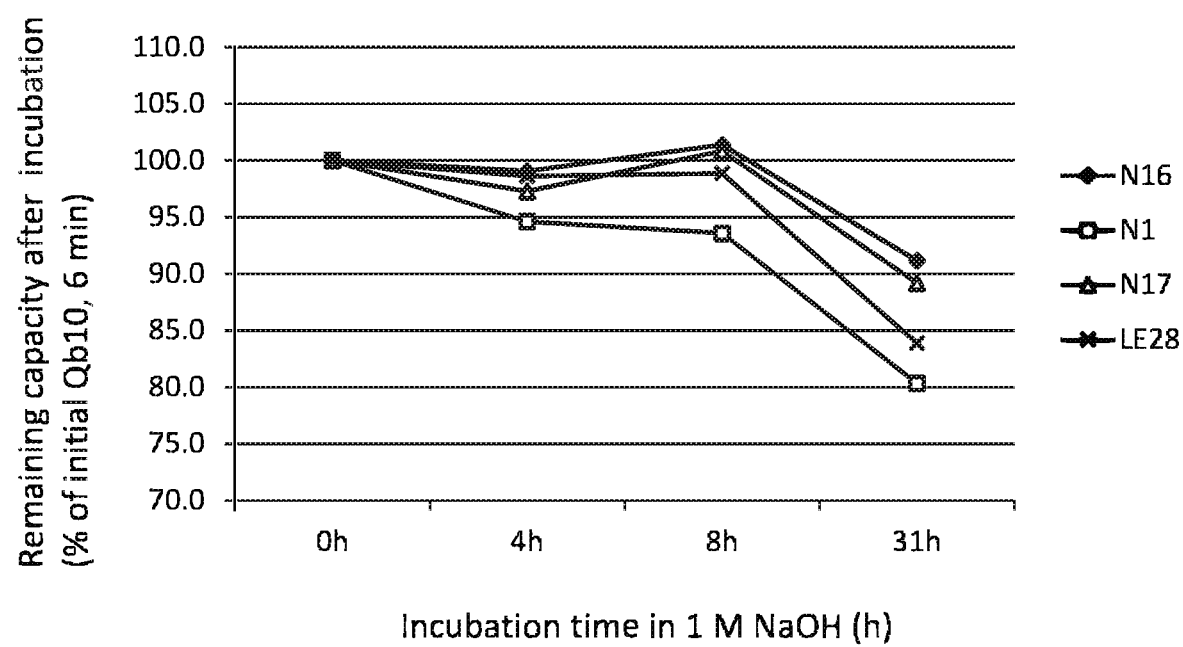
FIG. 5 shows results from Example 7 for the alkali stability (1.0 M NaOH) of agarose beads with different amounts of mutated multimer variants (SEQ ID NO. 20) coupled. The results are plotted as the relative remaining dynamic capacity (Qb10%, 6 min residence time) vs. incubation time in 1 M NaOH.
Figure 6:
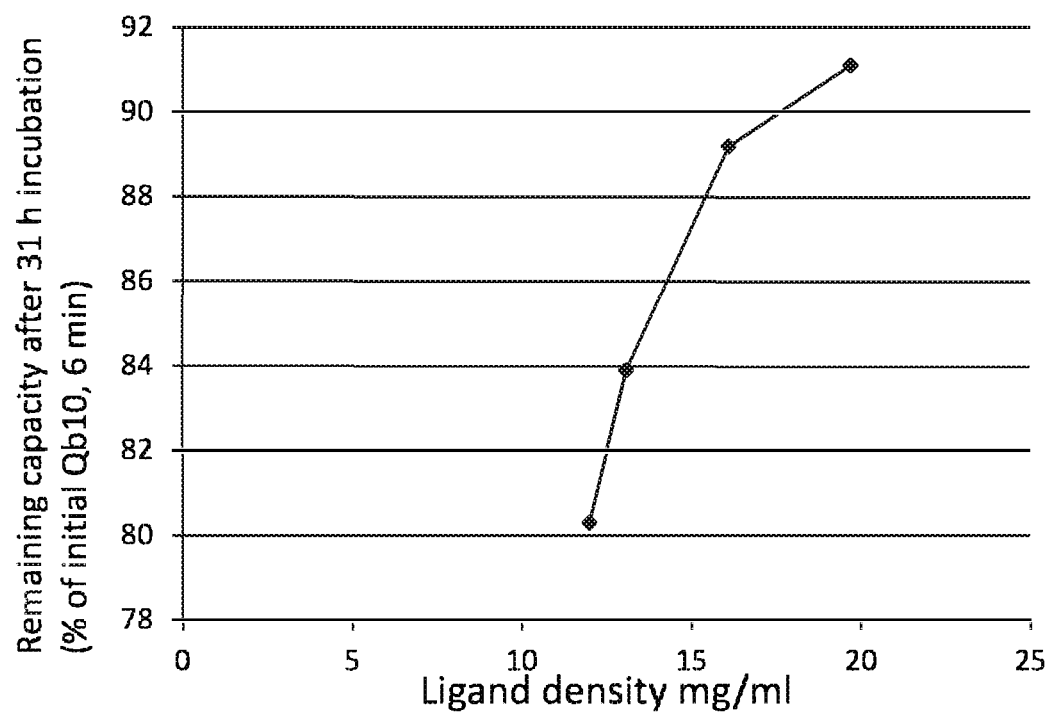
FIG. 6 shows results from Example 7 for the alkali stability (1.0 M NaOH) of agarose beads with different amounts of mutated multimer variants (SEQ ID NO. 20) coupled. The results are plotted as the relative remaining dynamic capacity (Qb10%, 6 min residence time) after 31 h incubation in 1 M NaOH vs. the ligand content of the prototypes.

A series of prototypes, prepared as above, with different ligand content (tetramer, SEQ ID NO:20) were incubated in 1 M NaOH for 4, 8 and 31 hours at 22+/−2° C. and the dynamic IgG capacity (Qb10%, 6 min residence time) was measured before and after incubation. The prototypes are shown in Table 8 and the results in FIGS. 5 and 6. It can be seen that the stability towards this harsh alkali treatment increases with increasing ligand content.

TABLE 8

Samples for incubation in 1M NaOH

| Prototype | Ligand content (mg/ml) | Qb10%, 6 min, before incubation (mg/ml) |
|---|---|---|
| N1 | 12 | 78 |
| LE28 | 13 | 79 |
| N17 | 16 | 73 |
| N16 | 20 | 73 |

Example 8

Two crosslinked agarose bead prototypes, prepared as above, with different ligand content (hexamer, SEQ ID NO:33), median bead diameter (d50,v) 62 μm and Kd 0.70 for dextran of Mw 110 kD, were evaluated with a real mAb feed. The ligand content of prototype A was 14.3 mg/ml and of prototype B 18.9 mg/ml. For comparison, the commercial product MabSelect SuRe® LX (GE Healthcare Life Sciences) was used. The resins were packed in Tricorn columns (GE Healthcare Life Sciences) to bed heights of 10 cm, giving bed volumes of 2 ml and the columns were shown to have peak asymmetry within the 0.8-1.5 interval. The sample loaded was a clarified CHO cell supernatant with 4.9 mg/ml monoclonal IgG1 antibody at physiological pH and the experimental conditions were as listed below in Table 9 (CV=column volumes, RT=residence time).

TABLE 9

Conditions for evaluation with real feed.

| Equilibration: | 3 CV 20 mM phosphate, 150 mM NaCl pH 7.4, RT = 3.4 min |
|---|---|
| Sample loading: | 43 mg mAb/ml resin, RT = 6 min |
| Wash 1: | 5 CV 20 mM phosphate, 500 mM NaCl pH 7.4, 1.5 CV at RT = 6 min and 3.5 CV at RT = 3.4 min |
| Wash 2: | 1 CV 50 mM acetate pH 6.0, RT = 3.4 min |
| Elution: | 3 CV 50 mM acetate pH 3.5, RT = 6 min, peak collected between 150 mAU-150 mAU |
| Strip: | 2 CV 100 mM acetate, RT = 3.4 min |
| CIP: | 3 CV 0.1M NaOH, RT = 6 min |
| Re-equilibration: | 5 CV 20 mM phosphate, 150 mM NaCl pH 7.4, RT = 3.4 min |

The mAb peak was collected using a UV watch function and the concentration of the mAb was determined by UV measurement at 280 nm (extinction coefficient 1.5). All absorbance detections were performed using a spectrophotometer, including the measurements for the yield calculations.

Samples for HCP (host cell protein) analyses were prepared by adding 10% Preservation buffer (0.2 M NaH$_2$PO$_4$*H$_2$O (5.3%), 0.2 M Na$_2$HPO$_4$*12 H$_2$O (94.7%), 0.5% Tween 20, 1% BSA pH 8) to the samples directly after each run made (e.g. 50 μl preservation buffer to 450 μl sample). The HCP content was measured using commercial anti-CHO antibodies (Cygnus Technologies) and a Gyrolab (Gyros AB, Sweden) work station.

The results are presented in Table 10 below and show that the performance of the prototypes is in the same range as for the commercial product. The HCP content in the feed was 331 000 ppm.

TABLE 10

Results from real feed evaluation

| Resin | Yield (%) | Elution pool (CV) | HCP in pool (ppm) |
|---|---|---|---|
| MabSelect SuRe LX | 90 | 1.5 | 914 |
| MabSelect SuRe LX | 95 | 1.6 | 1021 |
| Prototype A | 96 | 1.3 | 1076 |
| Prototype A | 95 | 1.3 | 1105 |
| Prototype B | 96 | 1.3 | 1040 |
| Prototype B | 93 | 1.3 | 1104 |

Example 9

A crosslinked agarose bead matrix prototype, prepared as above, with 14.5 mg/ml ligand (hexamer, SEQ ID NO:33), median bead diameter (d50,v) 57.4 μm, Kd 0.72 for dextran of Mw 110 kD and dry weight 70.3 mg/ml, was evaluated for elution pH with two real mAb feeds (mAb1 2.4 g/l and mAb2 4.9 g/l) IgG1, physiological pH, and a sample of polyclonal human IgG (Gammanorm, Octapharma). For comparison, the commercial product MabSelect SuRe® LX (GE Healthcare Life Sciences) was used. The resins were packed in Tricorn columns (GE Healthcare Life Sciences) to bed heights of 10 cm, giving bed volumes of 2 ml and the columns were shown to have peak asymmetry within the 0.8-1.5 interval. The samples loaded were clarified CHO cell supernatants with IgG1 mAbs at physiological pH and the experimental conditions were as listed below in Table 11 (CV=column volumes, RT=residence time).

TABLE 11

Conditions for elution pH evaluation.

| | |
|---|---|
| Equilibration: | 5 CV 20 mM phosphate, 150 mM NaCl pH 7.4, RT = 3.4 min |
| Sample loading: | 10 mg mAb/ml resin, RT = 6 min |
| Wash: | 6 CV 20 mM phosphate, 150 mM NaCl pH 7.4, RT = 3.4 min |
| Elution: | 30 CV 100 mM citrate pH 6-3 gradient, RT = 6 min |
| CIP: | 3 CV 0.1M NaOH, RT = 6 min |
| Re-equilibration: | 8 CV 20 mM phosphate, 150 mM NaCl pH 7.4, RT = 3.4 min |

The results are shown below in Table 12 and indicate that the antibodies elute at similar pH levels as on the reference, although with some individual variation depending on the particular antibody-resin combination.

TABLE 12

Results from elution pH evaluation

| Sample | Elution pH MabSelect SuRe LX | Elution pH prototype |
|---|---|---|
| mAb 1 | 3.67 | 3.53 |
| mAb 2 | 3.68 | 3.80 |
| Polyclonal IgG | 4.01 (peak 1) | 4.24 (peak 1) |
| | 3.70 (peak 2) | 3.81 (peak 2) |

Figure 7A:
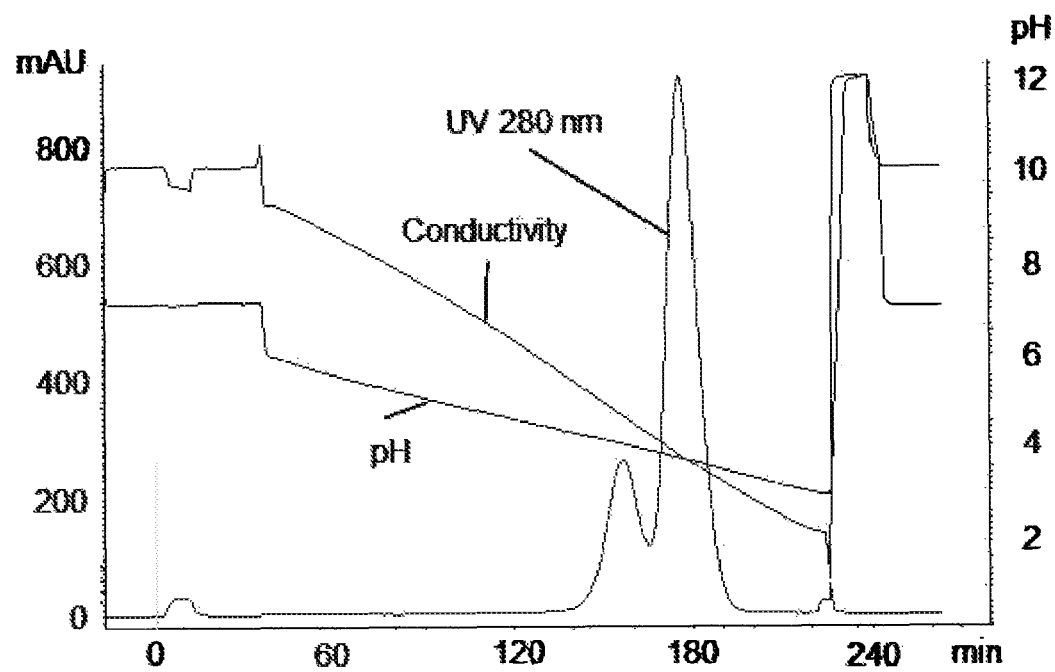
FIGS. 7a-7b respectively show the results from a pH gradient elution of polyclonal human IgG a) from the reference matrix MabSelect SuRe LX (FIG. 7a) and b) a matrix (FIG. 7b) according to the invention.
Figure 7B:
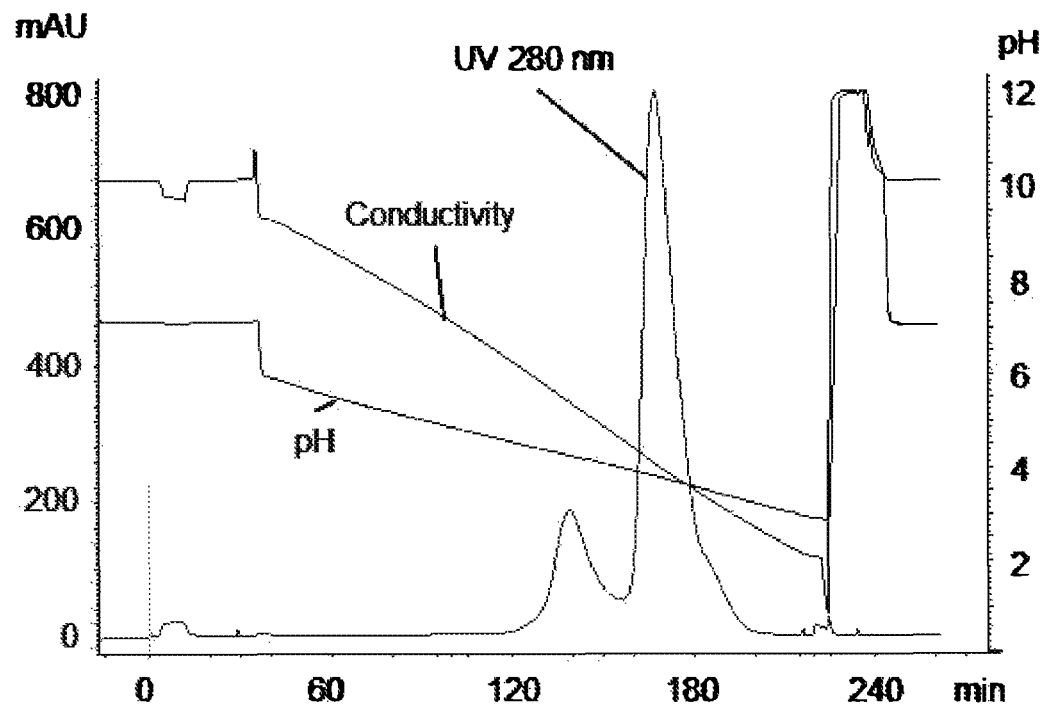

Fractions from the pH-gradient elution of polyclonal IgG were also analysed with respect to content of IgG1, IgG2 and IgG4, using a Biacore SPR instrument (GE Healthcare Life Sciences) with antibodies against the four different IgG classes immobilized on a CM5 Biacore chip as shown in FIGS. 7a and 7b.

Figure 8A:
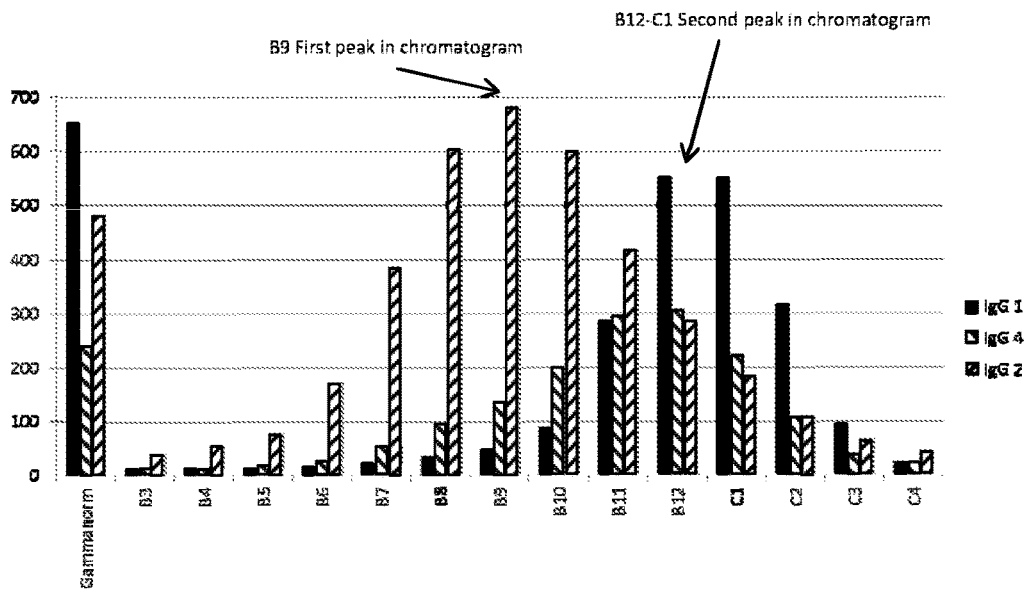
FIGS. 8a-8b respectively show the analyses of the IgG1, IgG2 and IgG4 components in fractions from the chromatograms of (FIG. 7a) reference matrix and (FIG. 7b) matrix according to the invention. For each fraction, the first bar (blue) represents IgG1, the second (red) IgG 4 and the third (green) IgG 2.
Figure 8B:
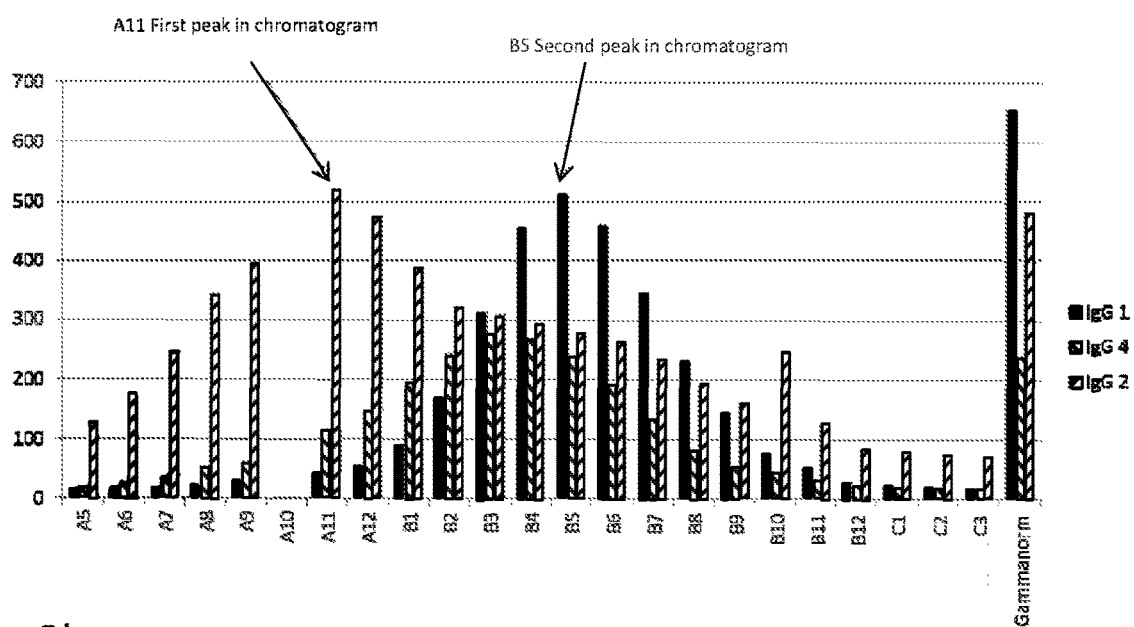

Specifically, the chromatograms for polyclonal IgG on the reference and the prototype are shown in FIGS. 7a and 7b and the IgG class analyses are shown in FIGS. 8a and 8b. The data show that all three classes bind to both resins in a similar way and that the first peak predominantly contains IgG2, while IgG1 and IgG4 elute mainly in the second peak. The anti-IgG3 antibodies cross-reacted with IgG4, so no reliable results for IgG3 were obtained. IgG3 is generally known to show no or only weak binding to Protein A.

Example 10

Figure 9:
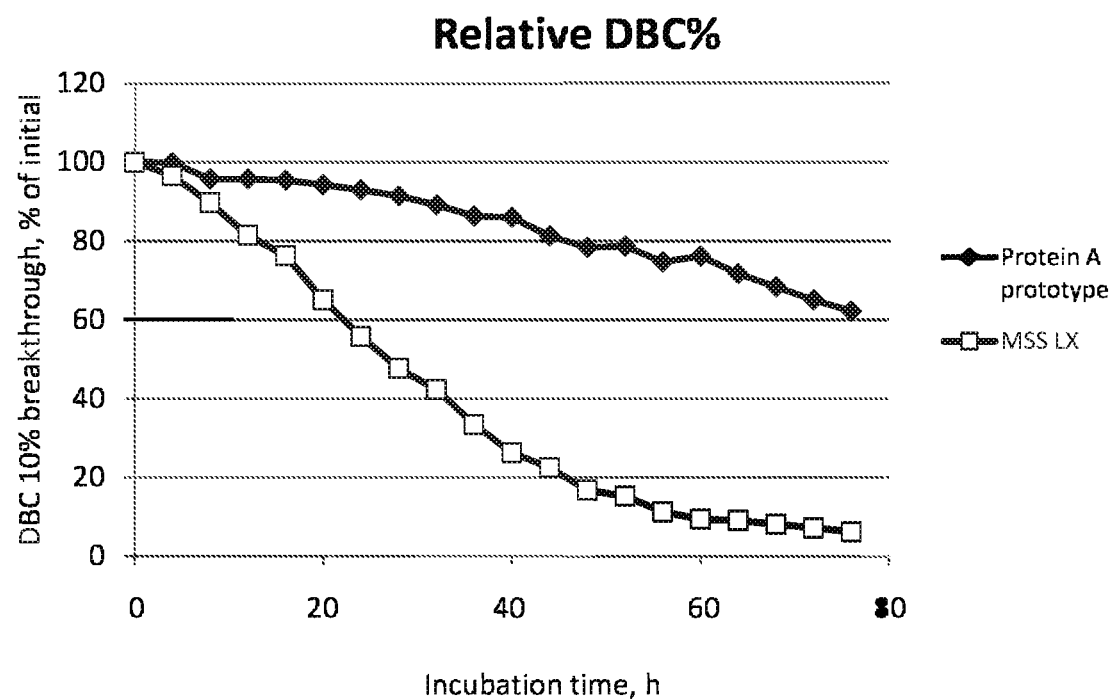
FIG. 9 shows results from accelerated alkali stability measurements with 1 M NaOH incubation for the reference matrix MabSelect SuRe LX (MSS LX) and a matrix according to the invention. The stability is expressed as the percentage of the 10% breakthrough capacity remaining after incubation.

A crosslinked agarose bead matrix prototype, prepared as above, with 12.6 mg/ml ligand (tetramer, SEQ ID NO:20), 84.9 μm median bead diameter (d50,v), Kd 0.71 for dextran Mw 110 kD and 62.2 mg/ml dry weight, was evaluated with respect to alkali stability, using the commercial product MabSelect SuRe LX as a reference. Tricorn 5 columns packed with the resins to 10 cm bed height were flushed with 3 column volumes of 1 M NaOH. The flow was then stopped for 240 minutes (corresponding to 16 normal CIP cycles of 15 min/cycle) before washing out the NaOH solution by 3 column volumes of PBS buffer. The dynamic binding capacity for polyclonal IgG (Gammanorm, Octapharma) was then measured and the process was repeated with another injection of 1 M NaOH. The dynamic capacity was measured after each 240 min incubation cycle with 1 M NaOH. In the capacity measurements, the columns were equilibrated with PBS buffer before the 2 mg/ml sample was loaded (residence time 6 min) until a UV signal of 85% of maximum absorbance was reached. Then the column was washed with PBS buffer, eluted with 500 mM acetic acid pH 3.0 and re-equilibrated. The dynamic binding capacity at 10% and 80% breakthrough was calculated as described above. The results are shown in FIG. 9 and they show that the prototype was significantly more stable than the commercial product.

Example 11

Pressure-Flow Testing of Matrices 300 ml sedimented matrix was packed in a FineLine™ 35 column (GE Healthcare Life Sciences, Uppsala, Sweden), with 35 mm inner diameter and 330 mm tube height. The gel was suspended in distilled water to produce a slurry volume of 620 ml and the height of the packed bed was 300+/−10 mm. The packing pressure was 0.10+/−0.02 bar (10+/−2 kPa).

Distilled water was then pumped through the column at increasing pump rates and the flow rate (expressed as the linear flow velocity, cm/h) and back pressure (MPa) was measured after 5 min for each pump setting. The measurements were continued until a max flow rate and a max pressure was reached, i.e. the flow rate and back pressure achieved when the flow rate starts to diminish at increasing back pressures.

TABLE 9

Pressure flow performance of matrices

| Matrix | Max flow velocity, cm/h | Max pressure (MPa) |
|---|---|---|
| 517 | 1343 | 0.56 |
| 106 | 1306 | 0.56 |
| 531C | 513 | 0.51 |
| P10 | 862 | 0.60 |
| S9 | 1172 | 0.64 |

The P10 and S9 matrices have a higher rigidity, as indicated by the max pressure, and can thus sustain comparatively high flow velocities despite their low (59-64 micrometers) median particle diameters.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

Itemized List of Embodiments i. An Fc-binding polypeptide which comprises a sequence as defined by, or having at least 90% or at least 95% or 98% identity to SEQ ID NO: 53.

```
                                          (SEQ ID NO: 53)
X1Q X2AFYEILX3LP NLTEEQRX4X5F IX6X7LKDX8PSX9

SX10X11X12LAEAKX13 X14NX15AQ
``` wherein individually of each other:
X$_1$=A or Q or is deleted
X$_2$=E, K, Y, T, F, L, W, I, M, V, A, H or R
X$_3$=H or K
X$_4$=A or N
X$_5$=A, G, S, Y, Q, T, N, F, L, W, I, M, V, D, E, H, R or K
X$_6$=Q or E
X$_7$=S or K
X$_8$=E or D
X$_9$=Q or V or is deleted
X$_{10}$=K, R or A or is deleted
X$_{11}$=A, E or N or is deleted
X$_{12}$=I or L
X$_{13}$=K or R
X$_{14}$=L or Y
X$_{15}$=D, F, Y, W, K or R ii. The polypeptide of embodiment i, wherein: X$_1$=A or is deleted, X$_2$=E, X$_3$=H, X$_4$=N, X$_6$=Q, X$_7$=S, X$_8$=D, X$_9$=V or is deleted, X$_{10}$=K or is deleted, X$_{11}$=A or is deleted, X$_{12}$=I, X$_{13}$=K, X$_{14}$=L.

iii. The polypeptide of embodiment i or ii, wherein X$_1$=A, X$_2$=E, X$_3$=H, X$_4$=N, X$_5$=A, X$_6$=Q, X$_7$=S, X$_8$=D, X$_9$=V, X$_{10}$=K, X$_{11}$=A, X$_{12}$=I, X$_{13}$=K, X$_{14}$=L and X$_{15}$=D.

iv. The polypeptide of embodiment i or ii, wherein X$_1$ is deleted, X$_2$=E, X$_3$=H, X$_4$=N, X$_5$=A, X$_6$=Q, X$_7$=S, X$_8$=D, X$_9$=V, X$_{10}$=K, X$_{11}$=A, X$_{12}$=I, X$_{13}$=K, X$_{14}$=L and X$_{15}$=D.

v. The polypeptide of embodiment i or ii, wherein X$_1$=A, X$_2$=E, X$_3$=H, X$_4$=N, X$_5$=S, Y, Q, T, N, F, L, W, I, M, V, D, E, H, R or K, X$_6$=Q, X$_7$=S, X$_8$=D, X$_9$=V, X$_{10}$=K, X$_{11}$=A, X$_{12}$=I, X$_{13}$=K, X$_{14}$=L and X$_{15}$=D.

vi. The polypeptide of embodiment i or ii, wherein X$_1$=A, X$_2$=E, X$_3$=H, X$_4$=N, X$_5$=A, X$_6$=Q, X$_7$=S, X$_8$=D, X$_9$ is deleted, X$_{10}$=K, X$_{11}$=A, X$_{12}$=I, X$_{13}$=K, X$_{14}$=L and X$_{15}$=D.

vii. The polypeptide of embodiment i or ii, wherein X$_1$=A, X$_2$=E, X$_3$=H, X$_4$=N, X$_5$=A, X$_6$=Q, X$_7$=S, X$_8$=D, X$_9$=V, X$_{10}$ is deleted, X$_{11}$=A, X$_{12}$=I, X$_{13}$=K, X$_{14}$=L and X$_{15}$=D.

viii. The polypeptide of embodiment i or ii, wherein X$_1$=A, X$_2$=E, X$_3$=H, X$_4$=N, X$_5$=A, X$_6$=Q, X$_7$=S, X$_8$=D, X$_9$=V, X$_{10}$=K, X$_{11}$ is deleted, X$_{12}$=I, X$_{13}$=K, X$_{14}$=L and X$_{15}$=D.

ix. The polypeptide of embodiment i or ii, wherein X$_1$=A, X$_2$=E, X$_3$=H, X$_4$=N, X$_5$=A, X$_6$=Q, X$_7$=S, X$_8$=D, X$_9$=V, X$_{10}$=K, X$_{11}$=A, X$_{12}$=I, X$_{13}$=K, X$_{14}$=L and X$_{15}$=F, Y, W, K or R.

x. An Fc-binding polypeptide comprising a mutant of a parental Fc-binding domain of *Staphylococcus* Protein A (SpA), as defined by, or having at least 90% such as at least 95% or 98% identity to, SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO: 51 or SEQ ID NO: 52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine.

xi. The polypeptide of embodiment x, comprising a mutant of a parental Fc-binding domain of *Staphylococcus* Protein A (SpA), as defined by, or having at least 90% such as at least 95% or 98% identity to, SEQ ID NO: 51 or SEQ ID NO: 52.

xii. The polypeptide of embodiment x or xi, wherein the amino acid residue at the position corresponding to position 11 in SEQ ID NO:4-7 is a glutamic acid.

xiii. The polypeptide of any one of embodiments x-xii, wherein the amino acid residue at the position corresponding to position 11 in SEQ ID NO:4-7 is a lysine.

xiv. The polypeptide of any one of embodiments x-xiii, wherein the amino acid residue at the position corresponding to position 29 in SEQ ID NO:4-7 is a glycine, serine, tyrosine, glutamine, threonine, asparagine, phenylalanine, leucine, tryptophan, isoleucine, methionine, valine, aspartic acid, glutamic acid, histidine, arginine or lysine.

xv. The polypeptide of any one of embodiments x-xiv, wherein the amino acid residue at the position corresponding to position 9 in SEQ ID NO:4-7 is an alanine.

xvi. The polypeptide of any one of embodiments x-xv, wherein the amino acid residue at the position corresponding to position 9 in SEQ ID NO:4-7 has been deleted.

xvii. The polypeptide of any one of embodiments x-xvi, wherein the amino acid residue at the position corresponding to position 50 in SEQ ID NO:4-7 is an arginine or a glutamic acid, such as an arginine.

xviii. The polypeptide of any one of embodiments x-xvii, wherein the amino acid residue at the position corresponding to position 43 in SEQ ID NO:4-7 has been deleted.

xix. The polypeptide of any one of embodiments x-xviii, wherein the amino acid residue at the position corresponding to position 28 in SEQ ID NO:4-7 is an alanine or an asparagine.

xx. The polypeptide of any one of embodiments x-xix, wherein the amino acid residue at the position corresponding to position 40 in SEQ ID NO:4-7 is selected from the group consisting of asparagine, alanine, glutamic acid and valine.

xxi. The polypeptide of any one of embodiments x-xx, wherein the amino acid residue at the position corresponding to position 40 in SEQ ID NO:4-7 has been deleted.

xxii. The polypeptide according to any one of embodiments x-xxi, wherein the amino acid residue at the position corresponding to position 42 in SEQ ID NO:4-7 is an alanine, lysine or arginine, such as an arginine.

xxiii. The polypeptide according to any one of embodiments x-xxii, wherein the amino acid residue at the position corresponding to position 42 in SEQ ID NO:4-7 has been deleted.

xxiv. The polypeptide according to any one of embodiments x-xxiii, wherein the amino acid residue at the position corresponding to position 44 in SEQ ID NO:4-7 is a leucine or an isoleucine, such as an isoleucine.

xxv. The polypeptide according to any one of embodiments x-xxiv, wherein the amino acid residue at the position corresponding to position 44 in SEQ ID NO:4-7 has been deleted.

xxvi. The polypeptide according to any one of embodiments x-xxv, wherein the amino acid residue at the position corresponding to position 53 in SEQ ID NO:4-7 is a phenylalanine, a tyrosine, a tryptophan, an arginine or a lysine.

xxvii. The polypeptide according to any one of embodiments x-xxvi, wherein the amino acid residue at the position corresponding to position 18 in SEQ ID NO:4-7 is a lysine or a histidine, such as a lysine.

xxviii. The polypeptide according to any one of embodiments x-xxvii, wherein the amino acid residue at the position corresponding to position 33 in SEQ ID NO:4-7 is a lysine or a serine, such as a lysine.

xxix. The polypeptide according to any one of embodiments x-xxviii, wherein the amino acid residue at the position corresponding to position 37 in SEQ ID NO:4-7 is a glutamic acid or an aspartic acid, such as a glutamic acid.

xxx. The polypeptide according to any one of embodiments x-xxix, wherein the amino acid residue at the position corresponding to position 51 in SEQ ID NO:4-7 is a tyrosine or a leucine, such as a tyrosine.

xxxi. The polypeptide according to any one of embodiments x-xxx, wherein one or more of the amino acid residues at the positions corresponding to positions 1, 2, 3, 4, 5, 6, 7, 8, 56, 57 or 58 in SEQ ID NO: 4-7 have been deleted.

xxxii. The polypeptide according to any one of embodiments x-xxxi, wherein the mutation is selected from the group consisting of:
Q9A,N11E, A29G,Q40V,A42K,N43A,L44I;
Q9A,N11E, A29S,Q40V,A42K,N43A,L44I;
Q9A,N11E, A29Y,Q40V,A42K,N43A,L44I;
Q9A,N11E, A29Q,Q40V,A42K,N43A,L44I;
Q9A,N11E, A29T,Q40V,A42K,N43A,L44I;
Q9A,N11E, A29N,Q40V,A42K,N43A,L44I;
Q9A,N11E, A29F,Q40V,A42K,N43A,L44I;
Q9A,N11E, A29L,Q40V,A42K,N43A,L44I;
Q9A,N11E, A29W,Q40V,A42K,N43A,L44I;
Q9A,N11E, A29I,Q40V,A42K,N43A,L44I;
Q9A,N11E, A29M,Q40V,A42K,N43A,L44I;
Q9A,N11E, A29V,Q40V,A42K,N43A,L44I;
Q9A,N11E, A29D,Q40V,A42K,N43A,L44I;
Q9A,N11E, A29E,Q40V,A42K,N43A,L44I;
Q9A,N11E, A29H,Q40V,A42K,N43A,L44I;
Q9A,N11E, A29R,Q40V,A42K,N43A,L44I; and
Q9A,N11E, A29K,Q40V,A42K,N43A,L44I.

xxxiii. The polypeptide according to any one of embodiments x-xxxii, wherein the mutation is selected from the group consisting of:
Q9A,N11E, Q40V,A42K,N43A,L44I,D53F;
Q9A,N11E, Q40V,A42K,N43A,L44I,D53Y;
Q9A,N11E, Q40V,A42K,N43A,L44I,D53W;
Q9A,N11E, Q40V,A42K,N43A,L44I,D53K; and
Q9A,N11E, Q40V,A42K,N43A,L44I,D53R.

xxxiv. The polypeptide according to any one of embodiments x-xxxiii, wherein the mutation is selected from the group consisting of:
Q9del,N11E, Q40V,A42K,N43A,L44I;
Q9A,N11E, Q40del,A42K,N43A,L44I;
Q9A,N11E, Q40V,A42del,N43A,L44I; and
Q9A,N11E, Q40V,A42K,N43del,L44I.

xxxv. The polypeptide according to any one of embodiments x-xxxiv, wherein the mutation is selected from the group consisting of:
D2del,A3del,K4del,Q9A,N11E,Q40V,A42K,N43A,L44I;
V1del,D2del,Q9A,N11E,Q40V,A42K,N43A,L44I,K58del;
V1del,D2del,A3del,Q9A,N11E,Q40V,A42K,N43A,L44I, P57del,K58del;
K4del,F5del,D6del,K7del,E8del,Q9A,N11E,Q40V,A42K, N43A,L44I;
Q9A,N11E,Q40V,A42K,N43A,L44I,A56del,P57del, K58del;
V1del,D2del,A3del,Q9A,N11E,Q40V,A42K,N43A,L44I;
V1del,D2del,A3del,K4del,F5del,D6del,K7del,E8del,Q9A, N11E,Q40V,A42K,N43A,L44I; and
Q9A,N11E,Q40V,A42K,N43A,L44I,K58_insYEDG.

xxxvi. The polypeptide according to any one of embodiments i-xxxi, comprising or consisting essentially of a sequence having at least 90% identity to an amino acid sequence selected from the group consisting of: SEQ ID NO: 54, SEQ ID NO: 55, SEQ ID NO: 56, SEQ ID NO: 57, SEQ ID NO: 58, SEQ ID NO: 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67, SEQ ID NO 68, SEQ ID NO 69 and SEQ ID NO 70.

xxxvii. The polypeptide according to any one of embodiments i-xxxi, comprising or consisting essentially of a sequence having at least 90% identity to an amino acid sequence selected from the group consisting of: SEQ ID NO 71, SEQ ID NO 72, SEQ ID NO 73, SEQ ID NO 74 and SEQ ID NO 75.

xxxviii. The polypeptide according to any one of embodiments i-xxxi, comprising or consisting essentially of a sequence having at least 90% identity to an amino acid sequence selected from the group consisting of: SEQ ID NO 76, SEQ ID NO 77, SEQ ID NO 78 and SEQ ID NO 79.

xxxix. The polypeptide according to any one of embodiments i-xxxi, comprising or consisting essentially of a sequence having at least 90% identity to an amino acid sequence selected from the group consisting of: SEQ ID NO 89, SEQ ID NO 90, SEQ ID NO 91, SEQ ID NO 92, SEQ ID NO 93, SEQ ID NO 94 and SEQ ID NO 95.

xl. The polypeptide according to any preceding embodiment, which polypeptide has an improved alkaline stability compared to a polypeptide as defined by SEQ ID NO 1, SEQ ID NO 2, SEQ ID NO 3, SEQ ID NO 4, SEQ ID NO: 5, SEQ ID NO 6 or SEQ ID NO 7, such as by SEQ ID NO 7.

xli. The polypeptide according to any preceding embodiment, which polypeptide has an improved alkaline stability compared to a parental polypeptide as defined by SEQ ID NO 1, SEQ ID NO 2, SEQ ID NO 3, SEQ ID NO 4, SEQ ID NO: 5, SEQ ID NO 6 or SEQ ID NO 7, such as by SEQ ID NO 7.

xlii. The polypeptide according to embodiment xl or xli, wherein the alkaline stability is improved as measured by the remaining IgG-binding capacity, after 24, 25 h incubation in 0.5 M or 1.0 M aqueous NaOH at 22+/−2° C.

xliii. A multimer comprising or consisting essentially of a plurality of polypeptides as defined by any preceding embodiment.

xliv. The multimer according to embodiment xliii, wherein the polypeptides are linked by linkers comprising up to 25 amino acids, such as 3-25 or 3-20 amino acids.

xlv. The multimer of embodiment xliii or xliv, wherein at least two polypeptides are linked by linkers comprising or consisting essentially of a sequence having at least 90% identity with an amino acid sequence selected from the group consisting of APKVDAKFDKE (SEQ ID NO: 96), APKVDNKFNKE (SEQ ID NO: 97), APKADNKFNKE (SEQ ID NO: 98), APKVFDKE (SEQ ID NO: 99), APAKFDKE (SEQ ID NO: 100), AKFDKE (SEQ ID NO: 101), APKVDA (SEQ ID NO: 102), VDAKFDKE (SEQ ID NO: 103), APKKFDKE (SEQ ID NO: 104), APK, APKYEDGVDAKFDKE (SEQ ID NO: 105) and YEDG (SEQ ID NO: 106).

xlvi. The multimer according to embodiment xliv or xlv, which is a dimer, trimer, tetramer, pentamer, hexamer, heptamer, octamer or nonamer.

xlvii. The multimer according to any one of embodiments xliv-xlvi, which comprises or consists essentially of a sequence defined by SEQ ID NO 80, SEQ ID NO 81, SEQ ID NO 82, SEQ ID NO 83, SEQ ID NO 84, SEQ ID NO 85, SEQ ID NO 86 and SEQ ID NO 87.

xlviii. The polypeptide or multimer according to any preceding embodiment, further comprising at, or within 1-5 amino acid residues from, the C-terminal or N-terminal one or more coupling element, selected from the group consisting of one or more cysteine residues, a plurality of lysine residues and a plurality of histidine residues.

xlix. A nucleic acid or a vector encoding a polypeptide or multimer according to any preceding embodiment.

l. An expression system, which comprises a nucleic acid or vector according to embodiment xlix.

li. A separation matrix, wherein a plurality of polypeptides or multimers according to any one of embodiment i-xlviii have been coupled to a solid support.

lii. A separation matrix comprising at least 11 mg/ml Fc-binding ligands covalently coupled to a porous support, wherein:
a) said ligands comprise multimers of alkali-stabilized Protein A domains,
b) said porous support comprises cross-linked polymer particles having a volume-weighted median diameter (d50, v) of 55-70 micrometers and a dry solids weight of 55-80 mg/ml.

liii. A separation matrix comprising at least 15, such as 15-21 or 15-18 mg/ml Fc-binding ligands covalently coupled to a porous support, wherein said ligands comprise multimers of alkali-stabilized Protein A domains.

liv. The separation matrix of embodiment li or liii, wherein said cross-linked polymer particles comprise cross-linked polysaccharide particles.

lv. The separation matrix of any one of embodiments li-liv, wherein said cross-linked polymer particles comprise cross-linked agarose particles.

lvi. The separation matrix of any one of embodiments li-lv, wherein said cross-linked polymer particles have a pore size corresponding to an inverse gel filtration chromatography Kd value of 0.70-0.85 for dextran of Mw 110 kDa.

lvii. The separation matrix of any one of embodiments li-lvi, which has a max pressure of at least 0.58, such as at least 0.60, MPa when packed at 300+/−10 mm bed height in a FineLine™ 35 column.

lviii. The separation matrix of any one of embodiments li-lvii, wherein said multimers comprise tetramers, pentamers, hexamers or heptamers of alkali-stabilized Protein A domains.

lix. The separation matrix of any one of embodiments li-lviii, wherein said multimers comprise hexamers of alkali-stabilized Protein A domains.

lx. The separation matrix of any one of embodiments li-lix, wherein the polypeptides are linked by linkers comprising up to 25 amino acids, such as 3-25 or 3-20 amino acids.

lxi. The separation matrix of any one of embodiments li-lx, wherein at least two polypeptides are linked by linkers comprising or consisting essentially of a sequence having at least 90% identity with an amino acid sequence selected from the group consisting of APKVDAKFDKE (SEQ ID NO: 96), APKVDNKFNKE (SEQ ID NO: 97), APKADNKFNKE (SEQ ID NO: 98), APKVFDKE (SEQ ID NO: 99), APAKFDKE (SEQ ID NO: 100), AKFDKE (SEQ ID NO: 101), APKVDA (SEQ ID NO: 102), VDAKFDKE (SEQ ID NO:103), APKKFDKE (SEQ ID NO: 104), APK, APKYEDGVDAKFDKE (SEQ ID NO: 105) and YEDG (SEQ ID NO: 106).

lxii. The separation matrix of any one of embodiments li-lxi, having a 10% breakthrough dynamic binding capacity for IgG of at least 45 mg/ml, such as at least 50 or at least 55 mg/ml mg/ml at 2.4 min residence time.

lxiii. The separation matrix of any one of embodiments li-lxii, having a 10% breakthrough dynamic binding capacity for IgG of at least 60 mg/ml, such as at least 65, at least 70 or at least 75 mg/ml at 6 min residence time.

lxiv. The separation matrix of any one of embodiments li-lxiii, having a 10% breakthrough dynamic binding capacity for IgG of at least 60 mg/ml, such as at least 65, at least 70 or at least 75 mg/ml at 6 min residence time.

lxv. The separation matrix of any one of embodiments li-lxiv, wherein the 10% breakthrough dynamic binding capacity for IgG at 2.4 or 6 min residence time is reduced by less than 20% after incubation 31 h in 1.0 M aqueous NaOH at 22+/−2 C.

lxvi. The separation matrix of any one of embodiments li-lxv, having a dissociation constant for IgG2 of below 0.2 mg/ml, such as below 0.1 mg/ml, in 20 mM phosphate buffer, 180 mM NaCl, pH 7.5.

lxvii. The separation matrix of any any one of embodiments li-lxvi, which has a max pressure of at least 0.58, such as at least 0.60, MPa when packed at 300+/−10 mm bed height in a FineLine™ 35 column.

lxviii. The separation matrix according to any one of embodiments li-lxvii, wherein the polypeptides or multimers have been coupled to the solid support or porous support via thioether bonds.

lxix. The separation matrix according to any one of embodiments li-lxviii, wherein the solid support or porous support is a polysaccharide.

lxx. The separation matrix according to any one of embodiments li-lxix, wherein the IgG capacity of the matrix after 24 incubation in 0.5 M NaOH at 22+/−2° C. is at least 80, such as at least 85, at least 90 or at least 95% of the IgG capacity before the incubation.

lxxi. The separation matrix according to any one of embodiments li-lxx, wherein the IgG capacity of the matrix after 24 incubation in 1.0 M NaOH at 22+/−2° C. is at least 70, such as at least 80 or at least 90% of the IgG capacity before the incubation.

lxxii. The separation matrix of any one of embodiments li-lxxi, wherein said alkali-stabilized Protein A domains or plurality of polypeptides/multimers comprise(s) mutants of a parental Fc-binding domain of *Staphylococcus* Protein A (SpA), as defined by SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:22, SEQ ID NO: 51 or SEQ ID NO: 52, wherein at least the asparagine or serine residue at the position corresponding to position 11 in SEQ ID NO:4-7 has been mutated to an amino acid selected from the group consisting of glutamic acid, lysine, tyrosine, threonine, phenylalanine, leucine, isoleucine, tryptophan, methionine, valine, alanine, histidine and arginine.

lxxiii. The separation matrix of embodiment lxxii, wherein the amino acid residue at the position corresponding to position 11 in SEQ ID NO:4-7 is, or has been mutated to, a glutamic acid or a lysine, such as to a glutamic acid.

lxxiv. The separation matrix of embodiment lxxii or lxxiii, wherein the amino acid residue at the position corresponding to position 40 in SEQ ID NO:4-7 is, or has been mutated to, a valine.

lxxv. The separation matrix of any one of embodiments lxxii-lxxiv, wherein the amino acid residue at the position corresponding to position 9 in SEQ ID NO:4-7 is an alanine lxxvi. The separation matrix of any one of embodiments lxxii-lxxiv, wherein the amino acid residue at the position corresponding to position 9 in SEQ ID NO:4-7 has been deleted.

lxxvii. The separation matrix of any one of embodiments lxxii-lxxvi, wherein one or more of the amino acid residues at the positions corresponding to positions 1, 2, 3, 4, 5, 6, 7, 8, 56, 57 or 58 in SEQ ID NO: 4-7 have been deleted.

lxxviii. The separation matrix of any one of embodiments li-lxxi, wherein said alkali-stabilized Protein A domains or plurality of polypeptides/multimers comprise(s) an Fc-binding polypeptide having an amino acid sequence as defined by, or having at least 80%, such as at least 90, 95 or 98%, identity to SEQ ID NO: 53.

(SEQ ID NO: 53)
$X_1Q$ $X_2AFYEILX_3LP$ $NLTEEQRX_4X_5F$ $IX_6X_7LKDX_8PSX_9$ $SX_{10}X_{11}X_{12}LAEAKX_{13}$ $X_{14}NX_{15}AQ$ wherein individually of each other:
$X_1$=A or Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K
$X_6$=Q or E
$X_7$=S or K
$X_8$=E or D
$X_9$=Q or V or is deleted
$X_{10}$=K, R or A or is deleted
$X_{11}$=A, E or N or is deleted
$X_{12}$=I or L
$X_{13}$=K or R
$X_{14}$=L or Y
$X_{15}$=D, F, Y, W, K or R lxxix. The separation matrix of embodiment lxxviii, wherein individually of each other:
$X_1$=A or is deleted, $X_2$=E, $X_3$=H, $X_4$=N, $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L.

lxxx. The separation matrix of embodiment lxxviii, wherein individually of each other:
$X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

lxxxi. The separation matrix of embodiment lxxviii, wherein individually of each other:
wherein $X_1$ is A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

lxxxii. The separation matrix of embodiment lxxviii, wherein individually of each other:
wherein $X_1$ is A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

lxxxiii. The separation matrix according to any one of embodiments li-lxxi, wherein said alkali-stabilized Protein A domains or plurality of polypeptides/multimers comprise mutants of a parental Fc-binding domain of *Staphylococcus* Protein A (SpA), as defined by SEQ ID NO: 51 or SEQ ID NO: 52, wherein the amino acid residues at positions 13 and 44 of SEQ ID NO: 51 or 52 are asparagines and wherein at least the asparagine residue at position 3 of SEQ ID NO: 51 or 52 has been mutated to an amino acid selected from the group consisting of glutamic acid, lysine, tyrosine, threonine, phenylalanine, leucine, isoleucine, tryptophan, methionine, valine, alanine, histidine and arginine.

lxxxiv. The separation matrix according to embodiment lxxxiii, wherein the glutamine residue at position 1 of SEQ ID NO: 51 or 52 has been mutated to an alanine.

lxxxv. The separation matrix according to embodiment lxxxiii or lxxxiv, wherein the asparagine or glutamic acid residue at position 35 of SEQ ID NO: 51 or 52 has been mutated to an alanine.

lxxxvi. The separation matrix according to any one of embodiments lxxxiii-lxxxv, wherein said separation matrix comprises at least 11 mg/ml, such as at least 15 mg/ml, of said multimers of immunoglobulin-binding alkali-stabilized Protein A domains covalently coupled to a porous support.

lxxxvii. The separation matrix according to any one of embodiments li-lxxxvi, wherein said multimers or polypeptides further comprise at, or within 1-5 amino acid residues from, the C-terminal or N-terminal one or more coupling element, selected from the group consisting of one or more cysteine residues, a plurality of lysine residues and a plurality of histidine residues.

lxxxviii. The separation matrix according to any one of embodiments li-lxxxvii wherein said multimers or polypeptides further comprise at the N-terminal a leader sequence, comprising 1-20 amino acid residues.

lxxxix. A method of isolating an immunoglobulin, wherein a separation matrix according to any one of embodiments li-lxxxviii is used.

xc. The method of embodiment lxxxix, comprising the steps of:
a) contacting a liquid sample comprising an immunoglobulin with a separation matrix according to any one of embodiments li-lxxxii,
b) washing said separation matrix with a washing liquid,
c) eluting the immunoglobulin from the separation matrix with an elution liquid, and d) cleaning the separation matrix with a cleaning liquid.

xci. The method of embodiment xc, wherein the cleaning liquid is alkaline, such as with a pH of 13-14.

xcii. The method of embodiment xc or xci, wherein the cleaning liquid comprises 0.1-1.0 M NaOH or KOH, such as 0.5-1.0 M or 0.4-1.0 M NaOH or KOH.

xciii. The method of any one of embodiments xc-xcii, wherein steps a)-d) are repeated at least 10 times, such as at least 50 times or 50-200 times.

xciv. The method of any one of embodiments xc-xciii, wherein steps a)-c) are repeated at least 10 times, such as at least 50 times or 50-200 times and wherein step d) is performed after a plurality of instances of step c), such as at least 10 or at least 50 times.

xcv. The method of any one of embodiments xc-xciv, wherein in step b) at least 40 mg immunoglobulin per ml separation matrix is contacted with said separation matrix.

xcvi. The method of any one of embodiments xc-xcv, wherein said liquid sample is a clarified cell broth and wherein in step d) said immunoglobulin is recovered as an eluate comprising less than 2000 ppm host cell proteins.

xcvii. The method of any one of embodiments xc-xcvi, wherein the ratio of the host cell protein concentration in said liquid sample to the host cell concentration in an immunoglobulin-containing eluate recovered in step d) is at least 100, such as at least 300.

xcviii. The method of any one of embodiments xc-xcvii, wherein in step d) said elution liquid has a pH of 2.5-5.0, such as 3.2-4.5.

xcix. The method of any one of embodiments xc-xcviii, wherein said immunoglobulin comprises IgG1, IgG2 and/or IgG4.

c. The method of any one of embodiments xc-xcix, wherein said washing liquid has a pH of 5-8 and optionally comprises one or more of a detergent, a water-miscible organic solvent, a chaotrope, arginine or an arginine derivative, calcium ions and tetraalkylammonium ions.

ci. The method of any one of embodiments xc-c, wherein in step b) the pH is 6-8.

cii. The method of any one of embodiments xc-ci, wherein in step b) the residence time of said liquid sample on said separation matrix is 2-20 min, such as 2-10 min.

ciii. A method of isolating an immunoglobulin, comprising the steps of:
a) providing a separation matrix comprising at least 15 mg/ml multimers of immunoglobulin-binding alkali-stabilized Protein A domains covalently coupled to a porous support, b) contacting a liquid sample comprising an immunoglobulin with said separation matrix, c) washing said separation matrix with a washing liquid,
d) eluting the immunoglobulin from the separation matrix with an elution liquid, and e) cleaning the separation matrix with a cleaning liquid comprising at least 0.5 M NaOH, such as at least 1 M NaOH, wherein in step b) at least 40 mg immunoglobulin per ml separation matrix is contacted with said separation matrix.

civ. The method of embodiment ciii, wherein said multimers conform to any one of embodiments xliii-xlix.

cv. The method of embodiment ciii or civ, wherein said liquid sample is a clarified cell broth and wherein in step d) said immunoglobulin is recovered as an eluate comprising less than 2000 ppm host cell proteins.

cvi. The method of any one of embodiments ciii-cv, wherein the ratio of the host cell protein concentration in said liquid sample to the host cell concentration in an immunoglobulin-containing eluate recovered in step d) is at least 100, such as at least 300.

cvii. The method of any one of embodiments ciii-cvi, wherein steps b)-e) are repeated at least 10 times, such as at least 50 times or 50-200 times.

```

The invention claimed is:

1. A method of isolating an immunoglobulin, comprising the steps of:
   a) providing a separation matrix comprising at least 15 mg/ml multimers of immunoglobulin-binding alkali-stabilized Protein A domains covalently coupled to a porous support,
   b) contacting a liquid sample comprising an immunoglobulin with said separation matrix, wherein at least 40 mg immunoglobulin per ml separation matrix is contacted with said separation matrix,
   c) washing said separation matrix with a washing liquid,
   d) eluting the immunoglobulin from the separation matrix with an elution liquid, and
   e) cleaning the separation matrix with a cleaning liquid comprising at least 0.5 M NaOH, wherein said alkali-stabilized Protein A domains comprise an Fc-binding polypeptide having an amino acid sequence as defined by, or having at least 80% identity to the sequence defined by $X_1QX_2AFYEILX_3LPNLTEEQRX_4X_5FIX_6X_7LKDX_8PSX_9SX_{10}X_{11}X_{12}LAEAKX_{13}X_{14}NX_{15}AQ$ (SEQ ID NO: 53)
wherein individually of each other:
$X_1$=A or Q or is deleted
$X_2$=E, K, Y, T, F, L, W, I, M, V, A, H or R
$X_3$=H or K
$X_4$=A or N
$X_5$=A, G, S, Y, Q, T, N, F, L, W, I, M, V, D, E, H, R or K
$X_6$=Q or E
$X_7$=S or K
$X_8$=E or D
$X_9$=Q or V or is deleted
$X_{10}$=K, R or A or is deleted
$X_{11}$=A, E or N or is deleted
$X_{12}$=I or L
$X_{13}$=K or R
$X_{14}$=L or Y
$X_{15}$=D, F, Y, W, K or R.

2. The method of claim 1, wherein said liquid sample is a clarified cell broth and wherein in step d) said immunoglobulin is recovered as an eluate comprising less than 2000 ppm host cell proteins.

3. The method of claim 1, wherein steps b)-e) are repeated at least 10 times.

4. The method of claim 1, wherein said multimers comprise tetramers, pentamers, hexamers or heptamers of alkali-stabilized Protein A domains.

5. The method of claim 1, wherein in step d) said elution liquid has a pH of 2.5-4.5.

6. The method of claim 1, wherein said multimers are coupled to said support via thioether links.

7. The method of claim 1, wherein in step b) the pH is 6-8.

8. The method of claim 1, wherein in step b) the residence time of said liquid sample on said separation matrix is 2-20 min.

9. The method of claim 1, wherein said porous support comprises cross-linked polymer particles having a volume-weighted median diameter (d50,v) of 56-70 micrometers and a dry solids weight of 55-80 mg/ml.

10. The method of claim 9, wherein said cross-linked polymer particles have a pore size corresponding to an inverse gel filtration chromatography Kd value of 0.69-0.85 for dextran of Mw 110 kDa.

11. The method of claim 9, wherein said separation matrix has a max pressure of at least 0.58 MPa when packed at 300+/-10 mm bed height in a column.

12. The method of claim 1, wherein individually of each other:
$X_1$=A or is deleted, $X_2$=E, $X_3$=H, $X_4$=N, $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L.

13. The method of claim 1, wherein individually of each other:
$X_1$=A, $X_2$=E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

14. The method of claim 1, wherein individually of each other:
$X_1$ is A, $X_2$=E, $X_3$=H, $X_4$=N, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

15. The method of claim 1, wherein individually of each other:

$X_1$ is A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

16. The method of claim 1, wherein said alkali-stabilized Protein A domains comprise an Fc-binding polypeptide having an amino acid sequence having at least 90% identity to SEQ ID NO: 53.

17. The method of claim 1, wherein said alkali-stabilized Protein A domains comprise an Fc-binding polypeptide having an amino acid sequence having at least 95% identity to SEQ ID NO: 53.

18. The method of claim 1, wherein said alkali-stabilized Protein A domains comprise an Fc-binding polypeptide having an amino acid sequence having at least 98% identity to SEQ ID NO: 53.

19. The method of claim 1, wherein said alkali-stabilized Protein A domains comprise an Fc-binding polypeptide having an amino acid sequence identical to SEQ ID NO: 53.

20. The method of claim 1, wherein said alkali-stabilized Protein A domains comprise an Fc-binding polypeptide having an amino acid sequence identical to SEQ ID NO: 11.

\* \* \* \* \*

EX PARTE REEXAMINATION CERTIFICATE (12570th)
United States Patent
Forss et al.

(10) Number: US 11,623,941 C1
(45) Certificate Issued: Apr. 5, 2024

(54) SEPARATION METHOD

(71) Applicant: Cytiva BioProcess R&D AB, Uppsala (SE)

(72) Inventors: Annika Kristina Forss, Uppsala (SE); Gustav Jose Rodrigo, Uppsala (SE); Tomas Bjorkman, Uppsala (SE); Jesper Ulf Hansson, Uppsala (SE); Mats Ander, Uppsala (SE)

(73) Assignee: CYTIVA BIOPROCESS R&D AB, Uppsala (SE)

Reexamination Request:
No. 90/015,234, May 16, 2023

Reexamination Certificate for:
Patent No.: 11,623,941
Issued: Apr. 11, 2023
Appl. No.: 16/884,475
Filed: May 27, 2020

Related U.S. Application Data

(63) Continuation of application No. 15/348,699, filed on Nov. 10, 2016, now Pat. No. 10,703,774, which is a continuation-in-part of application No. 15/282,367, filed on Sep. 30, 2016, now Pat. No. 10,654,887.

(51) Int. Cl.
| | |
|---|---|
| *C07K 1/22* | (2006.01) |
| *B01D 15/00* | (2006.01) |
| *B01J 20/286* | (2006.01) |
| *B01J 20/32* | (2006.01) |
| *C07K 14/31* | (2006.01) |
| *C07K 16/06* | (2006.01) |
| *C07K 16/12* | (2006.01) |
| *C07K 17/10* | (2006.01) |

(52) U.S. Cl.
CPC ............ *C07K 1/22* (2013.01); *B01D 15/00* (2013.01); *B01J 20/286* (2013.01); *B01J 20/3212* (2013.01); *B01J 20/3274* (2013.01); *C07K 14/31* (2013.01); *C07K 16/065* (2013.01); *C07K 16/1271* (2013.01); *C07K 17/10* (2013.01); *B01J 2220/52* (2013.01)

(58) Field of Classification Search
None
See application file for complete search history.

(56) References Cited

To view the complete listing of prior art documents cited during the proceeding for Reexamination Control Number 90/015,234, please refer to the USPTO's Patent Electronic System.

*Primary Examiner* — Padmashri Ponnaluri

(57) ABSTRACT

The invention relates to a method of isolating an immunoglobulin, comprising the steps of:

a) providing a separation matrix comprising multimers of immunoglobulin-binding alkali-stabilized Protein A domains covalently coupled to a porous support, b) contacting a liquid sample comprising an immunoglobulin with the separation matrix, c) washing said separation matrix with a washing liquid, d) eluting the immunoglobulin from the separation matrix with an elution liquid, and e) cleaning the separation matrix with a cleaning liquid, wherein the alkali-stabilized Protein A domains comprise mutants of a parental Fe-binding domain of Staphylococcus Protein A (SpA), as defined by SEQ ID NO: 51 or SEQ ID NO: 52, wherein the amino acid residues at positions 13 and 44 of SEQ Ill NO: 51 or 52 are asparagines and wherein at least the asparagine residue at position 3 of SEQ ID NO: 51 or 52 has been mutated to an amino acid selected from the group consisting of glutamic acid, lysine, tyrosine, threonine, phenylalanine, leucine, isoleucine, tryptophan, methionine, valine, alanine, histidine and arginine.

US 11,623,941 C1

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 12-18 are determined to be patentable as amended.

Claims 2-11, dependent on an amended claim, are determined to be patentable.

Claims 19 and 20 were not reexamined.

1. A method of isolating an immunoglobulin, comprising the steps of:
   a) providing a separation matrix comprising at least 15 mg/ml multimers of immunoglobulin-binding alkali-stabilized Protein A domains covalently coupled to a porous support,
   b) contacting a liquid sample comprising an immunoglobulin with said separation matrix, wherein at least 40 mg immunoglobulin per ml separation matrix is contacted with said separation matrix,
   c) washing said separation matrix with a washing liquid,
   d) eluting the immunoglobulin from the separation matrix with an elution liquid, and
   e) cleaning the separation matrix with a cleaning liquid comprising at least 0.5 M NaOH,
   wherein said alkali-stabilized Protein A domains comprise an Fc-binding polypeptide having an amino acid sequence as defined by, or having at least [80%] *95%* identity to the sequence defined by $X_1QX_2AFYEILX_3LPNLTEEQRX_4X_5FIX_6X_7LKDX_8PSX_9SX_{10}X_{11}X_{12}LAEA KX_{13}X_{14}NX_{15}AQ$ (SEQ ID NO: 53) wherein individually of each other:
   [$X_1$=A or Q or is deleted
   $X_2$=E, K, Y, T, F, L, W, I, M, V, A, H or R
   $X_3$=H or K
   $X_4$=A or N
   $X_5$=A, G, S, Y, Q, T, N, F, L, W, I, M, V, D, E, H, R or K
   $X_6$=Q or E
   $X_7$=S or K
   $X_8$=E or D
   $X_9$=Q or V or is deleted
   $X_{10}$=K, R or A or is deleted
   $X_{11}$=A, E or N or is deleted
   $X_{12}$=I or L
   $X_{13}$=K or R
   $X_{14}$=L or Y
   $X_{15}$=D, F, Y, W, K or R]
   *$X_2$ must be E, $X_1$=A or is deleted, $X_3$=H, $X_4$=N, $X_5$=A, G, S, Y, Q, T, N, F, L, W, I, M, V, D, E, H, R or K, $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L, and $X_{15}$=D, F, Y, W, K or R;*
   *$X_2$ must be E, $X_1$=A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D;*
   *$X_2$ must be E, $X_1$ is A, $X_3$=H, $X_4$=N, $X_5$=A, G, S, Y, Q, T, N, F, L, W, I, M, V, D, E, H, R or K, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D; or*
   *$X_2$ must be E, K, Y, T, F, L, W, I, M, V, A, H or R, $X_1$=A, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.*

12. The method of claim 1, *wherein said alkali-stabilized Protein A domains comprise an Fc-binding polypeptide having an amino acid sequence having 100% identity to the sequence defined by SEQ ID NO: 53, and* wherein individually of each other:
    $X_1$=A or is deleted, $X_2$=E, $X_3$=H, $X_4$=N, *$X_5$=A, G, S, Y, Q, T, N, F, L, W, I, M, V, D, E, H, R or K,* $X_6$=Q, $X_7$=S, $X_8$=D, $X_9$=V or is deleted, $X_{10}$=K or is deleted, $X_{11}$=A or is deleted, $X_{12}$=I, $X_{13}$=K, $X_{14}$=L, *and $X_{15}$=D, F, Y, W, K or R.*

13. The method of claim 1, *wherein said alkali-stabilized Protein A domains comprise an Fc-binding polypeptide having an amino acid sequence having 95% identity to the sequence defined by SEQ ID NO: 53, and* wherein individually of each other:
    $X_1$=A, $X_2$ [=] *must be* E, $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

14. The method of claim 1, *wherein said alkali-stabilized Protein A domains comprise an Fc-binding polypeptide having an amino acid sequence having 100% identity to the sequence defined by SEQ ID NO: 53, and* wherein individually of each other:
    $X_1$ is A, $X_2$=E, $X_3$=H, $X_4$=N, *$X_5$=A, G, S, Y, Q, T, N, F, L, W, I, M, V, D, E, H, R or K,* $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

15. The method of claim 1, *wherein said alkali-stabilized Protein A domains comprise an Fc-binding polypeptide having an amino acid sequence having 100% identity to the sequence defined by SEQ ID NO: 53, and* wherein individually of each other:
    $X_1$ is A, *$X_2$=E, K, Y, T, F, L, W, I, M, V, A, H or R,* $X_3$=H, $X_4$=N, $X_5$=A, $X_6$=Q, $X_7$=S, $X_8$=D, $X_9$=V, $X_{10}$=K, $X_{11}$=A, $X_{12}$=I, $X_{13}$=K, $X_{14}$=L and $X_{15}$=D.

16. The method of claim 1, wherein said alkali-stabilized Protein A domains comprise an Fc-binding polypeptide having an amino acid sequence [having at least 90% identity to SEQ ID NO: 53] *VDAKFDKEAQEAFYEILHLPNLTE-EQRNAFIQSLKDDPSVSKAILAEAKKLNDAQAPK (SEQ ID NO: 11)*.

17. The method of claim 1, wherein said alkali-stabilized Protein A domains comprise an Fc-binding polypeptide having an amino acid sequence [having at least 95% identity to SEQ ID NO: 53] *AQEAFYEILHLPNLTEEQR-NAFIQSLKDDPSVSKAILAEAKKLNDAQAPK (SEQ ID NO: 94)*.

18. The method of claim 1, wherein said alkali-stabilized Protein A domains comprise an Fc-binding polypeptide having an amino acid sequence [having at least 98% identity to SEQ ID NO: 53] *VDAKFDKEAQEAFYEILHLPNLTE-EQRNAFIQSLKDDPSVSKEILAEAKKLNDAQAPK (SEQ ID NO: 10)*.

\* \* \* \* \*

                         SEQUENCE LISTING

<160> NUMBER OF SEQ ID NOS: 113

<210> SEQ ID NO 1
<211> LENGTH: 51
<212> TYPE: PRT
<213> ORGANISM: Staphylococcus aureus

<400> SEQUENCE: 1

Ala Gln Gln Asn Ala Phe Tyr Gln Val Leu Asn Met Pro Asn Leu Asn
1               5                   10                  15

Ala Asp Gln Arg Asn Gly Phe Ile Gln Ser Leu Lys Asp Asp Pro Ser
            20                  25                  30

Gln Ser Ala Asn Val Leu Gly Glu Ala Gln Lys Leu Asn Asp Ser Gln
        35                  40                  45

Ala Pro Lys
    50

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60
```

```
<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Escherichia coli

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 7
<211> LENGTH: 58
<212> TYPE: PRT
<213> ORGANISM: Escherichia coli

<400> SEQUENCE: 7

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Escherichia coli

<400> SEQUENCE: 8

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Ala Leu Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Escherichia coli

<400> SEQUENCE: 9

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Ala Ala Phe Ile Gln
            20                  25                  30

Ser Leu Lys Asp Asp Pro Ser Gln Ser Ala Ala Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Escherichia coli

<400> SEQUENCE: 10

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

```
<210> SEQ ID NO 11
<211> LENGTH: 58
<212> TYPE: PRT
<213> ORGANISM: Escherichia coli

<400> SEQUENCE: 11

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Escherichia coli

<400> SEQUENCE: 12

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Ala
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Escherichia coli

<400> SEQUENCE: 13

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Escherichia coli

<400> SEQUENCE: 14

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Glu
            20                  25                  30

Ser Leu Lys Asp Asp Pro Ser Glu Ser Ala Asn Leu Leu Ala Glu Ala
        35                  40                  45

Lys Lys Leu Asn Asp Ala Gln Ala Pro Lys
    50                  55
```

```
<210> SEQ ID NO 15
<211> LENGTH: 58
<212> TYPE: PRT
<213> ORGANISM: Escherichia coli

<400> SEQUENCE: 15

Val Asp Ala Lys Phe Asp Lys Glu Gln Gln Glu Ala Phe Tyr Glu Ile
1               5                   10                  15

Leu His Leu Pro Asn Leu Thr Glu Glu Gln Arg Asn Ala Phe Ile Glu
            20                  25                  30

Ser Leu Lys Asp Asp Pro Ser Gln Ser Ala Asn Leu Leu Ala Glu Ala
        35                  40                  45

Lys Arg Leu Asn Asp Ala Gln Ala Pro Lys
50                  55

<210> SEQ ID NO 16
<211> LENGTH: 58
<212> TYPE: PRT
<213> ORGANISM: Escherichia coli

<400> SEQUENCE: 16

Val Asp Ala Lys Phe Asp Lys Glu Gln Gln Lys Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
50                  55

<210> SEQ ID NO 17
<211> LENGTH: 237
<212> TYPE: PRT
<213> ORGANISM: Escherichia coli

<400> SEQUENCE: 17

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Gln Ser Ala Ala Leu
        35                  40                  45

Leu Ala Glu Ala Lys Lys Leu Asn Asp Ala Gln Ala Pro Lys Val Asp
    50                  55                  60

Ala Lys Phe Asp Lys Glu Ala Gln Glu Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Asp Pro Ser Gln Ser Ala Ala Leu Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Gln
145                 150                 155                 160

Ser Ala Ala Leu Leu Ala Glu Ala Lys Lys Leu Asn Asp Ala Gln Ala
                165                 170                 175
```

Pro Lys Val Asp Ala Lys Phe Asp Lys Glu Ala Gln Glu Ala Phe Tyr
              180                 185                 190

Glu Ile Leu His Leu Pro Asn Leu Thr Glu Glu Gln Arg Asn Ala Phe
          195                 200                 205

Ile Gln Ser Leu Lys Asp Asp Pro Ser Gln Ser Ala Ala Leu Leu Ala
      210                 215                 220

Glu Ala Lys Lys Leu Asn Asp Ala Gln Ala Pro Lys Cys
225                 230                 235

<210> SEQ ID NO 18
<211> LENGTH: 237
<212> TYPE: PRT
<213> ORGANISM: Escherichia coli

<400> SEQUENCE: 18

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Ala
            20                  25                  30

Ala Phe Ile Gln Ser Leu Lys Asp Asp Pro Ser Gln Ser Ala Ala Leu
        35                  40                  45

Leu Ala Glu Ala Lys Lys Leu Asn Asp Ala Gln Ala Pro Lys Val Asp
    50                  55                  60

Ala Lys Phe Asp Lys Glu Ala Gln Glu Ala Phe Tyr Glu Ile Leu His
65                  70                  75                  80

Leu Pro Asn Leu Thr Glu Glu Gln Arg Ala Ala Phe Ile Gln Ser Leu
                85                  90                  95

Lys Asp Asp Pro Ser Gln Ser Ala Ala Leu Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
    130                 135                 140

Glu Gln Arg Ala Ala Phe Ile Gln Ser Leu Lys Asp Asp Pro Ser Gln
145                 150                 155                 160

Ser Ala Ala Leu Leu Ala Glu Ala Lys Lys Leu Asn Asp Ala Gln Ala
                165                 170                 175

Pro Lys Val Asp Ala Lys Phe Asp Lys Glu Ala Gln Glu Ala Phe Tyr
            180                 185                 190

Glu Ile Leu His Leu Pro Asn Leu Thr Glu Glu Gln Arg Ala Ala Phe
        195                 200                 205

Ile Gln Ser Leu Lys Asp Asp Pro Ser Gln Ser Ala Ala Leu Leu Ala
    210                 215                 220

Glu Ala Lys Lys Leu Asn Asp Ala Gln Ala Pro Lys Cys
225                 230                 235

<210> SEQ ID NO 19
<211> LENGTH: 237
<212> TYPE: PRT
<213> ORGANISM: Escherichia coli

<400> SEQUENCE: 19

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Asn
            20                  25                  30

```
Ala Phe Ile Gln Ser Leu Lys Asp Asp Pro Ser Val Ser Lys Glu Ile
         35                  40                  45

Leu Ala Glu Ala Lys Lys Leu Asn Asp Ala Gln Ala Pro Lys Val Asp
 50                  55                  60

Ala Lys Phe Asp Lys Glu Ala Gln Glu Ala Phe Tyr Glu Ile Leu His
 65                  70                  75                  80

Leu Pro Asn Leu Thr Glu Glu Gln Arg Asn Ala Phe Ile Gln Ser Leu
                 85                  90                  95

Lys Asp Asp Pro Ser Val Ser Lys Glu Ile Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Val Asp Ala Lys Phe Asp Lys Glu Ala Gln Glu Ala Phe Tyr
            180                 185                 190

Glu Ile Leu His Leu Pro Asn Leu Thr Glu Glu Gln Arg Asn Ala Phe
        195                 200                 205

Ile Gln Ser Leu Lys Asp Asp Pro Ser Val Ser Lys Glu Ile Leu Ala
    210                 215                 220

Glu Ala Lys Lys Leu Asn Asp Ala Gln Ala Pro Lys Cys
225                 230                 235

<210> SEQ ID NO 20
<211> LENGTH: 237
<212> TYPE: PRT
<213> ORGANISM: Escherichia coli

<400> SEQUENCE: 20

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Asn
             20                  25                  30

Ala Phe Ile Gln Ser Leu Lys Asp Asp Pro Ser Val Ser Lys Ala Ile
         35                  40                  45

Leu Ala Glu Ala Lys Lys Leu Asn Asp Ala Gln Ala Pro Lys Val Asp
 50                  55                  60

Ala Lys Phe Asp Lys Glu Ala Gln Glu Ala Phe Tyr Glu Ile Leu His
 65                  70                  75                  80

Leu Pro Asn Leu Thr Glu Glu Gln Arg Asn Ala Phe Ile Gln Ser Leu
                 85                  90                  95

Lys Asp Asp Pro Ser Val Ser Lys Ala Ile Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Val
145                 150                 155                 160

Ser Lys Ala Ile Leu Ala Glu Ala Lys Lys Leu Asn Asp Ala Gln Ala
                165                 170                 175
```

Pro Lys Val Asp Ala Lys Phe Asp Lys Glu Ala Gln Glu Ala Phe Tyr
            180                 185                 190

Glu Ile Leu His Leu Pro Asn Leu Thr Glu Glu Gln Arg Asn Ala Phe
            195                 200                 205

Ile Gln Ser Leu Lys Asp Asp Pro Ser Val Ser Lys Ala Ile Leu Ala
            210                 215                 220

Glu Ala Lys Lys Leu Asn Asp Ala Gln Ala Pro Lys Cys
225                 230                 235

<210> SEQ ID NO 21
<211> LENGTH: 237
<212> TYPE: PRT
<213> ORGANISM: Escherichia coli

<400> SEQUENCE: 21

Ala Gln Gly Thr Val Asp Ala Lys Phe Asp Lys Glu Gln Gln Asn Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Gln Ser Ala Asn Leu
        35                  40                  45

Leu Ala Glu Ala Lys Lys Leu Asn Asp Ala Gln Ala Pro Lys Val Asp
50                  55                  60

Ala Lys Phe Asp Lys Glu Gln Gln Asn Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Asp Pro Ser Gln Ser Ala Asn Leu Leu Ala Glu Ala Lys Lys
            100                 105                 110

Leu Asn Asp Ala Gln Ala Pro Lys Val Asp Ala Lys Phe Asp Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Gln
145                 150                 155                 160

Ser Ala Asn Leu Leu Ala Glu Ala Lys Lys Leu Asn Asp Ala Gln Ala
                165                 170                 175

Pro Lys Val Asp Ala Lys Phe Asp Lys Glu Gln Gln Asn Ala Phe Tyr
            180                 185                 190

Glu Ile Leu His Leu Pro Asn Leu Thr Glu Glu Gln Arg Asn Ala Phe
            195                 200                 205

Ile Gln Ser Leu Lys Asp Asp Pro Ser Gln Ser Ala Asn Leu Leu Ala
        210                 215                 220

Glu Ala Lys Lys Leu Asn Asp Ala Gln Ala Pro Lys Cys
225                 230                 235

<210> SEQ ID NO 22
<211> LENGTH: 58
<212> TYPE: PRT
<213> ORGANISM: Staphylococcus aureus

<400> SEQUENCE: 22

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
　　　　　35　　　　　　　　　　40　　　　　　　　　　45

Lys Lys Leu Asn Glu Ser Gln Ala Pro Lys
 50　　　　　　　　　　55

<210> SEQ ID NO 23
<211> LENGTH: 58
<212> TYPE: PRT
<213> ORGANISM: Escherichia coli

<400> SEQUENCE: 23

Val Asp Ala Lys Phe Asp Lys Glu Gln Gln Lys Ala Phe Tyr Glu Ile
 1               5                  10                  15

Leu Lys Leu Pro Asn Leu Thr Glu Glu Gln Arg Asn Ala Phe Ile Gln
　　　　　20　　　　　　　　　　25　　　　　　　　　　30

Lys Leu Lys Asp Glu Pro Ser Gln Ser Arg Ala Ile Leu Ala Glu Ala
　　　　　35　　　　　　　　　　40　　　　　　　　　　45

Lys Arg Tyr Asn Asp Ala Gln Ala Pro Lys
 50　　　　　　　　　　55

<210> SEQ ID NO 24
<211> LENGTH: 58
<212> TYPE: PRT
<213> ORGANISM: Escherichia coli

<400> SEQUENCE: 24

Val Asp Ala Lys Phe Asp Lys Glu Ala Gln Glu Ala Phe Tyr Glu Ile
 1               5                  10                  15

Leu His Leu Pro Asn Leu Thr Glu Glu Gln Arg Ala Ala Phe Ile Gln
　　　　　20　　　　　　　　　　25　　　　　　　　　　30

Ser Leu Lys Asp Asp Pro Ser Val Ser Lys Ala Ile Leu Ala Glu Ala
　　　　　35　　　　　　　　　　40　　　　　　　　　　45

Lys Lys Leu Asn Asp Ala Gln Ala Pro Lys
 50　　　　　　　　　　55

<210> SEQ ID NO 25
<211> LENGTH: 58
<212> TYPE: PRT
<213> ORGANISM: Escherichia coli

<400> SEQUENCE: 25

Val Asp Ala Lys Phe Asp Lys Glu Ala Gln Lys Ala Phe Tyr Glu Ile
 1               5                  10                  15

Leu Lys Leu Pro Asn Leu Thr Glu Glu Gln Arg Ala Ala Phe Ile Gln
　　　　　20　　　　　　　　　　25　　　　　　　　　　30

Lys Leu Lys Asp Glu Pro Ser Gln Ser Arg Ala Ile Leu Ala Glu Ala
　　　　　35　　　　　　　　　　40　　　　　　　　　　45

Lys Arg Tyr Asn Asp Ala Gln Ala Pro Lys
 50　　　　　　　　　　55

<210> SEQ ID NO 26
<211> LENGTH: 58
<212> TYPE: PRT
<213> ORGANISM: Escherichia coli

<400> SEQUENCE: 26

Val Asp Ala Lys Phe Asp Lys Glu Gln Gln Lys Ala Phe Tyr Glu Ile
 1               5                  10                  15

Leu Lys Leu Pro Asn Leu Thr Glu Glu Gln Arg Asn Ala Phe Ile Gln
　　　　　20　　　　　　　　　　25　　　　　　　　　　30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55

<210> SEQ ID NO 27
<211> LENGTH: 58
<212> TYPE: PRT
<213> ORGANISM: Escherichia coli

<400> SEQUENCE: 27

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55

<210> SEQ ID NO 28
<211> LENGTH: 58
<212> TYPE: PRT
<213> ORGANISM: Escherichia coli

<400> SEQUENCE: 28

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Arg Leu Asn Asp Ala Gln Ala Pro Lys
    50                  55

<210> SEQ ID NO 29
<211> LENGTH: 58
<212> TYPE: PRT
<213> ORGANISM: Escherichia coli

<400> SEQUENCE: 29

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Asn Leu Leu Ala Glu Ala
        35                  40                  45

Lys Lys Leu Asn Asp Ala Gln Ala Pro Lys
    50                  55

<210> SEQ ID NO 30
<211> LENGTH: 237
<212> TYPE: PRT
<213> ORGANISM: Escherichia coli

<400> SEQUENCE: 30

Ala Gln Gly Thr Val Asp Ala Lys Phe Asp Lys Glu Gln Gln Lys Ala
1               5                   10                  15

Phe Tyr Glu Ile Leu Lys Leu Pro Asn Leu Thr Glu Glu Gln Arg Asn
            20                  25                  30

```
Ala Phe Ile Gln Lys Leu Lys Asp Glu Pro Ser Gln Ser Arg Ala Ile
            35                  40                  45

Leu Ala Glu Ala Lys Arg Tyr Asn Asp Ala Gln Ala Pro Lys Val Asp
 50                  55                  60

Ala Lys Phe Asp Lys Glu Gln Lys Ala Phe Tyr Glu Ile Leu Lys
 65                  70                  75                  80

Leu Pro Asn Leu Thr Glu Glu Arg Asn Ala Phe Ile Gln Lys Leu
                85                  90                  95

Lys Asp Glu Pro Ser Gln Ser Arg Ala Ile Leu Ala Glu Ala Lys Arg
                100                 105                 110

Tyr Asn Asp Ala Gln Ala Pro Lys Val Asp Ala Lys Phe Asp Lys Glu
                115                 120                 125

Gln Gln Lys Ala Phe Tyr Glu Ile Leu Lys Leu Pro Asn Leu Thr Glu
130                 135                 140

Glu Gln Arg Asn Ala Phe Ile Gln Lys Leu Lys Asp Glu Pro Ser Gln
145                 150                 155                 160

Ser Arg Ala Ile Leu Ala Glu Ala Lys Arg Tyr Asn Asp Ala Gln Ala
                165                 170                 175

Pro Lys Val Asp Ala Lys Phe Asp Lys Glu Gln Gln Lys Ala Phe Tyr
                180                 185                 190

Glu Ile Leu Lys Leu Pro Asn Leu Thr Glu Glu Gln Arg Asn Ala Phe
            195                 200                 205

Ile Gln Lys Leu Lys Asp Glu Pro Ser Gln Ser Arg Ala Ile Leu Ala
            210                 215                 220

Glu Ala Lys Arg Tyr Asn Asp Ala Gln Ala Pro Lys Cys
225                 230                 235

<210> SEQ ID NO 31
<211> LENGTH: 237
<212> TYPE: PRT
<213> ORGANISM: Escherichia coli

<400> SEQUENCE: 31

Ala Gln Gly Thr Val Asp Ala Lys Phe Asp Lys Glu Ala Gln Lys Ala
1               5                   10                  15

Phe Tyr Glu Ile Leu Lys Leu Pro Asn Leu Thr Glu Glu Gln Arg Asn
                20                  25                  30

Ala Phe Ile Gln Ser Leu Lys Asp Glu Pro Ser Gln Ser Arg Asn Leu
            35                  40                  45

Leu Ala Glu Ala Lys Lys Leu Asn Asp Ala Gln Ala Pro Lys Val Asp
 50                  55                  60

Ala Lys Phe Asp Lys Glu Ala Gln Lys Ala Phe Tyr Glu Ile Leu Lys
 65                  70                  75                  80

Leu Pro Asn Leu Thr Glu Glu Gln Arg Asn Ala Phe Ile Gln Ser Leu
                85                  90                  95

Lys Asp Glu Pro Ser Gln Ser Arg Asn Leu Leu Ala Glu Ala Lys Lys
                100                 105                 110

Leu Asn Asp Ala Gln Ala Pro Lys Val Asp Ala Lys Phe Asp Lys Glu
                115                 120                 125

Ala Gln Lys Ala Phe Tyr Glu Ile Leu Lys Leu Pro Asn Leu Thr Glu
130                 135                 140

Glu Gln Arg Asn Ala Phe Ile Gln Ser Leu Lys Asp Glu Pro Ser Gln
145                 150                 155                 160

Ser Arg Asn Leu Leu Ala Glu Ala Lys Lys Leu Asn Asp Ala Gln Ala
                165                 170                 175
```

Pro Lys Val Asp Ala Lys Phe Asp Lys Glu Ala Gln Lys Ala Phe Tyr
            180                 185                 190

Glu Ile Leu Lys Leu Pro Asn Leu Thr Glu Glu Gln Arg Asn Ala Phe
        195                 200                 205

Ile Gln Ser Leu Lys Asp Glu Pro Ser Gln Ser Arg Asn Leu Leu Ala
    210                 215                 220

Glu Ala Lys Lys Leu Asn Asp Ala Gln Ala Pro Lys Cys
225                 230                 235

<210> SEQ ID NO 32
<211> LENGTH: 237
<212> TYPE: PRT
<213> ORGANISM: Escherichia coli

<400> SEQUENCE: 32

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Ala
            20                  25                  30

Ala Phe Ile Gln Ser Leu Lys Asp Asp Pro Ser Val Ser Lys Ala Ile
        35                  40                  45

Leu Ala Glu Ala Lys Lys Leu Asn Asp Ala Gln Ala Pro Lys Val Asp
    50                  55                  60

Ala Lys Phe Asp Lys Glu Ala Gln Glu Ala Phe Tyr Glu Ile Leu His
65                  70                  75                  80

Leu Pro Asn Leu Thr Glu Glu Gln Arg Ala Ala Phe Ile Gln Ser Leu
                85                  90                  95

Lys Asp Asp Pro Ser Val Ser Lys Ala Ile Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
    130                 135                 140

Glu Gln Arg Ala Ala Phe Ile Gln Ser Leu Lys Asp Asp Pro Ser Val
145                 150                 155                 160

Ser Lys Ala Ile Leu Ala Glu Ala Lys Lys Leu Asn Asp Ala Gln Ala
                165                 170                 175

Pro Lys Val Asp Ala Lys Phe Asp Lys Glu Ala Gln Glu Ala Phe Tyr
            180                 185                 190

Glu Ile Leu His Leu Pro Asn Leu Thr Glu Glu Gln Arg Ala Ala Phe
        195                 200                 205

Ile Gln Ser Leu Lys Asp Asp Pro Ser Val Ser Lys Ala Ile Leu Ala
    210                 215                 220

Glu Ala Lys Lys Leu Asn Asp Ala Gln Ala Pro Lys Cys
225                 230                 235

<210> SEQ ID NO 33
<211> LENGTH: 353
<212> TYPE: PRT
<213> ORGANISM: Escherichia coli

<400> SEQUENCE: 33

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Val Ser Lys Ala Ile
                35                  40                  45

Leu Ala Glu Ala Lys Lys Leu Asn Asp Ala Gln Ala Pro Lys Val Asp
 50                  55                  60

Ala Lys Phe Asp Lys Glu Ala Gln Glu Ala Phe Tyr Glu Ile Leu His
 65                  70                  75                  80

Leu Pro Asn Leu Thr Glu Glu Gln Arg Asn Ala Phe Ile Gln Ser Leu
                 85                  90                  95

Lys Asp Asp Pro Ser Val Ser Lys Ala Ile Leu Ala Glu Ala Lys Lys
            100                 105                 110

Leu Asn Asp Ala Gln Ala Pro Lys Val Asp Ala Lys Phe Asp Lys Glu
            115                 120                 125

Ala Gln Glu Ala Phe Tyr Glu Ile Leu His Leu Pro Asn Leu Thr Glu
        130                 135                 140

Glu Gln Arg Asn Ala Phe Ile Gln Ser Leu Lys Asp Asp Pro Ser Val
145                 150                 155                 160

Ser Lys Ala Ile Leu Ala Glu Ala Lys Lys Leu Asn Asp Ala Gln Ala
                165                 170                 175

Pro Lys Val Asp Ala Lys Phe Asp Lys Glu Ala Gln Glu Ala Phe Tyr
            180                 185                 190

Glu Ile Leu His Leu Pro Asn Leu Thr Glu Glu Gln Arg Asn Ala Phe
        195                 200                 205

Ile Gln Ser Leu Lys Asp Asp Pro Ser Val Ser Lys Ala Ile Leu Ala
    210                 215                 220

Glu Ala Lys Lys Leu Asn Asp Ala Gln Ala Pro Lys Val Asp Ala Lys
225                 230                 235                 240

Phe Asp Lys Glu Ala Gln Glu Ala Phe Tyr Glu Ile Leu His Leu Pro
                245                 250                 255

Asn Leu Thr Glu Glu Gln Arg Asn Ala Phe Ile Gln Ser Leu Lys Asp
            260                 265                 270

Asp Pro Ser Val Ser Lys Ala Ile Leu Ala Glu Ala Lys Lys Leu Asn
            275                 280                 285

Asp Ala Gln Ala Pro Lys Val Asp Ala Lys Phe Asp Lys Glu Ala Gln
        290                 295                 300

Glu Ala Phe Tyr Glu Ile Leu His Leu Pro Asn Leu Thr Glu Glu Gln
305                 310                 315                 320

Arg Asn Ala Phe Ile Gln Ser Leu Lys Asp Asp Pro Ser Val Ser Lys
                325                 330                 335

Ala Ile Leu Ala Glu Ala Lys Lys Leu Asn Asp Ala Gln Ala Pro Lys
            340                 345                 350

Cys

<210> SEQ ID NO 34
<211> LENGTH: 237
<212> TYPE: PRT
<213> ORGANISM: Escherichia coli

<400> SEQUENCE: 34

Ala Gln Gly Thr Val Asp Ala Lys Phe Asp Lys Glu Ala Gln Glu Ala
 1               5                  10                  15

Phe Tyr Glu Ile Leu His Leu Pro Asn Leu Thr Glu Glu Gln Arg Asn
                20                  25                  30

Ala Phe Ile Gln Ser Leu Lys Asp Glu Pro Ser Val Ser Lys Ala Ile
                35                  40                  45

```
Leu Ala Glu Ala Lys Lys Leu Asn Asp Ala Gln Ala Pro Lys Val Asp
 50                  55                  60

Ala Lys Phe Asp Lys Glu Ala Gln Glu Ala Phe Tyr Glu Ile Leu His
 65                  70                  75                  80

Leu Pro Asn Leu Thr Glu Glu Gln Arg Asn Ala Phe Ile Gln Ser Leu
                 85                  90                  95

Lys Asp Glu Pro Ser Val Ser Lys Ala Ile Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
130                 135                 140

Glu Gln Arg Asn Ala Phe Ile Gln Ser Leu Lys Asp Glu Pro Ser Val
145                 150                 155                 160

Ser Lys Ala Ile Leu Ala Glu Ala Lys Lys Leu Asn Asp Ala Gln Ala
                165                 170                 175

Pro Lys Val Asp Ala Lys Phe Asp Lys Glu Ala Gln Glu Ala Phe Tyr
            180                 185                 190

Glu Ile Leu His Leu Pro Asn Leu Thr Glu Glu Gln Arg Asn Ala Phe
        195                 200                 205

Ile Gln Ser Leu Lys Asp Glu Pro Ser Val Ser Lys Ala Ile Leu Ala
    210                 215                 220

Glu Ala Lys Lys Leu Asn Asp Ala Gln Ala Pro Lys Cys
225                 230                 235

<210> SEQ ID NO 35
<211> LENGTH: 237
<212> TYPE: PRT
<213> ORGANISM: Escherichia coli

<400> SEQUENCE: 35

Ala Gln Gly Thr Val Asp Ala Lys Phe Asp Lys Glu Ala Gln Glu Ala
 1               5                  10                  15

Phe Tyr Glu Ile Leu His Leu Pro Asn Leu Thr Glu Glu Gln Arg Asn
                20                  25                  30

Ala Phe Ile Gln Ser Leu Lys Asp Glu Pro Ser Val Ser Arg Ala Ile
            35                  40                  45

Leu Ala Glu Ala Lys Lys Leu Asn Asp Ala Gln Ala Pro Lys Val Asp
 50                  55                  60

Ala Lys Phe Asp Lys Glu Ala Gln Glu Ala Phe Tyr Glu Ile Leu His
 65                  70                  75                  80

Leu Pro Asn Leu Thr Glu Glu Gln Arg Asn Ala Phe Ile Gln Ser Leu
                 85                  90                  95

Lys Asp Glu Pro Ser Val Ser Arg Ala Ile Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
130                 135                 140

Glu Gln Arg Asn Ala Phe Ile Gln Ser Leu Lys Asp Glu Pro Ser Val
145                 150                 155                 160

Ser Arg Ala Ile Leu Ala Glu Ala Lys Lys Leu Asn Asp Ala Gln Ala
                165                 170                 175

Pro Lys Val Asp Ala Lys Phe Asp Lys Glu Ala Gln Glu Ala Phe Tyr
            180                 185                 190
```

```
Glu Ile Leu His Leu Pro Asn Leu Thr Glu Glu Gln Arg Asn Ala Phe
        195                 200                 205

Ile Gln Ser Leu Lys Asp Glu Pro Ser Val Ser Arg Ala Ile Leu Ala
    210                 215                 220

Glu Ala Lys Lys Leu Asn Asp Ala Gln Ala Pro Lys Cys
225                 230                 235

<210> SEQ ID NO 36
<211> LENGTH: 58
<212> TYPE: PRT
<213> ORGANISM: Escherichia coli

<400> SEQUENCE: 36

Ala Asp Asn Lys Phe Asn Lys Glu Ala Gln Glu Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 37
<211> LENGTH: 58
<212> TYPE: PRT
<213> ORGANISM: Escherichia coli

<400> SEQUENCE: 37

Ala Asp Asn Lys Phe Asn Lys Glu Ala Gln Glu Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 38
<211> LENGTH: 58
<212> TYPE: PRT
<213> ORGANISM: Escherichia coli

<400> SEQUENCE: 38

Val Asp Ala Lys Phe Asp Lys Glu Gln Gln Tyr Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 39
<211> LENGTH: 58
<212> TYPE: PRT
<213> ORGANISM: Escherichia coli
```

```
<400> SEQUENCE: 39

Val Asp Ala Lys Phe Asp Lys Glu Gln Gln Thr Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 40
<211> LENGTH: 58
<212> TYPE: PRT
<213> ORGANISM: Escherichia coli

<400> SEQUENCE: 40

Val Asp Ala Lys Phe Asp Lys Glu Gln Gln Phe Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 41
<211> LENGTH: 58
<212> TYPE: PRT
<213> ORGANISM: Escherichia coli

<400> SEQUENCE: 41

Val Asp Ala Lys Phe Asp Lys Glu Gln Gln Leu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 42
<211> LENGTH: 58
<212> TYPE: PRT
<213> ORGANISM: Escherichia coli

<400> SEQUENCE: 42

Val Asp Ala Lys Phe Asp Lys Glu Gln Gln Trp Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 43
<211> LENGTH: 58
<212> TYPE: PRT
<213> ORGANISM: Escherichia coli
```

-continued

<400> SEQUENCE: 43

Val Asp Ala Lys Phe Asp Lys Glu Gln Gln Ile Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 44
<211> LENGTH: 58
<212> TYPE: PRT
<213> ORGANISM: Escherichia coli

<400> SEQUENCE: 44

Val Asp Ala Lys Phe Asp Lys Glu Gln Gln Met Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 45
<211> LENGTH: 58
<212> TYPE: PRT
<213> ORGANISM: Escherichia coli

<400> SEQUENCE: 45

Val Asp Ala Lys Phe Asp Lys Glu Gln Gln Val Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 46
<211> LENGTH: 58
<212> TYPE: PRT
<213> ORGANISM: Escherichia coli

<400> SEQUENCE: 46

Val Asp Ala Lys Phe Asp Lys Glu Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 47
<211> LENGTH: 58
<212> TYPE: PRT
<213> ORGANISM: Escherichia coli

```
<400> SEQUENCE: 47

Val Asp Ala Lys Phe Asp Lys Glu Gln Gln His Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 48
<211> LENGTH: 58
<212> TYPE: PRT
<213> ORGANISM: Escherichia coli

<400> SEQUENCE: 48

Val Asp Ala Lys Phe Asp Lys Glu Gln Gln Arg Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 49
<211> LENGTH: 58
<212> TYPE: PRT
<213> ORGANISM: Escherichia coli

<400> SEQUENCE: 49

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Glu Pro Ser Val Ser Lys Ala Ile Leu Ala Glu Ala
            35                  40                  45

Lys Lys Leu Asn Asp Ala Gln Ala Pro Lys
    50                  55

<210> SEQ ID NO 50
<211> LENGTH: 58
<212> TYPE: PRT
<213> ORGANISM: Escherichia coli

<400> SEQUENCE: 50

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Glu Pro Ser Val Ser Arg Ala Ile Leu Ala Glu Ala
            35                  40                  45

Lys Lys Leu Asn Asp Ala Gln Ala Pro Lys
    50                  55

<210> SEQ ID NO 51
<211> LENGTH: 47
<212> TYPE: PRT
<213> ORGANISM: Escherichia coli
```

```
<400> SEQUENCE: 51

Gln Gln Asn Ala Phe Tyr Glu Ile Leu His Leu Pro Asn Leu Thr Glu
1               5                   10                  15

Glu Gln Arg Asn Ala Phe Ile Gln Ser Leu Lys Asp Asp Pro Ser Gln
            20                  25                  30

Ser Ala Asn Leu Leu Ala Glu Ala Lys Lys Leu Asn Asp Ala Gln
        35                  40                  45

<210> SEQ ID NO 52
<211> LENGTH: 47
<212> TYPE: PRT
<213> ORGANISM: Staphylococcus aureus

<400> SEQUENCE: 52

Gln Gln Asn Ala Phe Tyr Glu Ile Leu His Leu Pro Asn Leu Thr Glu
1               5                   10                  15

Glu Gln Arg Asn Gly Phe Ile Gln Ser Leu Lys Asp Asp Pro Ser Val
            20                  25                  30

Ser Lys Glu Ile Leu Ala Glu Ala Lys Lys Leu Asn Asp Ala Gln
        35                  40                  45

<210> SEQ ID NO 53
<211> LENGTH: 47
<212> TYPE: PRT
<213> ORGANISM: Escherichia coli
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(36)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
```

```
<400> SEQUENCE: 53

Xaa Gln Xaa Ala Phe Tyr Glu Ile Leu Xaa Leu Pro Asn Leu Thr Glu
1               5                   10                  15

Glu Gln Arg Xaa Xaa Phe Ile Xaa Xaa Leu Lys Asp Xaa Pro Ser Xaa
            20                  25                  30

Ser Xaa Xaa Xaa Leu Ala Glu Ala Lys Xaa Xaa Asn Xaa Ala Gln
        35                  40                  45

<210> SEQ ID NO 54
<211> LENGTH: 58
<212> TYPE: PRT
<213> ORGANISM: Escherichia coli

<400> SEQUENCE: 54

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
50                  55

<210> SEQ ID NO 55
<211> LENGTH: 58
<212> TYPE: PRT
<213> ORGANISM: Escherichia coli

<400> SEQUENCE: 55

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ser Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
50                  55

<210> SEQ ID NO 56
<211> LENGTH: 58
<212> TYPE: PRT
<213> ORGANISM: Escherichia coli

<400> SEQUENCE: 56

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Tyr Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
50                  55

<210> SEQ ID NO 57
<211> LENGTH: 58
<212> TYPE: PRT
<213> ORGANISM: Escherichia coli
```

<400> SEQUENCE: 57

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Gln Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 58
<211> LENGTH: 58
<212> TYPE: PRT
<213> ORGANISM: Escherichia coli

<400> SEQUENCE: 58

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Thr Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 59
<211> LENGTH: 58
<212> TYPE: PRT
<213> ORGANISM: Escherichia coli

<400> SEQUENCE: 59

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Asn Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 60
<211> LENGTH: 58
<212> TYPE: PRT
<213> ORGANISM: Escherichia coli

<400> SEQUENCE: 60

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Phe Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 61
<211> LENGTH: 58
<212> TYPE: PRT
<213> ORGANISM: Escherichia coli

<400> SEQUENCE: 61

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Leu Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 62
<211> LENGTH: 58
<212> TYPE: PRT
<213> ORGANISM: Escherichia coli

<400> SEQUENCE: 62

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Trp Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 63
<211> LENGTH: 58
<212> TYPE: PRT
<213> ORGANISM: Escherichia coli

<400> SEQUENCE: 63

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ile Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 64
<211> LENGTH: 58
<212> TYPE: PRT
<213> ORGANISM: Escherichia coli

<400> SEQUENCE: 64

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Met Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 65
<211> LENGTH: 58
<212> TYPE: PRT
<213> ORGANISM: Escherichia coli

```
<400> SEQUENCE: 65

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Val Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 66
<211> LENGTH: 58
<212> TYPE: PRT
<213> ORGANISM: Escherichia coli

<400> SEQUENCE: 66

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Asp Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 67
<211> LENGTH: 58
<212> TYPE: PRT
<213> ORGANISM: Escherichia coli

<400> SEQUENCE: 67

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Glu Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 68
<211> LENGTH: 58
<212> TYPE: PRT
<213> ORGANISM: Escherichia coli

<400> SEQUENCE: 68

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn His Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 69
<211> LENGTH: 58
<212> TYPE: PRT
<213> ORGANISM: Escherichia coli
```

<400> SEQUENCE: 69

| Val | Asp | Ala | Lys | Phe | Asp | Lys | Glu | Ala | Gln | Glu | Ala | Phe | Tyr | Glu | Ile |
|---|---|---|---|---|---|---|---|---|---|---|---|---|---|---|---|
| 1 | | | | 5 | | | | | 10 | | | | | 15 | |

| Leu | His | Leu | Pro | Asn | Leu | Thr | Glu | Glu | Gln | Arg | Asn | Arg | Phe | Ile | Gln |
|---|---|---|---|---|---|---|---|---|---|---|---|---|---|---|---|
| | | | 20 | | | | | 25 | | | | | 30 | | |

| Ser | Leu | Lys | Asp | Asp | Pro | Ser | Val | Ser | Lys | Ala | Ile | Leu | Ala | Glu | Ala |
|---|---|---|---|---|---|---|---|---|---|---|---|---|---|---|---|
| | | 35 | | | | | 40 | | | | | 45 | | | |

| Lys | Lys | Leu | Asn | Asp | Ala | Gln | Ala | Pro | Lys |
|---|---|---|---|---|---|---|---|---|---|
| 50 | | | | | 55 | | | | |

<210> SEQ ID NO 70
<211> LENGTH: 58
<212> TYPE: PRT
<213> ORGANISM: Escherichia coli

<400> SEQUENCE: 70

| Val | Asp | Ala | Lys | Phe | Asp | Lys | Glu | Ala | Gln | Glu | Ala | Phe | Tyr | Glu | Ile |
|---|---|---|---|---|---|---|---|---|---|---|---|---|---|---|---|
| 1 | | | | 5 | | | | | 10 | | | | | 15 | |

| Leu | His | Leu | Pro | Asn | Leu | Thr | Glu | Glu | Gln | Arg | Asn | Lys | Phe | Ile | Gln |
|---|---|---|---|---|---|---|---|---|---|---|---|---|---|---|---|
| | | | 20 | | | | | 25 | | | | | 30 | | |

| Ser | Leu | Lys | Asp | Asp | Pro | Ser | Val | Ser | Lys | Ala | Ile | Leu | Ala | Glu | Ala |
|---|---|---|---|---|---|---|---|---|---|---|---|---|---|---|---|
| | | 35 | | | | | 40 | | | | | 45 | | | |

| Lys | Lys | Leu | Asn | Asp | Ala | Gln | Ala | Pro | Lys |
|---|---|---|---|---|---|---|---|---|---|
| 50 | | | | | 55 | | | | |

<210> SEQ ID NO 71
<211> LENGTH: 58
<212> TYPE: PRT
<213> ORGANISM: Escherichia coli

<400> SEQUENCE: 71

| Val | Asp | Ala | Lys | Phe | Asp | Lys | Glu | Ala | Gln | Glu | Ala | Phe | Tyr | Glu | Ile |
|---|---|---|---|---|---|---|---|---|---|---|---|---|---|---|---|
| 1 | | | | 5 | | | | | 10 | | | | | 15 | |

| Leu | His | Leu | Pro | Asn | Leu | Thr | Glu | Glu | Gln | Arg | Asn | Ala | Phe | Ile | Gln |
|---|---|---|---|---|---|---|---|---|---|---|---|---|---|---|---|
| | | | 20 | | | | | 25 | | | | | 30 | | |

| Ser | Leu | Lys | Asp | Asp | Pro | Ser | Val | Ser | Lys | Ala | Ile | Leu | Ala | Glu | Ala |
|---|---|---|---|---|---|---|---|---|---|---|---|---|---|---|---|
| | | 35 | | | | | 40 | | | | | 45 | | | |

| Lys | Lys | Leu | Asn | Phe | Ala | Gln | Ala | Pro | Lys |
|---|---|---|---|---|---|---|---|---|---|
| 50 | | | | | 55 | | | | |

<210> SEQ ID NO 72
<211> LENGTH: 58
<212> TYPE: PRT
<213> ORGANISM: Escherichia coli

<400> SEQUENCE: 72

| Val | Asp | Ala | Lys | Phe | Asp | Lys | Glu | Ala | Gln | Glu | Ala | Phe | Tyr | Glu | Ile |
|---|---|---|---|---|---|---|---|---|---|---|---|---|---|---|---|
| 1 | | | | 5 | | | | | 10 | | | | | 15 | |

| Leu | His | Leu | Pro | Asn | Leu | Thr | Glu | Glu | Gln | Arg | Asn | Ala | Phe | Ile | Gln |
|---|---|---|---|---|---|---|---|---|---|---|---|---|---|---|---|
| | | | 20 | | | | | 25 | | | | | 30 | | |

| Ser | Leu | Lys | Asp | Asp | Pro | Ser | Val | Ser | Lys | Ala | Ile | Leu | Ala | Glu | Ala |
|---|---|---|---|---|---|---|---|---|---|---|---|---|---|---|---|
| | | 35 | | | | | 40 | | | | | 45 | | | |

| Lys | Lys | Leu | Asn | Tyr | Ala | Gln | Ala | Pro | Lys |
|---|---|---|---|---|---|---|---|---|---|
| 50 | | | | | 55 | | | | |

<210> SEQ ID NO 73
<211> LENGTH: 58
<212> TYPE: PRT
<213> ORGANISM: Escherichia coli

```
<400> SEQUENCE: 73

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Val Ser Lys Ala Ile Leu Ala Glu Ala
            35                  40                  45

Lys Lys Leu Asn Trp Ala Gln Ala Pro Lys
    50                  55

<210> SEQ ID NO 74
<211> LENGTH: 58
<212> TYPE: PRT
<213> ORGANISM: Escherichia coli

<400> SEQUENCE: 74

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Val Ser Lys Ala Ile Leu Ala Glu Ala
            35                  40                  45

Lys Lys Leu Asn Lys Ala Gln Ala Pro Lys
    50                  55

<210> SEQ ID NO 75
<211> LENGTH: 58
<212> TYPE: PRT
<213> ORGANISM: Escherichia coli

<400> SEQUENCE: 75

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Val Ser Lys Ala Ile Leu Ala Glu Ala
            35                  40                  45

Lys Lys Leu Asn Arg Ala Gln Ala Pro Lys
    50                  55

<210> SEQ ID NO 76
<211> LENGTH: 57
<212> TYPE: PRT
<213> ORGANISM: Escherichia coli

<400> SEQUENCE: 76

Val Asp Ala Lys Phe Asp Lys Glu Gln Glu Ala Phe Tyr Glu Ile Leu
1               5                   10                  15

His Leu Pro Asn Leu Thr Glu Glu Gln Arg Asn Ala Phe Ile Gln Ser
                20                  25                  30

Leu Lys Asp Asp Pro Ser Val Ser Lys Ala Ile Leu Ala Glu Ala Lys
            35                  40                  45

Lys Leu Asn Asp Ala Gln Ala Pro Lys
    50                  55

<210> SEQ ID NO 77
<211> LENGTH: 57
<212> TYPE: PRT
<213> ORGANISM: Escherichia coli
```

```
<400> SEQUENCE: 77

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Lys Ala Ile Leu Ala Glu Ala Lys
        35                  40                  45

Lys Leu Asn Asp Ala Gln Ala Pro Lys
    50                  55

<210> SEQ ID NO 78
<211> LENGTH: 57
<212> TYPE: PRT
<213> ORGANISM: Escherichia coli

<400> SEQUENCE: 78

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Ala Ile Leu Ala Glu Ala Lys
        35                  40                  45

Lys Leu Asn Asp Ala Gln Ala Pro Lys
    50                  55

<210> SEQ ID NO 79
<211> LENGTH: 57
<212> TYPE: PRT
<213> ORGANISM: Escherichia coli

<400> SEQUENCE: 79

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ile Leu Ala Glu Ala Lys
        35                  40                  45

Lys Leu Asn Asp Ala Gln Ala Pro Lys
    50                  55

<210> SEQ ID NO 80
<211> LENGTH: 114
<212> TYPE: PRT
<213> ORGANISM: Escherichia coli

<400> SEQUENCE: 80

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys Val Phe Asp Lys Glu Ala
    50                  55                  60

Gln Glu Ala Phe Tyr Glu Ile Leu His Leu Pro Asn Leu Thr Glu Glu
65                  70                  75                  80
```

```
Gln Arg Asn Ala Phe Ile Gln Ser Leu Lys Asp Asp Pro Ser Val Ser
                85                  90                  95

Lys Ala Ile Leu Ala Glu Ala Lys Lys Leu Asn Asp Ala Gln Ala Pro
            100                 105                 110

Lys Cys

<210> SEQ ID NO 81
<211> LENGTH: 114
<212> TYPE: PRT
<213> ORGANISM: Escherichia coli

<400> SEQUENCE: 81

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Ala Lys Phe Asp Lys Glu Ala
50                  55                  60

Gln Glu Ala Phe Tyr Glu Ile Leu His Leu Pro Asn Leu Thr Glu Glu
65                  70                  75                  80

Gln Arg Asn Ala Phe Ile Gln Ser Leu Lys Asp Asp Pro Ser Val Ser
                85                  90                  95

Lys Ala Ile Leu Ala Glu Ala Lys Lys Leu Asn Asp Ala Gln Ala Pro
            100                 105                 110

Lys Cys

<210> SEQ ID NO 82
<211> LENGTH: 114
<212> TYPE: PRT
<213> ORGANISM: Escherichia coli

<400> SEQUENCE: 82

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Ala Lys Phe Asp Lys Glu Ala
50                  55                  60

Gln Glu Ala Phe Tyr Glu Ile Leu His Leu Pro Asn Leu Thr Glu Glu
65                  70                  75                  80

Gln Arg Asn Ala Phe Ile Gln Ser Leu Lys Asp Asp Pro Ser Val Ser
                85                  90                  95

Lys Ala Ile Leu Ala Glu Ala Lys Lys Leu Asn Asp Ala Gln Ala Pro
            100                 105                 110

Lys Cys

<210> SEQ ID NO 83
<211> LENGTH: 112
<212> TYPE: PRT
<213> ORGANISM: Escherichia coli
```

-continued

```
<400> SEQUENCE: 83

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys Val Asp Ala Ala Gln Glu
    50                  55                  60

Ala Phe Tyr Glu Ile Leu His Leu Pro Asn Leu Thr Glu Glu Gln Arg
65                  70                  75                  80

Asn Ala Phe Ile Gln Ser Leu Lys Asp Asp Pro Ser Val Ser Lys Ala
                85                  90                  95

Ile Leu Ala Glu Ala Lys Lys Leu Asn Asp Ala Gln Ala Pro Lys Cys
            100                 105                 110

<210> SEQ ID NO 84
<211> LENGTH: 114
<212> TYPE: PRT
<213> ORGANISM: Escherichia coli

<400> SEQUENCE: 84

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Val Asp Ala Lys Phe Asp Lys Glu Ala
    50                  55                  60

Gln Glu Ala Phe Tyr Glu Ile Leu His Leu Pro Asn Leu Thr Glu Glu
65                  70                  75                  80

Gln Arg Asn Ala Phe Ile Gln Ser Leu Lys Asp Asp Pro Ser Val Ser
                85                  90                  95

Lys Ala Ile Leu Ala Glu Ala Lys Lys Leu Asn Asp Ala Gln Ala Pro
            100                 105                 110

Lys Cys

<210> SEQ ID NO 85
<211> LENGTH: 114
<212> TYPE: PRT
<213> ORGANISM: Escherichia coli

<400> SEQUENCE: 85

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys Lys Phe Asp Lys Glu Ala
    50                  55                  60

Gln Glu Ala Phe Tyr Glu Ile Leu His Leu Pro Asn Leu Thr Glu Glu
65                  70                  75                  80
```

Gln Arg Asn Ala Phe Ile Gln Ser Leu Lys Asp Asp Pro Ser Val Ser
                85                  90                  95
Lys Ala Ile Leu Ala Glu Ala Lys Lys Leu Asn Asp Ala Gln Ala Pro
            100                 105                 110
Lys Cys

<210> SEQ ID NO 86
<211> LENGTH: 109
<212> TYPE: PRT
<213> ORGANISM: Escherichia coli

<400> SEQUENCE: 86

Val Asp Ala Lys Phe Asp Lys Glu Ala Gln Glu Ala Phe Tyr Glu Ile
1               5                   10                  15
Leu His Leu Pro Asn Leu Thr Glu Glu Gln Arg Asn Ala Phe Ile Gln
            20                  25                  30
Ser Leu Lys Asp Asp Pro Ser Val Ser Lys Ala Ile Leu Ala Glu Ala
        35                  40                  45
Lys Lys Leu Asn Asp Ala Gln Ala Pro Lys Ala Gln Glu Ala Phe Tyr
    50                  55                  60
Glu Ile Leu His Leu Pro Asn Leu Thr Glu Glu Gln Arg Asn Ala Phe
65                  70                  75                  80
Ile Gln Ser Leu Lys Asp Asp Pro Ser Val Ser Lys Ala Ile Leu Ala
                85                  90                  95
Glu Ala Lys Lys Leu Asn Asp Ala Gln Ala Pro Lys Cys
            100                 105

<210> SEQ ID NO 87
<211> LENGTH: 121
<212> TYPE: PRT
<213> ORGANISM: Escherichia coli

<400> SEQUENCE: 87

Val Asp Ala Lys Phe Asp Lys Glu Ala Gln Glu Ala Phe Tyr Glu Ile
1               5                   10                  15
Leu His Leu Pro Asn Leu Thr Glu Glu Gln Arg Asn Ala Phe Ile Gln
            20                  25                  30
Ser Leu Lys Asp Asp Pro Ser Val Ser Lys Ala Ile Leu Ala Glu Ala
        35                  40                  45
Lys Lys Leu Asn Asp Ala Gln Ala Pro Lys Tyr Glu Asp Gly Val Asp
    50                  55                  60
Ala Lys Phe Asp Lys Glu Ala Gln Glu Ala Phe Tyr Glu Ile Leu His
65                  70                  75                  80
Leu Pro Asn Leu Thr Glu Glu Gln Arg Asn Ala Phe Ile Gln Ser Leu
                85                  90                  95
Lys Asp Asp Pro Ser Val Ser Lys Ala Ile Leu Ala Glu Ala Lys Lys
            100                 105                 110
Leu Asn Asp Ala Gln Ala Pro Lys Cys
        115                 120

<210> SEQ ID NO 88
<211> LENGTH: 117
<212> TYPE: PRT
<213> ORGANISM: Escherichia coli

```
<400> SEQUENCE: 88

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Ala Ile Leu Ala Glu Ala
        35                  40                  45

Lys Lys Leu Asn Asp Ala Gln Ala Pro Lys Val Asp Ala Lys Phe Asp
50                  55                  60

Lys Glu Ala Gln Glu Ala Phe Tyr Glu Ile Leu His Leu Pro Asn Leu
65                  70                  75                  80

Thr Glu Glu Gln Arg Asn Ala Phe Ile Gln Ser Leu Lys Asp Asp Pro
                85                  90                  95

Ser Val Ser Lys Ala Ile Leu Ala Glu Ala Lys Lys Leu Asn Asp Ala
            100                 105                 110

Gln Ala Pro Lys Cys
        115

<210> SEQ ID NO 89
<211> LENGTH: 55
<212> TYPE: PRT
<213> ORGANISM: Escherichia coli

<400> SEQUENCE: 89

Val Phe Asp Lys Glu Ala Gln Glu Ala Phe Tyr Glu Ile Leu His Leu
1               5                   10                  15

Pro Asn Leu Thr Glu Glu Gln Arg Asn Ala Phe Ile Gln Ser Leu Lys
            20                  25                  30

Asp Asp Pro Ser Val Ser Lys Ala Ile Leu Ala Glu Ala Lys Lys Leu
        35                  40                  45

Asn Asp Ala Gln Ala Pro Lys
    50                  55

<210> SEQ ID NO 90
<211> LENGTH: 55
<212> TYPE: PRT
<213> ORGANISM: Escherichia coli

<400> SEQUENCE: 90

Ala Lys Phe Asp Lys Glu Ala Gln Glu Ala Phe Tyr Glu Ile Leu His
1               5                   10                  15

Leu Pro Asn Leu Thr Glu Glu Gln Arg Asn Ala Phe Ile Gln Ser Leu
            20                  25                  30

Lys Asp Asp Pro Ser Val Ser Lys Ala Ile Leu Ala Glu Ala Lys Lys
        35                  40                  45

Leu Asn Asp Ala Gln Ala Pro
    50                  55

<210> SEQ ID NO 91
<211> LENGTH: 53
<212> TYPE: PRT
<213> ORGANISM: Escherichia coli

<400> SEQUENCE: 91

Val Asp Ala Ala Gln Glu Ala Phe Tyr Glu Ile Leu His Leu Pro Asn
1               5                   10                  15

Leu Thr Glu Glu Gln Arg Asn Ala Phe Ile Gln Ser Leu Lys Asp Asp
            20                  25                  30
```

Pro Ser Val Ser Lys Ala Ile Leu Ala Glu Ala Lys Lys Leu Asn Asp
                35                  40                  45

Ala Gln Ala Pro Lys
    50

<210> SEQ ID NO 92
<211> LENGTH: 55
<212> TYPE: PRT
<213> ORGANISM: Escherichia coli

<400> SEQUENCE: 92

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Val Ser Lys Ala Ile Leu Ala Glu Ala
                35                  40                  45

Lys Lys Leu Asn Asp Ala Gln
        50                  55

<210> SEQ ID NO 93
<211> LENGTH: 55
<212> TYPE: PRT
<213> ORGANISM: Escherichia coli

<400> SEQUENCE: 93

Lys Phe Asp Lys Glu Ala Gln Glu Ala Phe Tyr Glu Ile Leu His Leu
1               5                   10                  15

Pro Asn Leu Thr Glu Glu Gln Arg Asn Ala Phe Ile Gln Ser Leu Lys
                20                  25                  30

Asp Asp Pro Ser Val Ser Lys Ala Ile Leu Ala Glu Ala Lys Lys Leu
                35                  40                  45

Asn Asp Ala Gln Ala Pro Lys
        50                  55

<210> SEQ ID NO 94
<211> LENGTH: 50
<212> TYPE: PRT
<213> ORGANISM: Escherichia coli

<400> SEQUENCE: 94

Ala Gln Glu Ala Phe Tyr Glu Ile Leu His Leu Pro Asn Leu Thr Glu
1               5                   10                  15

Glu Gln Arg Asn Ala Phe Ile Gln Ser Leu Lys Asp Asp Pro Ser Val
                20                  25                  30

Ser Lys Ala Ile Leu Ala Glu Ala Lys Lys Leu Asn Asp Ala Gln Ala
                35                  40                  45

Pro Lys
    50

<210> SEQ ID NO 95
<211> LENGTH: 62
<212> TYPE: PRT
<213> ORGANISM: Escherichia coli

<400> SEQUENCE: 95

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
                20                  25                  30

```
Ser Leu Lys Asp Asp Pro Ser Val Ser Lys Ala Ile Leu Ala Glu Ala
        35                  40                  45

Lys Lys Leu Asn Asp Ala Gln Ala Pro Lys Tyr Glu Asp Gly
    50                  55                  60

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Pro Lys Val Asp Ala Lys Phe Asp Lys Glu
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Pro Lys Val Asp Asn Lys Phe Asn Lys Glu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Pro Lys Ala Asp Asn Lys Phe Asn Lys Glu
1               5                   10

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Pro Lys Val Phe Asp Lys Glu
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Pro Ala Lys Phe Asp Lys Glu
1               5
```

```
<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Lys Phe Asp Lys Glu
1               5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Pro Lys Val Asp Ala
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Val Asp Ala Lys Phe Asp Lys Glu
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Pro Lys Lys Phe Asp Lys Glu
1               5

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Pro Lys Tyr Glu Asp Gly Val Asp Ala Lys Phe Asp Lys Glu
1               5                   10                  15

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 106

Tyr Glu Asp Gly
1

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Pro Lys Phe Asn Lys Glu
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Pro Lys Phe Asp Lys Glu
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Pro Lys Val Asp Lys Glu
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Pro Lys Ala Asp Lys Glu
1               5

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Gln Gly Thr
1
```

```
<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Gln Val Asp Ala Lys Phe Asp Lys Glu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Gln Gly Thr Val Asp Ala Lys Phe Asp Lys Glu
1               5                   10
```